(12) United States Patent
Tan et al.

(10) Patent No.: US 10,687,707 B2
(45) Date of Patent: Jun. 23, 2020

(54) DETECTING ACTIVITY BY A WHEELCHAIR USER

(71) Applicant: APPLE INC., Cupertino, CA (US)

(72) Inventors: Xing Tan, San Jose, CA (US); Karthik Jayaraman Raghuram, Santa Clara, CA (US); Adeeti Ullal, Cupertino, CA (US); Umamahesh Srinivas, Milpitas, CA (US); Mrinal Agarwal, Cupertino, CA (US); Daniel Trietsch, Cupertino, CA (US); Alexander Singh Alvarado, Mountain View, CA (US); Hung A. Pham, Oakland, CA (US); Ronald K. Huang, San Jose, CA (US); Adam Howell, Oakland, CA (US)

(73) Assignee: APPLE INC., Cupertino, CA (US)

( * ) Notice: Subject to any disclaimer, the term of this patent is extended or adjusted under 35 U.S.C. 154(b) by 392 days.

(21) Appl. No.: 15/616,135

(22) Filed: Jun. 7, 2017

(65) Prior Publication Data

US 2017/0347885 A1 Dec. 7, 2017

Related U.S. Application Data

(60) Provisional application No. 62/346,667, filed on Jun. 7, 2016, provisional application No. 62/346,727, filed
(Continued)

(51) Int. Cl.
*A61B 5/22* (2006.01)
*A61B 5/00* (2006.01)
(Continued)

(52) U.S. Cl.
CPC ........ *A61B 5/0022* (2013.01); *A61B 5/02416* (2013.01); *A61B 5/02438* (2013.01);
(Continued)

(58) Field of Classification Search
CPC ......... A61B 5/0022; A61B 5/22; A61B 5/221; A61B 5/222; A61B 5/68; A61B 5/681;
(Continued)

(56) References Cited

U.S. PATENT DOCUMENTS 4,566,461 A 1/1986 Lubell et al.
5,158,093 A 10/1992 Shvartz et al.
(Continued)

FOREIGN PATENT DOCUMENTS

GB 2465824 6/2010
IN 259/KOL/2015 12/2015
(Continued)

OTHER PUBLICATIONS

Le, et al., "Sensor-based Training Optimization of a Cyclist Group", Seventh International Conference on Hybrid Intelligent Systems, IEEE 2007, pp. 265-270.
(Continued)

*Primary Examiner* — Eric F Winakur
(74) *Attorney, Agent, or Firm* — DLA Piper LLP US

(57) ABSTRACT

The present disclosure relates to a system and method of detecting activity by a wheelchair user. In one aspect, a method comprises collecting motion data of a user device located on an appendage of the user; detecting, by a processor circuit, that one or more activities by the wheelchair user occurred based on the motion data; calculating, by a processor circuit, an energy expenditure by the user based the one or more activities by the wheelchair user occurred; and outputting, by a processor circuit, the energy expenditure estimation.

31 Claims, 52 Drawing Sheets

Related U.S. Application Data on Jun. 7, 2016, provisional application No. 62/346,795, filed on Jun. 7, 2016, provisional application No. 62/381,678, filed on Aug. 31, 2016, provisional application No. 62/381,878, filed on Aug. 31, 2016.

(51) Int. Cl.
  *A61B 5/11* (2006.01)
  *A61G 5/10* (2006.01)
  *A61B 5/024* (2006.01)
  *A61G 5/02* (2006.01)

(52) U.S. Cl.
  CPC ........... *A61B 5/1112* (2013.01); *A61B 5/1118* (2013.01); *A61B 5/1123* (2013.01); *A61B 5/22* (2013.01); *A61B 5/222* (2013.01); *A61B 5/4866* (2013.01); *A61B 5/681* (2013.01); *A61G 5/10* (2013.01); *A61B 2562/0219* (2013.01); *A61B 2562/0247* (2013.01); *A61G 5/02* (2013.01); *A61G 5/1035* (2013.01); *A61G 2203/36* (2013.01)

(58) Field of Classification Search
  CPC ... A61B 5/6824; A61B 5/1118; A61B 5/1123; A61B 5/7282; A61B 5/742; A61B 5/7425
  See application file for complete search history.

(56) References Cited

U.S. PATENT DOCUMENTS

| | | | |
|---|---|---|---|
| 5,663,897 | A | 9/1997 | Geiser |
| 6,013,008 | A | 1/2000 | Fukushima |
| 6,059,724 | A | 5/2000 | Campell et al. |
| 6,582,380 | B2 | 6/2003 | Kazlausky et al. |
| 6,687,535 | B2 | 2/2004 | Hautala et al. |
| 6,837,827 | B1 | 1/2005 | Lee et al. |
| 6,868,338 | B1 | 3/2005 | Elliott |
| 7,254,516 | B2 | 8/2007 | Case, Jr. et al. |
| 7,311,675 | B2* | 12/2007 | Peifer ................... A61B 5/1118 600/587 |
| 7,467,060 | B2 | 12/2008 | Kulach et al. |
| 7,534,206 | B1 | 5/2009 | Lovitt et al. |
| 7,690,556 | B1 | 4/2010 | Kahn et al. |
| 7,771,320 | B2 | 8/2010 | Riley et al. |
| 7,805,149 | B2 | 9/2010 | Werner et al. |
| 7,841,967 | B1 | 11/2010 | Kahn et al. |
| 8,290,480 | B2 | 10/2012 | Abramson et al. |
| 8,483,775 | B2 | 7/2013 | Buck et al. |
| 8,589,174 | B2 | 11/2013 | Nelson et al. |
| 8,892,391 | B2 | 11/2014 | Tu et al. |
| 8,894,576 | B2 | 11/2014 | Alwan et al. |
| 8,911,329 | B2 | 12/2014 | Lin et al. |
| 9,413,871 | B2 | 8/2016 | Nixon et al. |
| 9,526,430 | B2 | 12/2016 | Srinivas et al. |
| 9,788,794 | B2 | 10/2017 | Le Boeuf et al. |
| 10,188,347 | B2 | 1/2019 | Self et al. |
| 10,206,627 | B2 | 2/2019 | Le Boeuf et al. |
| 10,219,708 | B2 | 3/2019 | Altini |
| 10,292,606 | B2 | 5/2019 | Wisbey et al. |
| 2001/0022828 | A1 | 9/2001 | Pyles |
| 2002/0019585 | A1 | 2/2002 | Dickinson |
| 2003/0032460 | A1 | 2/2003 | Cannon et al. |
| 2003/0138763 | A1 | 7/2003 | Roncalez et al. |
| 2004/0064061 | A1 | 4/2004 | Nissila |
| 2005/0107723 | A1 | 5/2005 | Wehman et al. |
| 2006/0064277 | A1 | 3/2006 | Jung et al. |
| 2006/0136173 | A1 | 6/2006 | Case et al. |
| 2006/0190217 | A1 | 8/2006 | Lee et al. |
| 2006/0217231 | A1 | 9/2006 | Parks et al. |
| 2007/0100666 | A1 | 5/2007 | Stivoric et al. |
| 2007/0150229 | A1 | 6/2007 | Fujiwara |
| 2007/0219059 | A1 | 9/2007 | Schwartz et al. |
| 2007/0275825 | A1 | 11/2007 | O'Brien |
| 2007/0276271 | A1 | 11/2007 | Chan |
| 2008/0096726 | A1 | 4/2008 | Riley et al. |
| 2008/0214360 | A1 | 9/2008 | Stirling et al. |
| 2009/0009320 | A1 | 1/2009 | O'Connor et al. |
| 2009/0024332 | A1 | 1/2009 | Karlov et al. |
| 2009/0043531 | A1 | 2/2009 | Kahn et al. |
| 2009/0063099 | A1* | 3/2009 | Counts ................... G01C 21/20 702/188 |
| 2010/0030350 | A1 | 2/2010 | House et al. |
| 2010/0130890 | A1 | 5/2010 | Matsumura et al. |
| 2010/0184564 | A1 | 7/2010 | Molyneux et al. |
| 2010/0204952 | A1 | 8/2010 | Irlam et al. |
| 2010/0210953 | A1 | 8/2010 | Sholder et al. |
| 2010/0210975 | A1 | 8/2010 | Anthony, III et al. |
| 2010/0217099 | A1 | 8/2010 | Leboeuf et al. |
| 2010/0274102 | A1 | 10/2010 | Teixeira |
| 2010/0298656 | A1 | 11/2010 | McCombie et al. |
| 2011/0040193 | A1 | 2/2011 | Seppanen et al. |
| 2011/0054359 | A1 | 3/2011 | Sazonov et al. |
| 2011/0082008 | A1 | 4/2011 | Cheung et al. |
| 2011/0131012 | A1 | 6/2011 | Czaja et al. |
| 2011/0152695 | A1 | 6/2011 | Granqvist et al. |
| 2011/0195707 | A1 | 8/2011 | Faerber et al. |
| 2011/0238485 | A1 | 9/2011 | Haumont et al. |
| 2011/0301436 | A1 | 12/2011 | Teixeira |
| 2012/0083715 | A1 | 4/2012 | Friedman |
| 2012/0172677 | A1 | 7/2012 | Beith |
| 2012/0238832 | A1 | 9/2012 | Hwang |
| 2012/0296455 | A1 | 11/2012 | Ohnemus et al. |
| 2012/0322621 | A1 | 12/2012 | Bingham et al. |
| 2013/0023739 | A1 | 1/2013 | Russel |
| 2013/0041590 | A1 | 2/2013 | Burich et al. |
| 2013/0053990 | A1 | 2/2013 | Ackland |
| 2013/0096943 | A1 | 4/2013 | Carey et al. |
| 2013/0158686 | A1 | 6/2013 | Zhang et al. |
| 2013/0178335 | A1 | 7/2013 | Lin et al. |
| 2013/0197377 | A1 | 8/2013 | Takahiko et al. |
| 2013/0218053 | A1* | 8/2013 | Kaiser .................. A61B 5/1123 600/595 |
| 2013/0267794 | A1 | 10/2013 | Fernstrom et al. |
| 2014/0073486 | A1 | 3/2014 | Ahmed et al. |
| 2014/0087708 | A1 | 3/2014 | Kalita et al. |
| 2014/0088444 | A1 | 3/2014 | Saalasti et al. |
| 2014/0107932 | A1 | 4/2014 | Luna |
| 2014/0109390 | A1 | 4/2014 | Manning |
| 2014/0121471 | A1 | 5/2014 | Walker |
| 2014/0167973 | A1 | 6/2014 | Letchner et al. |
| 2014/0172238 | A1 | 6/2014 | Craine |
| 2014/0197946 | A1 | 7/2014 | Park et al. |
| 2014/0200906 | A1 | 7/2014 | Bentley et al. |
| 2014/0207264 | A1 | 7/2014 | Quy |
| 2014/0213920 | A1 | 7/2014 | Lee et al. |
| 2014/0221854 | A1 | 8/2014 | Wai |
| 2014/0228649 | A1 | 8/2014 | Rayner et al. |
| 2014/0244071 | A1 | 8/2014 | Czaja et al. |
| 2014/0266789 | A1 | 9/2014 | Matus |
| 2014/0276127 | A1 | 9/2014 | Ferdosi et al. |
| 2014/0278139 | A1 | 9/2014 | Hong et al. |
| 2014/0278229 | A1 | 9/2014 | Hong et al. |
| 2014/0316305 | A1 | 10/2014 | Venkatraman et al. |
| 2014/0348367 | A1 | 11/2014 | Vavrus et al. |
| 2015/0087929 | A1 | 3/2015 | Rapoport et al. |
| 2015/0088006 | A1 | 3/2015 | Rapoport et al. |
| 2015/0100141 | A1 | 4/2015 | Hughes |
| 2015/0119728 | A1 | 4/2015 | Blackadar et al. |
| 2015/0148632 | A1 | 5/2015 | Benaron |
| 2015/0250417 | A1 | 9/2015 | Cheng et al. |
| 2015/0256689 | A1 | 9/2015 | Erkkila et al. |
| 2015/0260514 | A1 | 9/2015 | Menelas et al. |
| 2015/0327804 | A1 | 11/2015 | Lefever et al. |
| 2015/0328523 | A1 | 11/2015 | Heling et al. |
| 2015/0338926 | A1 | 11/2015 | Park et al. |
| 2015/0345985 | A1 | 12/2015 | Fung et al. |
| 2015/0357948 | A1 | 12/2015 | Goldstein |
| 2015/0374240 | A1 | 12/2015 | Lee |
| 2016/0021238 | A1 | 1/2016 | Abramson et al. |
| 2016/0057372 | A1 | 3/2016 | Raghuram et al. |
| 2016/0058302 | A1 | 3/2016 | Raghuram et al. |
| 2016/0058329 | A1 | 3/2016 | Srinivas et al. |
| 2016/0058332 | A1 | 3/2016 | Tan et al. |

(56) References Cited

U.S. PATENT DOCUMENTS

| | | | |
|---|---|---|---|
| 2016/0058333 | A1 | 3/2016 | Arnold et al. |
| 2016/0058356 | A1 | 3/2016 | Raghuram et al. |
| 2016/0058370 | A1 | 3/2016 | Raghuram et al. |
| 2016/0058371 | A1 | 3/2016 | Singh Alvarado et al. |
| 2016/0058372 | A1 | 3/2016 | Raghuram et al. |
| 2016/0059079 | A1 | 3/2016 | Watterson |
| 2016/0084869 | A1 | 3/2016 | Yuen et al. |
| 2016/0166178 | A1 | 6/2016 | Fuss et al. |
| 2016/0170998 | A1 | 6/2016 | Frank et al. |
| 2016/0206248 | A1 | 7/2016 | Sartor |
| 2016/0256058 | A1 | 9/2016 | Pham et al. |
| 2016/0269572 | A1 | 9/2016 | Erkkila et al. |
| 2016/0287177 | A1 | 10/2016 | Huppert et al. |
| 2016/0361020 | A1 | 12/2016 | LeBoeuf et al. |
| 2016/0363449 | A1* | 12/2016 | Metzler .................. A61B 5/11 |
| 2016/0374614 | A1 | 12/2016 | Cavallaro et al. |
| 2017/0007166 | A1 | 1/2017 | Roover et al. |
| 2017/0061817 | A1 | 3/2017 | Mettler |
| 2017/0074897 | A1 | 3/2017 | Mermel et al. |
| 2017/0082649 | A1 | 3/2017 | Tu et al. |
| 2017/0094450 | A1 | 3/2017 | Tu et al. |
| 2017/0111768 | A1 | 4/2017 | Smith et al. |
| 2017/0188893 | A1 | 7/2017 | Venkatraman et al. |
| 2017/0202486 | A1 | 7/2017 | Martikka et al. |
| 2017/0251972 | A1* | 9/2017 | Jayaraman ............ A61B 5/1118 |
| 2017/0259116 | A1 | 9/2017 | Mestas |
| 2017/0273619 | A1 | 9/2017 | Alvarado et al. |
| 2017/0367658 | A1 | 12/2017 | LeBoeuf et al. |
| 2018/0028863 | A1 | 2/2018 | Matsuda |
| 2018/0049694 | A1 | 2/2018 | Alvarado et al. |
| 2018/0050235 | A1 | 2/2018 | Tan et al. |
| 2018/0055375 | A1 | 3/2018 | Martinez et al. |
| 2018/0055439 | A1 | 3/2018 | Pham et al. |
| 2018/0056123 | A1 | 3/2018 | Narasimha Rao et al. |
| 2018/0056128 | A1 | 3/2018 | Narasimha Rao et al. |
| 2018/0056129 | A1 | 3/2018 | Narasimha Rao et al. |

FOREIGN PATENT DOCUMENTS

| | | | |
|---|---|---|---|
| JP | 2010-051333 | A | 3/2010 |
| JP | 2013-039316 | A | 2/2013 |
| JP | 2014-042757 | A | 3/2014 |
| JP | 2016-150018 | A | 8/2016 |
| JP | 2018-000543 | A | 1/2018 |
| JP | 2018-015187 | A | 2/2018 |
| WO | 2010090867 | | 8/2010 |
| WO | 2011/105914 | A1 | 9/2011 |
| WO | 2015/126182 | A1 | 8/2015 |
| WO | 2015/200900 | A1 | 12/2015 |
| WO | 2016/044831 | A1 | 3/2016 |
| WO | 2016/073620 | A1 | 5/2016 |

OTHER PUBLICATIONS

Novatel, "IMU Error and Their Effects", Novatel Application Notes APN-064 Rev A p. 1-6, Feb. 21, 2014.
International Search Report and Written Opinion received for PCT Patent Application No. PCT/US2018/047290, dated Nov. 8, 2018, 14 pages.
KINprof, May 31, 2011, Predictive VO2max tests, Web Video, Retrieved from: https://www.youtube.com/watch?v=_9e3HcY1sm8.
PCT International Application No. PCT/US2017/049693, International Search Report dated Aug. 12, 2017, 3 pages.
Yamaji, et al., "Relationship Between Heart Rate and Relative Oxygen Intake in Male Subjects Aged 10 to 27 Years", J. Human Ergol., 7:29-39, Jan. 27, 1978.
Your Fitness FAQ, Why is it important to warm up and cool down in a workout?, 2012, Web, Retrieved from: http://www.yourfitnessfaq.com/whyisitimportanttowarmupandcooldowninaworkout.html.
Vella et al, Exercise After-Burn: Research Update, 2005, Web, Retrieved from: http://www.unm.edu/~lkravitz/Article%20folder/epocarticle.html.

Song et al., "Training Activity Recognition Systems Online Using Real-Time Crowdsourcing", University of Rochester Computer Science, UbiCom' 12, Sep. 5-8, 2012 (2 pages).
Rowlands et al., "Assessing Sedentary Behavior with the GENEActiv: Introducing the Sedentary Sphere". Medicine and science in sports and exercise 46.6 (2014): 1235-1247.
Hasson et al., "Accuracy of four resting metabolic rate production equations: Effects of sex, body mass index, age, and race/ethnicity", Journal of Science and Medicine in Sport, 2011, vol. 14, p. 344-351.
Lucas et al., "Mechanisms of orthostatic intolerance following very prolonged exercise", 2008, J Appl Physiol, 105: 213-225.
Kunze et al., "Where am i: Recognizing on-body positions of wearable sensors." Location-and context-awareness. Springer Berlin Heidelberg, 2005. 264-275.
Keytel et al., "Prediction of energy expenditure from heart rate monitoring during submaximal exercise", 2005, Journal of Sports Sciences, 23(3):289-97.
Sabatini, Kalman-filter orientation determination using inertial/magnetic sensors: observability analysis and performance evaluation, Sep. 27, 2011, Sensors 2011, 11, 9182-9206.
Jackson et al., "Prediction of functional aerobic capacity without exercise testing", Medicine and Science in Sports and Exercise, 22(6), 863-870, 1990.
Isaacs et al., "Modeling energy expenditure and oxygen consumption in human exposure models: accounting for fatigue and EPOC", 2008, Journal of Exposure Science and Environmental Epidemiology, 18: 289-298.
Human Kinetics, Aerobic Workout Components, 2011, Web, Retrieved from: http://www.humankinetics.com/excerpts/excerpts/aerobicworkoutcomponentsexcerpt.
Gao et al., "Evaluation of accelerometer based multi-sensor versus single-sensor activity recognition systems." Medical engineering & physics 36.6 (2014): 779-785.
Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.
Chu, "In-Vehicle Driver Detection Using Mobile Phone Sensors", Submitted for Graduation with departmental . . . Distinction in Electrical and Computer Engineering, Apr. 20, 2011, pp. 1-21.
Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.
Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).
Bruce, R.A. et al., "Exercising testing in adult normal subjects and cardiac patients," Pediatrics, vol. 32, No. Suppl., pp. 742-756 (Oct. 1963).
Bruce, R.A. et al., "Maximal oxygen intake and nomographic assessment of functional aerobic impairment in cardiovascular disease," American Heart Journal, vol. 85, Issue 4, pp. 546-562 (Apr. 1973).
Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages. (2003).
Cavanagh, P.R. et al., "The effect of stride length variation on oxygen uptake during distance running," Medicine and Science in Sports and Exercise, vol. 14, No. 1, pp. 30-35 (1982).
Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

(56) References Cited

OTHER PUBLICATIONS

Fox, S.M. et al., "Physical Activity and the Prevention of Coronary Heart Disease," Bull. N.Y. Acad. Med., vol. 44, No. 8, pp. 950-967 (Aug. 1968).

Glass, S., et al., "ACSM's Metabolic Calculations Handbook," Lippincott Williams & Wilkins, 124 pages (2007).

Lavie, C.J. et al., "Impact of cardiorespiratory fitness on the obesity paradox in patients with heart failure," Mayo Clinic Proceedings, vol. 88, No. 3, pp. 251-258 (Mar. 2013).

Margaria, R. et al., "Energy cost of running," Journal of Applied Physiology, vol. 18, No. 2, pp. 367-370 (Mar. 1, 1963).

McArdle, W.D. et al., "Exercise Physiology: Nutrition, Energy and Human Performance," Seventh Edition, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for Anerobic and Aerobic Power; (2010).

Myers, J. et al., "Exercise Capacity and Mortality Among Men Referred for Exercise Testing," The New England Journal of Medicine, vol. 346, No. 11, pp. 793-801 (Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Rapoport, Benjamin I., "Metabolic Factors Limiting Performance in Marathon Runners," PLoS Computational Biology, vol. 6, Issue 10, 13 pages (Oct. 2010).

Tanaka, H. et al., "Age-predicted maximal heart rate revisited," Journal of the American College of Cardiology, vol. 37, Issue 1, pp. 153-156 (Jan. 2001).

Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).

Kyle, Chester R., "Reduction of Wind Resistance and Power Output of Racing Cyclists and Runners Travelling in Groups". Ergonomics, vol. 22, No. 4, 1979, pp. 387-397.

\* cited by examiner

| PATTERN | AXIS | RH PUSH | RH RETURN | LH PUSH | LH RETURN |
|---|---|---|---|---|---|
| SC | X | + - - | - + (-) | - + + | + - (+) |
| SC | Y | - | (-) + - | - | (-) + - |
| SC | Z | 0 - | - /+ | 0 - | - /+ |
| SLOP | X | + - - | + + - | - + + | - - + |
| SLOP | Y | - | (-) + - | - | (-) + - |
| SLOP | Z | 0 - | - /+ | 0 - | - /+ |

*FIG. 31*

|  | FLAT/UNKNOWN | UPHILL | DOWNHILL |
|---|---|---|---|
| GPS/ALTIMETER AVAILABLE | FLAT GPS SPEED MODEL | GRADE FROM GPS/ALTIMETER MODEL | ENERGY-BASED MODEL |
| GPS/ALTIMETER UNAVAILABLE | ENERGY-BASED MODEL | ENERGY-BASED MODEL W/ ACCELEROMETER RAMP CORRECTION | ENERGY-BASED MODEL |
| GPS SPEED < 0.3 m/s | BASAL METs | BASAL METs | BASAL METs |
| 0.3 m/s < GPS SPEED < 0.5 m/s | MINIMUM MOVING METs | MINIMUM MOVING METs | MINIMUM MOVING METs |

*FIG. 45*

| DATA SOURCE | METRIC | UPHILL | DOWNHILL |
|---|---|---|---|
| GPS/ALTIMETER ONLY | deltaH > THRESHOLD | X |  |
|  | deltaH < THRESHOLD |  | X |
| ACCELEROMETER + GPS | GPS SPEED SLOW OR REDUCING AND PUSH COUNT OR ENERGY < THRESHOLD | X |  |
|  | GPS SPEED FAST OR INCREASING AND PUSH COUNT OR ENERGY > THRESHOLD |  | X |

*FIG. 46*

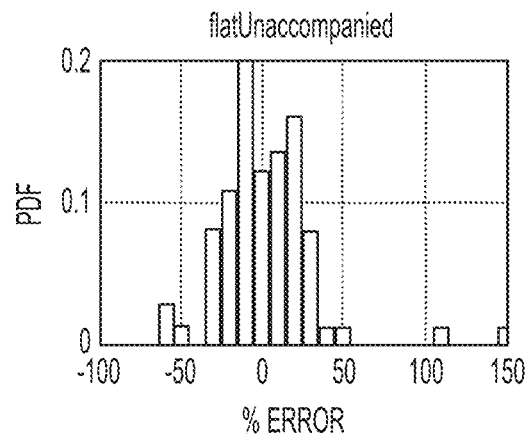
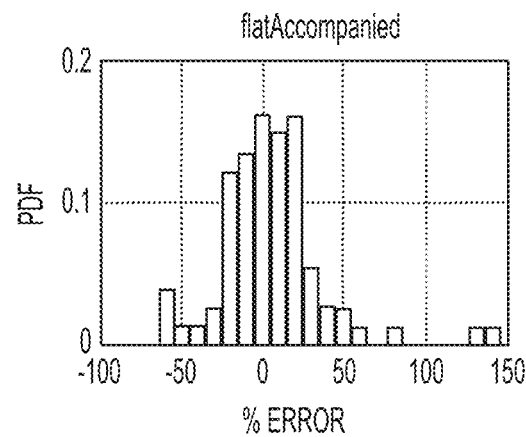
FIG. 50A  FIG. 50B
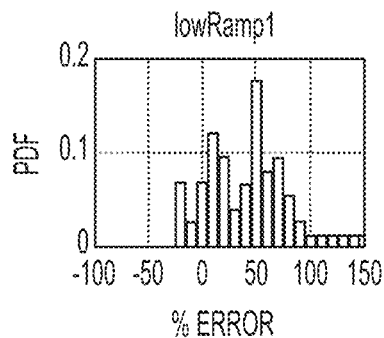
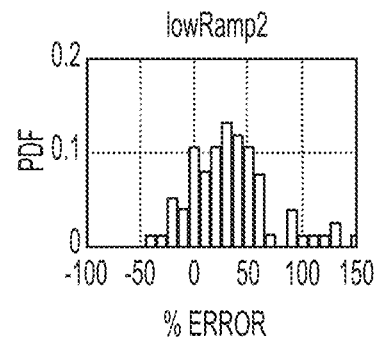
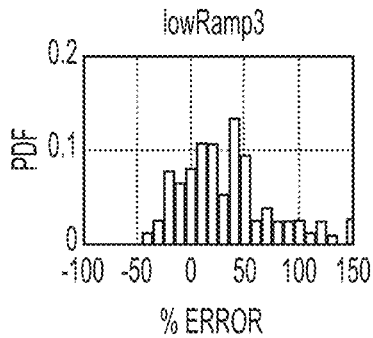
FIG. 50C  FIG. 50D  FIG. 50E
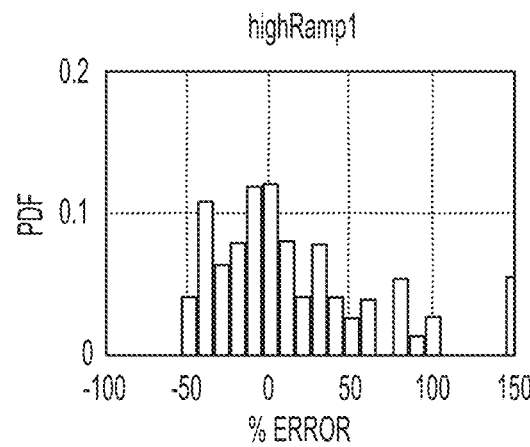
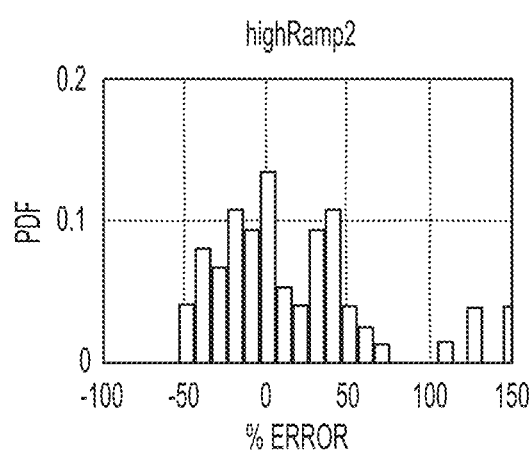
FIG. 50F  FIG. 50G

DETECTING ACTIVITY BY A WHEELCHAIR USER

CROSS-REFERENCE TO RELATED APPLICATION

This application claims priority to and the benefit of U.S. Provisional Application No. 62/346,667 filed on Jun. 7, 2016, U.S. Provisional Application No. 62/346,727 filed on Jun. 7, 2016, U.S. Provisional Application No. 62/346,795 filed on Jun. 7, 2016, U.S. Provisional Application No. 62/381,678 filed on Aug. 31, 2016, and U.S. Provisional Application No. 62/381,878 filed on Aug. 31, 2016, the disclosures of which are incorporated herein by reference in their entireties.

FIELD

The present disclosure relates generally to wearable devices (or "user devices") used in conjunction with a person in a wheelchair.

BACKGROUND

Various human activities, such as activities by a wheelchair user, involve repetitive motions of the arms. For example, pushing oneself in a wheelchair, rowing, push-ups and pull-ups, and assembly-line tasks may all involve repetition of a sequence of motions using the hands, arms, and wrists. A wearable device may be worn on the hand, wrist, or arm of the person performing the activity. It may be desirable to track activity by a wheelchair user for health, safety, or productivity reasons.

SUMMARY

According to one aspect of the present disclosure, a method for tracking activity by a wheelchair user can include collecting motion data of a user device located on an appendage of the user, detecting by a processor circuit that one or more activities by the wheelchair user occurred based on the motion data, estimating by a processor circuit an energy expenditure by the user based on the one or more activities, and outputting the estimated energy expenditure by a processor circuit. In some embodiments, the motion sensor can include an accelerometer, a gyroscope, a magnetometer, or a combination thereof.

In some embodiments, the method can include tracking pushes by the wheelchair user. In some embodiments, the method can include determining a pose angle and a calculated energy based on the motion data. In some embodiments, the method can include detecting a push occurred based on a determined pose angle and a calculated energy. In some embodiments, the method can include comparing by a processor circuit the determined pose angle with a pose angle threshold, comparing by a processor circuit the calculated energy with an energy threshold, and determining by a processor circuit a push occurred if the determined pose angle is below the pose angle threshold and the calculated energy is above the energy threshold.

In some embodiments, the method can include storing pose angles and calculated energies for the wheelchair user, updating by a processor circuit the pose angle threshold using the stored pose angle, and updating by a processor circuit the energy threshold using the stored calculated energies. In some embodiments, the method can include calculating by a processor circuit a current push rate for the user, determining by a processor circuit if the current push rate is consistent with previous push rates, and storing the determined pose angle and calculated energy if the current push rate is consistent with previous push rates.

In some embodiments, the method can include determining by a processor circuit a current speed for the user using a Global Positioning System (GPS) sensor and storing the determined pose angle and calculated energy if the user's current speed is greater than or equal to a minimum speed threshold. In some embodiments, the method can include calculating a candidate pose angle threshold as a percentile of stored pose angle and calculating a candidate energy threshold as a percentile of stored calculated energies. In some embodiments, the method can include calculating a new pose angle threshold using the candidate pose angle threshold and a first low-pass filter, and calculating a new energy threshold using the candidate energy threshold and a second low-pass filter.

In some embodiments, the method can include selecting a dominant motion sensor axis based on a calculated motion energy per motion sensor axis. In some embodiments, the method can include calculating by a processor circuit a motion energy for each motion sensor axis and selecting by a processor circuit an motion sensor axis with a most energy as a dominant motion sensor axis.

In some embodiments, the method can include performing by a processor circuit a frequency domain transformation of the collected motion data for the dominant motion sensor axis and determining by a processor circuit a fundamental push frequency based on the frequency domain transformed data. In some embodiments, the frequency domain transformation can include a fast Fourier transform (FFT) operation. In some embodiments, the method can include determining by a processor circuit a FFT peak of a lowest frequency that rises above a pre-determined threshold level of energy and selecting by a processor circuit the lowest frequency as a fundamental frequency of pushing.

In some embodiments, the method can include adjusting an intelligent filter to pass motion sensor signals within a frequency band corresponding to the fundamental push frequency and to reduce motion sensor signals within a frequency band corresponding to harmonics of the fundamental push frequency. In some embodiments, the intelligent filter can include a low-pass filter with adjustable passband width. In some embodiments, the intelligent filter can include a bank of low-pass filters with increasing passband widths. In some embodiments, the intelligent filter can include an adjustable bandpass filter with adjustable passband cutoff frequencies and widths.

In some embodiments, the method can include filtering by a processor circuit the collected motion data to produce filtered motion data and determining a push count based on zero-crossings of the filtered motion data. In some embodiments, the method can include detecting by a processor circuit one or more zero-crossings of the filtered motion data in one direction and determining by a processor circuit a push count equal to the number of zero-crossings.

In some embodiments, the method can include cross-checking by a processor circuit the determined push count with motion data from a different motion sensor axis.

According to yet another aspect of the present disclosure, the method can include detecting when a wheelchair user is traveling on a ramp. The method can include collecting motion data of a user device located on an appendage of the user, determining a ramp classification by a processor circuit, and filtering by a processor circuit the determined ramp classification using a filter.

In some embodiments, a ramp classification can be determined based on a push rate, a first push rate threshold, an energy component of the collected motion data, and at least one of a first energy threshold, a second energy threshold, a pose angle, a pose angle threshold, and a second push rate threshold.

In some embodiments, the method can include comparing by a processor circuit the push rate with the first push rate threshold, and at least one of: comparing by a processor circuit the energy component of the collected motion data with the first energy threshold; comparing by a processor circuit the pose angle with the pose angle threshold; comparing by a processor circuit the energy component of the collected motion data with the second energy threshold; and comparing by a processor circuit the push rate with the second push rate threshold.

In some embodiments, the method can include obtaining per-user thresholds and adjusting by a processor circuit at least one of the first and second push rate thresholds, the first and second energy thresholds, and the pose angle threshold using the per-user thresholds.

In some embodiments, the filter can include a windowing filter. In some embodiments, the windowing filter can include an odd number of points in the window. In one embodiment, the windowing filter can include a three-point window.

In some embodiments, the method can include collecting elevation information by an elevation detection module of the user device and determining by a processor circuit the ramp classification based on the collected elevation information.

In some embodiments, the method can include measuring the user's heart rate by a heart rate monitor of the user device and determining by a processor circuit the ramp classification based on the measured heart rate.

According to another aspect of the present disclosure, the method can include detecting the type of stroke being employed by a wheelchair user. The method can include measuring X axis and Y axis accelerometer data from an accelerometer located on an arm of the user, and detecting a Y axis accelerometer peak corresponding to a push phase. The method can determine adjacent zero crossing to the Y axis accelerometer peak to determine the start and end of the push phase and a return phase. The method can determine a length of the push phase, detect X peaks in X axis accelerometer data during the return phase, and detect Y peaks in Y axis accelerometer data during the return phase. The method can determine signs for the X peaks and the Y peaks, an ordered sequence of the determined X signs, and an ordered sequence of the determined Y signs. In addition, the method can determine stroke type based on the sequence of X signs and the sequence of Y signs, and apply one of the determined stroke type and the determined push phase length in a calorie expenditure tracking system.

According to yet another aspect of the present disclosure, the method can include estimating caloric expenditure by a wheelchair user. The method can include measuring at least one of X accelerometer data, Y accelerometer data, Z accelerometer data, X rotational data, Y rotational data, Z rotational data, barometer data, altimeter data, GPS position data, GPS speed data, GPS altitude data, and heart rate data and receiving user input regarding at least one of fitness level, age, weight, injury type, and mobility level. The method can determine an estimated speed based on the measured data and determines an estimated MET value based on the estimated speed, as well as determining a ramp state based on the measured data. The method can refine the estimated MET value based on the determined ramp state and determines an energy expenditure estimate based on the estimated MET value. In addition, the method may include determining a physiological efficiency estimate based on the user input and refining the physiological efficiency estimate based on the measured data, and then refining the energy expenditure estimate using the physiological efficiency estimate. The refined energy expenditure estimate can be applied in a caloric expenditure tracking system.

According to yet another aspect of the present disclosure, a system for tracking activity by a wheelchair user can include a motion sensor located on an appendage of the user and configured to collect motion data. The system can include a processor circuit coupled to the motion sensor and configured to execute instructions causing a processor circuit to collect motion data of a user device located on an appendage of the user, detect one or more activities by the wheelchair user occurred based on the motion data, calculate an energy expenditure by the user based detecting that the one or more activities by the wheelchair user occurred, and output the energy expenditure estimation.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

FIG. 31 illustrates the characteristic signs of acceleration in the X, Y, and Z axes for right-handed or left-handed push and return phases for the semicircular and single loop patterns.

FIG. 45 illustrates a decision matrix for data fusion.

FIG. 46 illustrates a decision matrix for grade determination.

FIGS. 50A-50G illustrate the probability density function (PDF) of errors in the speed estimate for various types of surfaces.

DETAILED DESCRIPTION

The present disclosure describes a wearable device that may be configured to detect the number and timing of instances of a repetitive activity. In one embodiment, this activity is "pushing" a wheelchair.

While this disclosure focuses on the sequence of motions involved in pushing oneself in a wheelchair, the concepts and techniques described herein are equally applicable to other tasks involving repetitive hand and arm motions. For example, the stroke count and timing in rowing may be detected.

Figure 1:
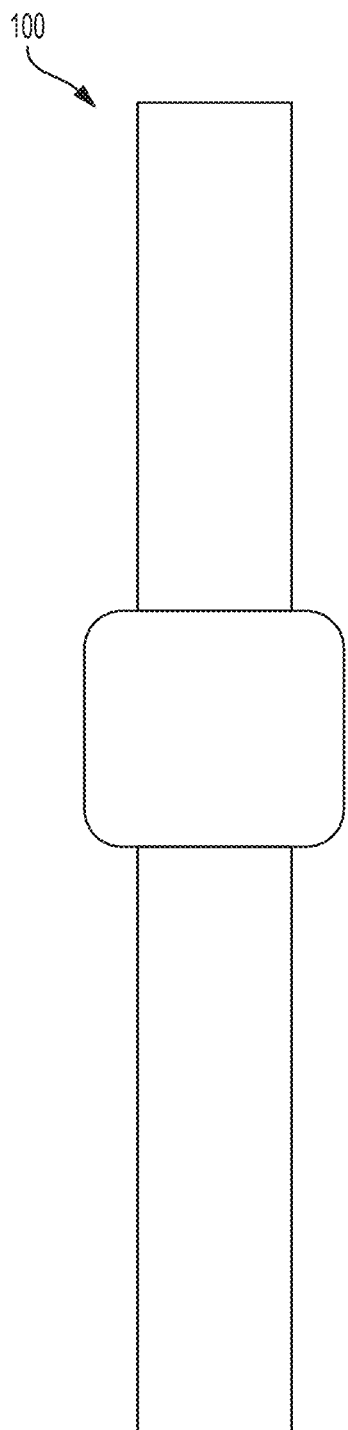
FIG. 1 shows an example of a wearable device 100 in accordance with an embodiment of the present disclosure.

FIG. 1 shows an example of a wearable device 100 in accordance with an embodiment of the present disclosure. In some embodiments, the wearable device 100 may be any suitable wearable device, such as a watch configured to be worn around an individual's wrist. As described in more detail below, the wearable device 100 may be calibrated to attributes of the individual (e.g., the user's particular style of pushing the chair such as a typical stroke type.)

Figure 2:
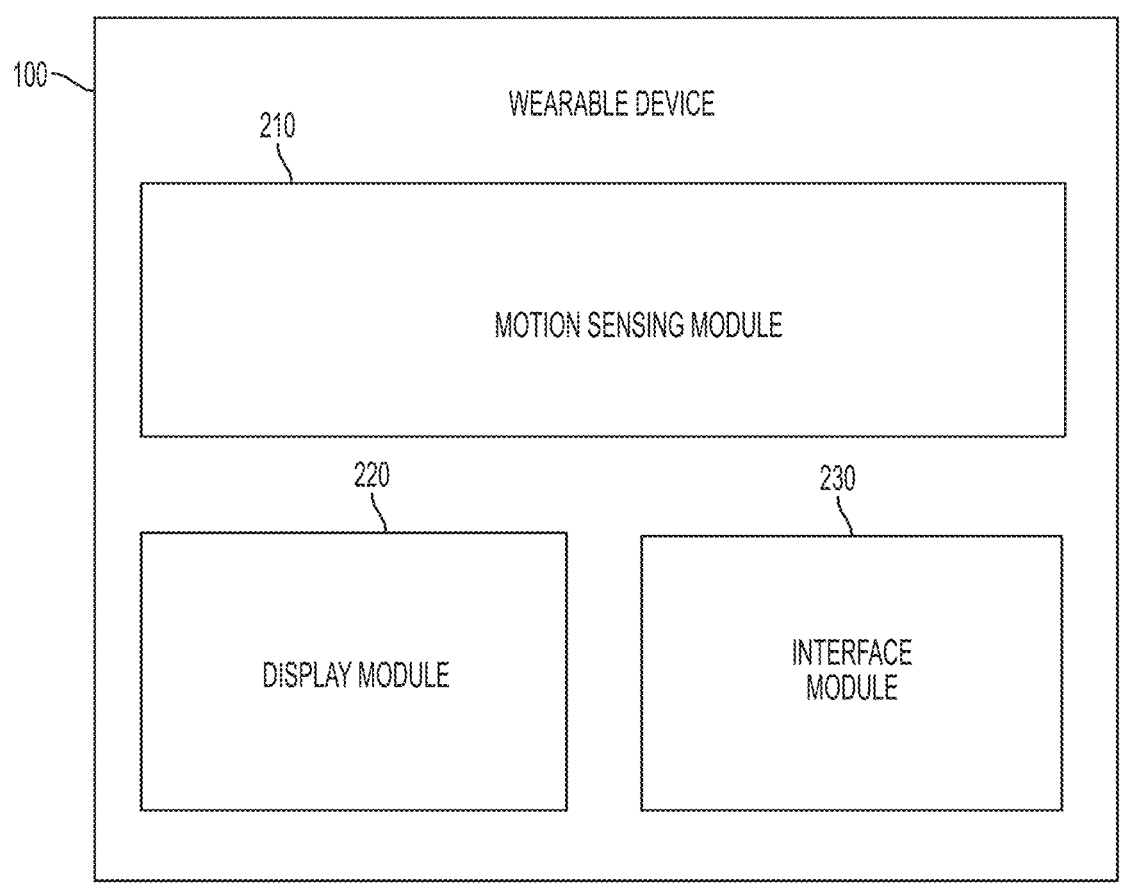
FIG. 2 depicts a block diagram of example components that may be found within the wearable device 100 in accordance with an embodiment of the present disclosure.

FIG. 2 depicts a block diagram of example components that may be found within the wearable device 100 in accordance with an embodiment of the present disclosure. These components may include a motion sensing module 210, a display module 220, and an interface module 230.

The wearable device 100 may include the motion sensing module 210. The motion sensing module 210 may include one or more motion sensors, such as an accelerometer, a gyroscope, or a magnetometer. In some embodiments, the accelerometer may be a three-axis, microelectromechanical system (MEMS) accelerometer, and the gyroscope may be a three-axis MEMS gyroscope, and the magnetometer may be a three-axis magnetometer. A microprocessor (not shown) or motion coprocessor (not shown) of the wearable device 100 may receive motion information from the motion sensors of the motion sensing module 210 to track acceleration, rotation, position, or orientation information of the wearable device 100 in six degrees of freedom through three-dimensional space.

The wearable device 100 may also include the display module 220. Display module 220 may be a screen, such as a crystalline (e.g., sapphire) or glass touchscreen, configured to provide output to the user as well as receive input from the user via touch. For example, display 220 may be configured to display a current heart rate or a daily average energy expenditure. Display module 220 may receive input from the user to select, for example, which information should be displayed, or whether the user is beginning a physical activity (e.g., starting a session) or ending a physical activity (e.g., ending a session), such as a running session or a cycling session. In some embodiments, the wearable device 100 may present output to the user in other ways, such as by producing sound with a speaker (not shown), and the wearable device 100 may receive input from the user in other ways, such as by receiving voice commands via a microphone (not shown).

In some embodiments, the wearable device 100 may communicate with external devices via interface module 230, including a configuration to present output to a user or receive input from a user. Interface module 230 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 230 may include wired interfaces, such as a headphone jack or bus connector (e.g., Lightning, Thunderbolt, USB, etc.).

The wearable device 100 may be configured to communicate with a companion device 300 (FIG. 3), such as a smartphone, as described in more detail herein. In some embodiments, the wearable device 100 may be configured to communicate with other external devices, such as a notebook or desktop computer, tablet, headphones, Bluetooth headset, etc.

The modules described above are examples, and embodiments of the wearable device 100 may include other modules not shown. For example, the wearable device 100 may include one or more microprocessors (not shown) for processing heart rate data, motion data, other information in the wearable device 100, or executing instructions for firmware or apps stored in a non-transitory processor-readable medium such as a memory module (not shown). Additionally, some embodiments of the wearable device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
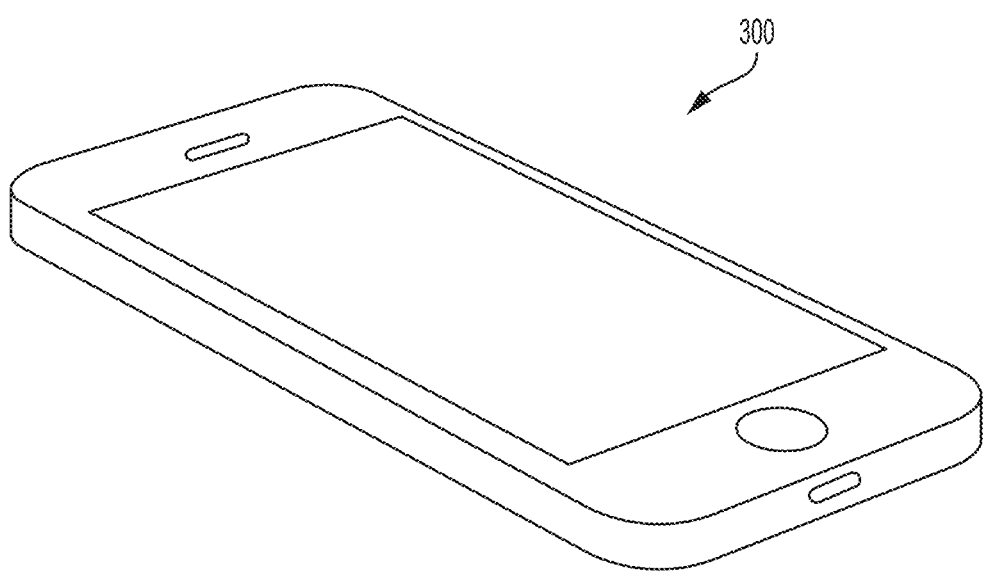
FIG. 3 shows an example of a companion device 300 in accordance with an embodiment of the present disclosure.

FIG. 3 shows an example of a companion device 300 in accordance with an embodiment of the present disclosure. The wearable device 100 may be configured to communicate with the companion device 300 via a wired or wireless communication channel (e.g., Bluetooth, Wi-Fi, etc.). In some embodiments, the companion device 300 may be a smartphone, tablet computer, or similar portable computing device. The companion device 300 may be carried by the user, stored in the user's pocket, strapped to the user's arm with an armband or similar device, placed in a mounting device, or otherwise positioned within communicable range of the wearable device 100.

The companion device 300 may include a variety of sensors, such as location and motion sensors (not shown). When the companion device 300 may be optionally available for communication with the wearable device 100, the wearable device 100 may receive additional data from the companion device 300 to improve or supplement its calibration or calorimetry processes. For example, in some embodiments, the wearable device 100 may not include a GPS sensor as opposed to an alternative embodiment in which the wearable device 100 may include a GPS sensor. In the case where the wearable device 100 may not include a GPS sensor, a GPS sensor of the companion device 300 may collect GPS location information, and the wearable device 100 may receive the GPS location information via interface module 230 (FIG. 2) from the companion device 300.

In another example, the wearable device 100 may not include an altimeter or barometer, as opposed to an alternative embodiment in which the wearable device 100 may include an altimeter or barometer. In the case where the wearable device 100 may not include an altimeter or barometer, an altimeter or barometer of the companion device 300 may collect altitude or relative altitude information, and the wearable device 100 may receive the altitude or relative altitude information via interface module 230 (FIG. 2) from the companion device 300.

In another example, the wearable device 100 may receive motion data from the companion device 300. The wearable device 100 may compare the motion data from the companion device 300 with motion data from the motion sensing module 210 of the wearable device 100. Motion data such as accelerometer or gyroscope data may be filtered (e.g. by a high-pass, low-pass, band-pass, or band-stop filter) in order to improve the quality of motion data. For example, a low-pass filter may be used to remove vibrations such as those caused by a surface a wheelchair is rolling across.

The wearable device may use motion data to predict a user's activity. Examples of activities may include, but are not limited to, pushing a wheelchair, running, cycling, rowing, etc. The wearable device may also interpret the motion data to map aspects of the activity such as push or stroke count. The wearable device may use a variety of motion data, including, in some embodiments, motion data from a companion device. The wearable device may use a variety of heuristics, algorithms, or other techniques to predict the user's activity.

In one embodiment of the disclosure, a method is presented to estimate the push count for wheel chair users using accelerometers in a wrist-worn wearable device. Other motion sensors can also be used. The terms "stroke" and "push" are used interchangeably herein with respect to a wheelchair user.

Figure 4A:
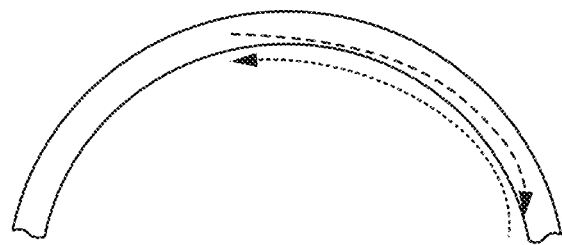
FIGS. 4A-4D illustrate four typical patterns of motion for a wheel chair user pushing their wheelchair.
Figure 4B:
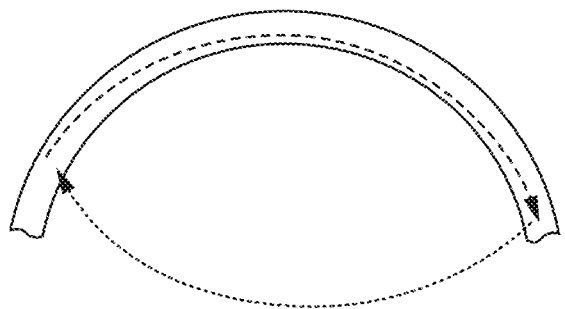
Figure 4C:
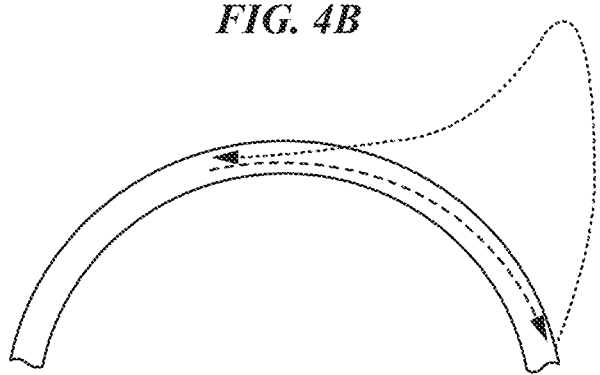
Figure 4D:
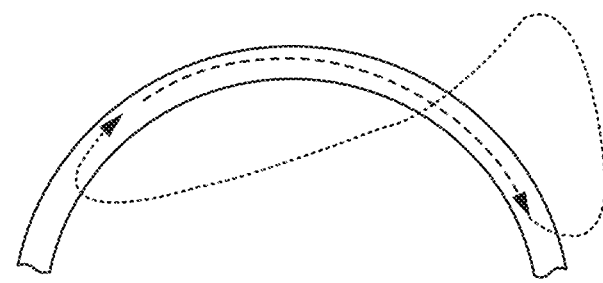
Figure 5A:
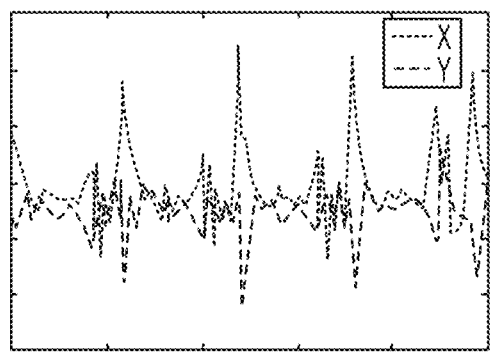
FIGS. 5A-5D illustrate X and Y motion data taken during a sequence of pushes using each of the four patterns illustrated in FIGS. 4A-4D, according to aspects of the present disclosure.
Figure 5B:
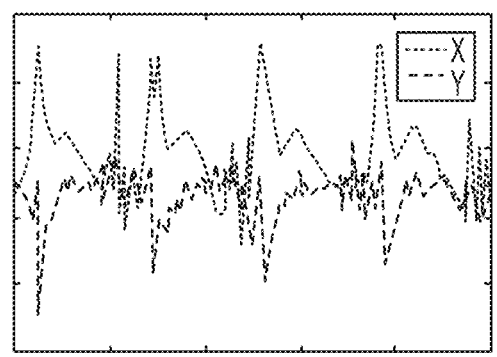
Figure 5C:
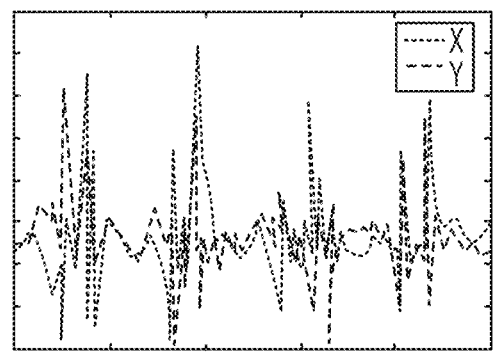
Figure 5D:
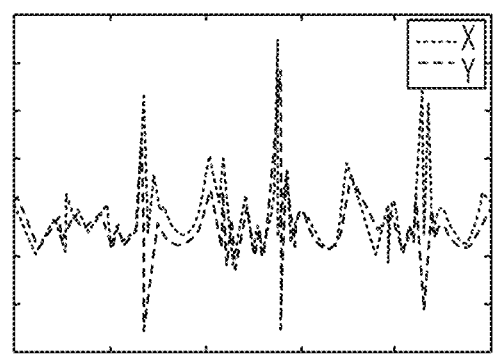

FIGS. 4A-4D illustrate four typical patterns of motion for a wheel chair user pushing their wheelchair. FIG. 4A illustrates the arc pattern, using a short arc motion, which a wheel chair user might use for smaller motions or to hold space when the surface is not level. FIG. 4B illustrates the semi-circular pattern, which might be used when somewhat more motion is required, or by users who find it more comfortable than an arc pattern. FIG. 4C illustrates a single loop pattern and FIG. 4D illustrates a double loop pattern, both of which are typically used for more powerful movements. In each pattern, the dashed line represents the period of time during which the user's hand is on the rim of the wheelchair applying force to it, while the dotted line represents the path the user's hand takes in resetting to a starting position. Arrows indicate the direction of travel of the hand. The two solid arcs represent the pushrim and wheel rim for a wheel of a wheelchair. In each of FIGS. 4A-4D, the wheelchair is being propelled towards the right of the figure.

FIGS. 5A-5D illustrate X and Y motion data taken during a sequence of pushes using each of the four patterns illustrated in FIGS. 4A-4D. In each figure, the solid line indicates X axis motion data, while the dashed line indicates Y axis motion data. As the accelerometer axes are based on the positioning of the wearable device, which may rotate with the user's wrist during pushing a wheelchair, they do not align perfectly to the wheelchair axes throughout the pushing motion.

For example, if a user is sitting upright and pushes the wheels at their top portion using a short arc pattern, then the Y axis aligns primarily to the direction of forward motion, with the X axis aligned in the direction of gravity and the Z axis aligned with the axle of the wheel. In another case, if a user leans forward and pushes the wheels on the front of the wheel using a single loop pattern, then the X axis is aligned with the direction of forward motion, with the Y axis perpendicular to that direction and the Z axis aligned with the axle of the wheel.

The angle of a user's arm with respect to the horizon can be estimated using known techniques, such as those disclosed in U.S. patent application Ser. No. 14/501,930, entitled "Method and System to estimate day-long calorie expenditure based on posture," which is hereby incorporated by reference in its entirety.

The X and Y motion data can be used to detect pushes by a wheelchair user. However, simple methods such as counting peaks in the motion data do not function well. Some pushes do not generate a single strong peak, while others may generate multiple peaks. Peak detectors will thus miss some pushes and double or triple count other pushes. In order to avoid this, the data needs to be appropriately filtered. However, the filter should maintain the stroke signals while removing noise from the motion data.

Figure 6:
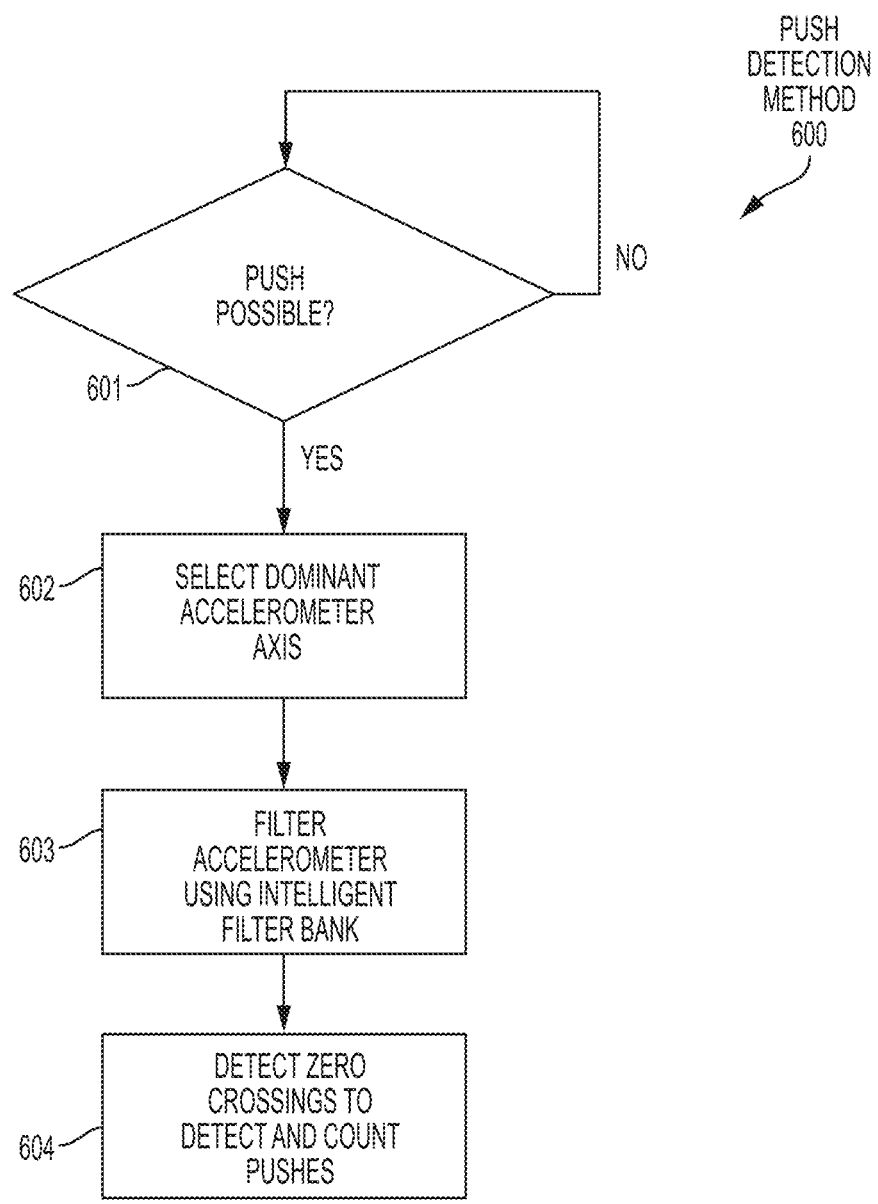
FIG. 6 illustrates a method of detecting and counting pushes by a wheelchair user, according to aspects of the present disclosure.

FIG. 6 illustrates a method 600 of detecting and counting pushes by a wheelchair user. In step 601, motion data is collected and possible push detection is performed. In the present disclosure, a push is said to be "possible" if one or more conditions are detected that increase the likelihood that a push is occurring. Thus, step 601 may determine probabilistically or heuristically whether pushing is occurring at the current time. If pushing is possible, the push counter operations of steps 602, 603, and 604 are used. Following the push detector, the dominant axis may be selected in step 602, which maximizes the input signal-to-noise ratio to the push counter. In step 603, an intelligent filter bank is used to filter accelerometer signals, such as the accelerometer signal for the dominant axis. Other motion sensor signals can also be collected and filtered. In step 604, a zero-crossing counter is used to detect and count the number of pushes.

Figure 7:
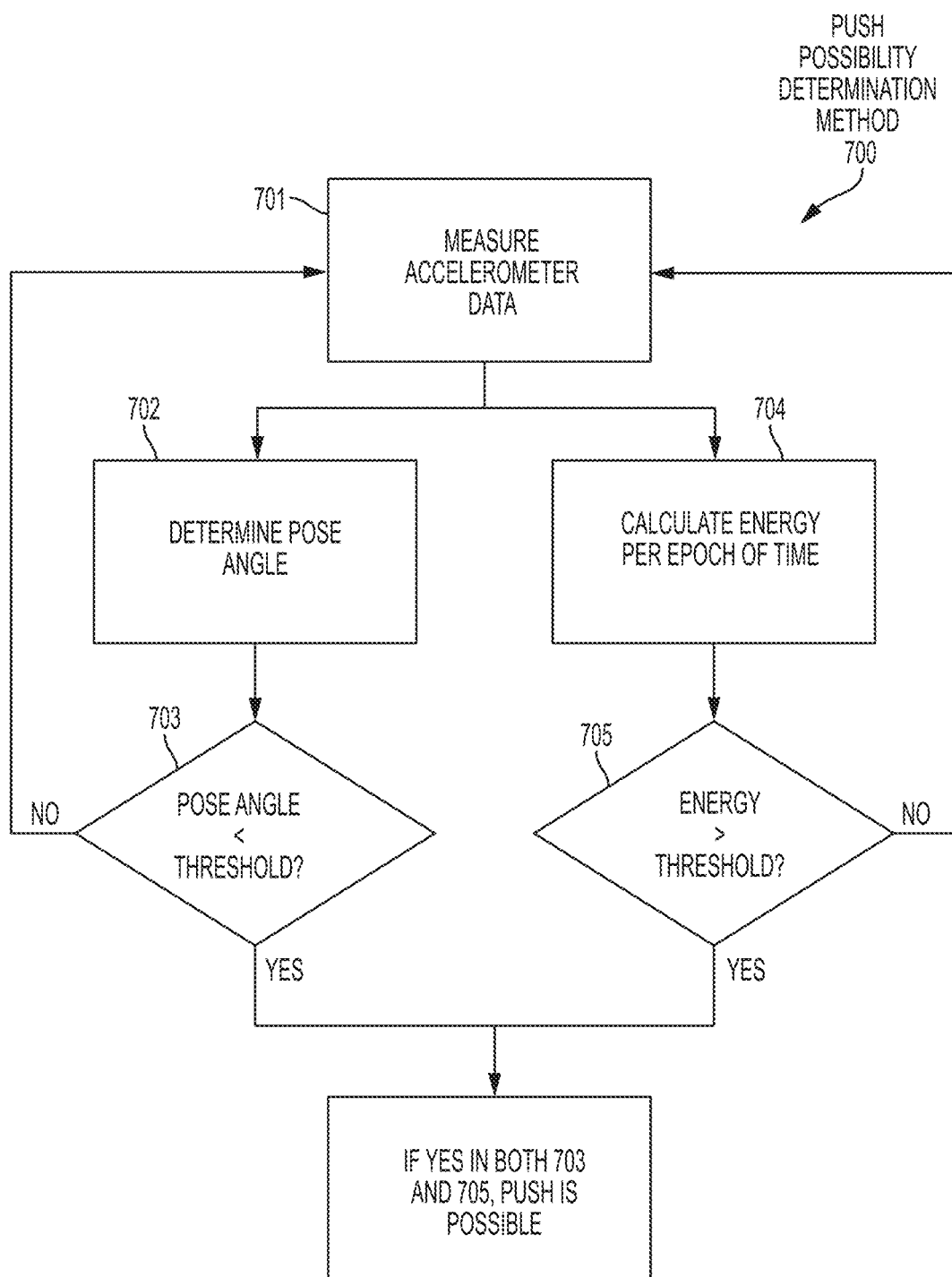
FIG. 7 illustrates a method of detecting the likelihood that a push may be occurring, according to aspects of the present disclosure.

FIG. 7 illustrates a method 700 of detecting the likelihood that a push may be occurring, as in step 601 of FIG. 6. In step 701, motion data is collected from an accelerometer or other motion sensor located on an appendage of the user, such as the user's wrist or arm. In an exemplary embodiment, the accelerometer or other motion sensor is located on the user's wrist. In step 702, the pose angle of the user's arm is determined. Pose angle is defined as the angle between the forearm and the horizon, and may be computed in real-time using a 50 Hz accelerometer signal as described in U.S. patent application Ser. No. 14/501,930, entitled "Method and System to estimate day-long calorie expenditure based on posture." Typically, the pose angle is negative when pushing because the user's forearm must be below the horizon to push effectively. The determined pose angle is then compared to a pose angle threshold in step 703. In addition to pose angle detection, during a push total energy is typically high. In step 704, the energy per epoch of time is calculated. In some embodiments, the calculated energy is based on a time epoch of about 5.12 seconds. In step 705, the calculated energy is compared to an energy threshold. If the determined pose angle is less than the pose angle threshold and the calculated energy is greater than the energy threshold, a push may be occurring. By only operating the push counter when the push detection method 700 indicates a push may be occurring, erroneous push detections and spurious input affecting the push counter filter can be avoided, thereby reducing the number of false positive detections.

In some embodiments, dominant axis selection as in step 602 of FIG. 6 is performed when the push detection method of FIG. 7 indicates a push may be occurring. Dominant axis selection ensures that the accelerometer axis with the strongest signal (e.g., the X-axis) is the only axis filtered. Dominant axis selection may be required because in many cases there is more motion energy in one axis than the others. For example, an upright user pushing the wheels in a short arc pattern will have more energy in the Y-axis, while a user leaning forward and pushing in a single loop pattern will have more energy in the X-axis. By selecting the dominant axis for filtering, the input signal-to-noise ratio to the push counter can be maximized, ensuring accurate push counts. To select a dominant axis, the motion energy for each axis is calculated and the axis with the most energy is selected. In some embodiments, hysteresis is employed to prevent rapid switching between axes.

Figure 8:
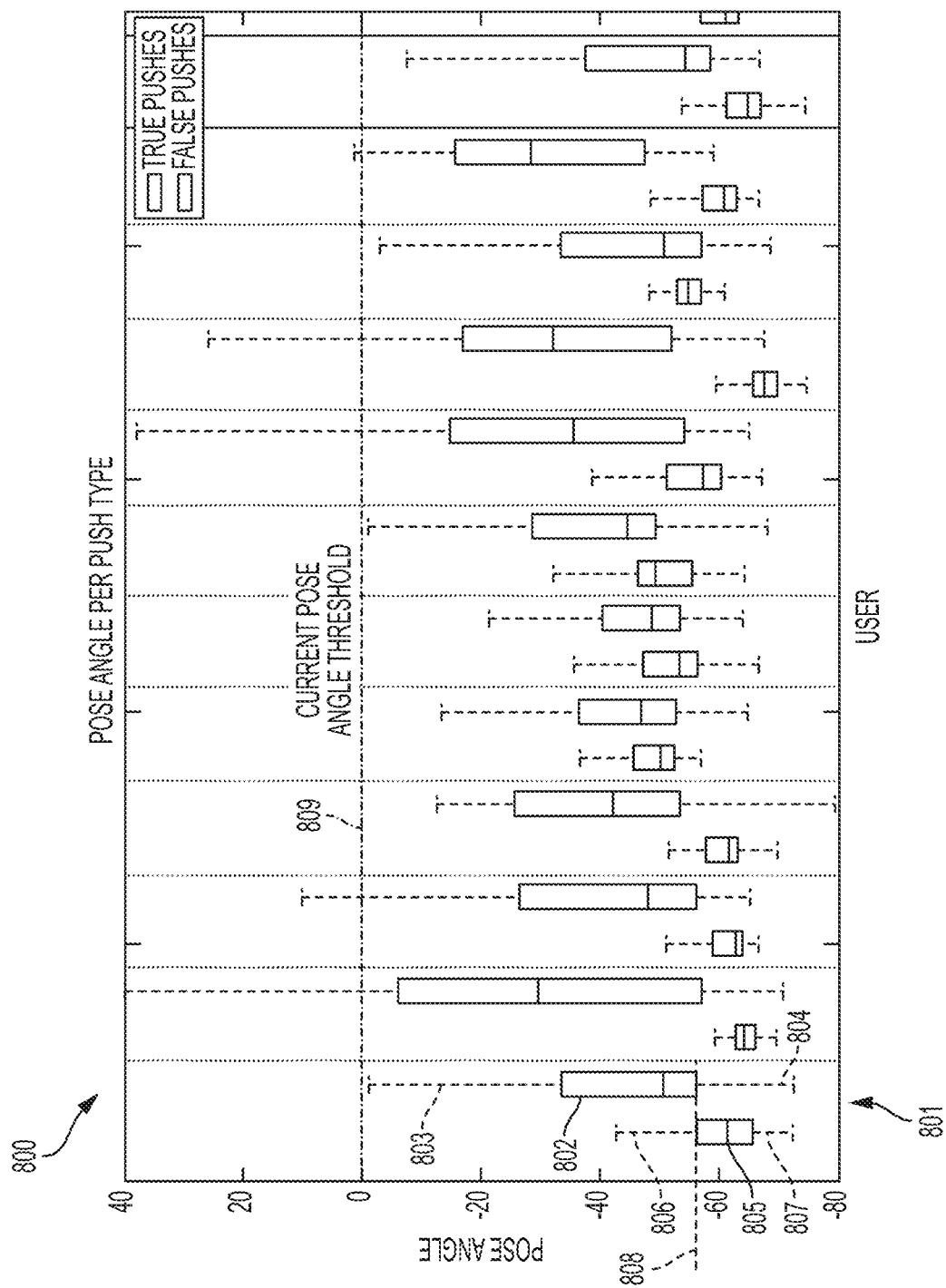
FIG. 8 is a graph illustrating true and false pushes for multiple different wheelchair users.
Figure 9:
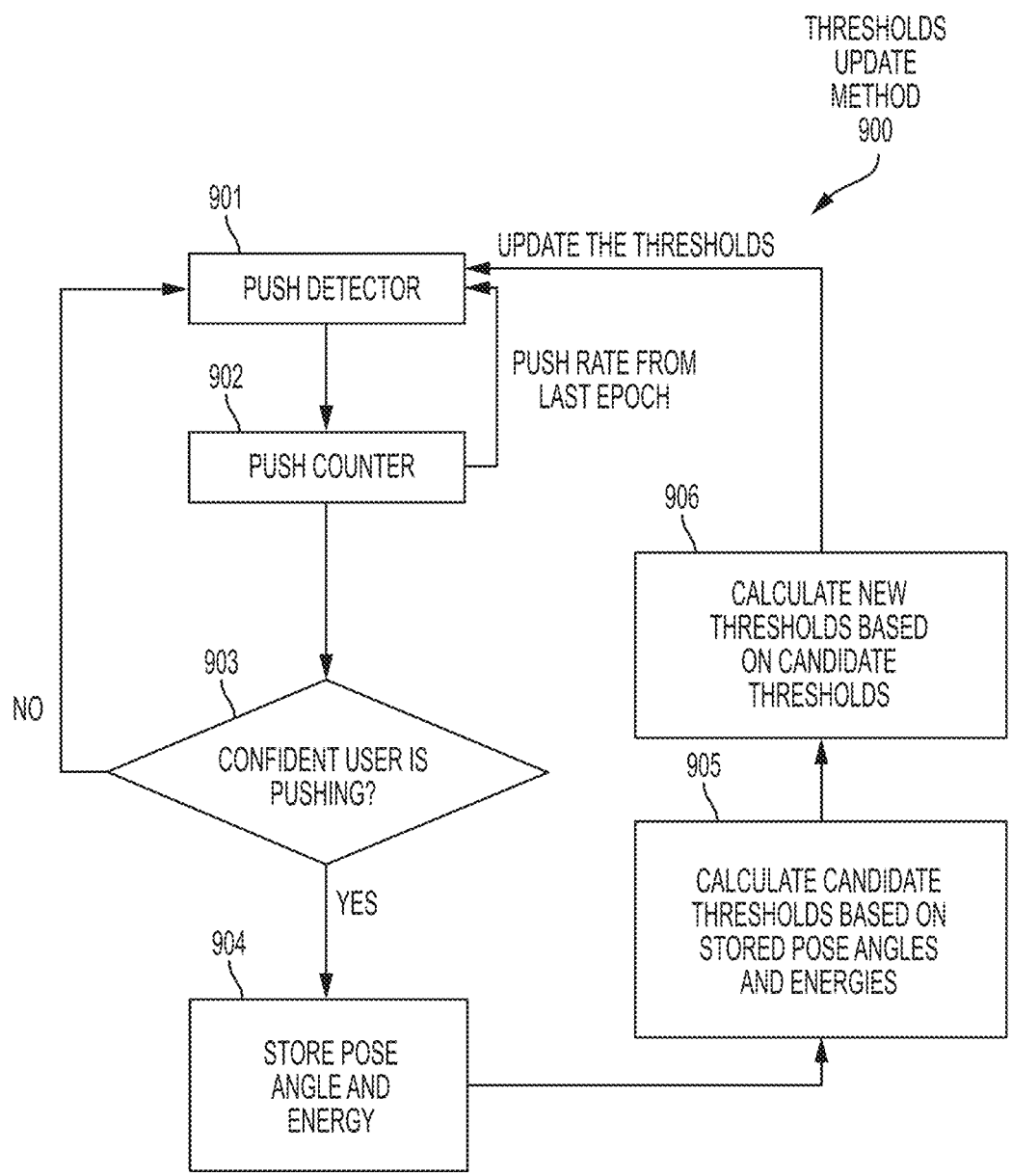
FIG. 9 illustrates a method for adaptively determining pose angle and energy thresholds for a wheelchair user, according to some embodiments of the present disclosure.

Referring to FIGS. 8 and 9, different users may exhibit different pose angles and/or expend different amounts of energy per epoch time when pushing a wheelchair. Using the same pose angle threshold and/or energy threshold for all users can result in false push detections for some users, and missed push detections for other users. Accordingly, in some embodiments of the present disclosure, the pose angle threshold and/or energy threshold may be determined using an adaptive process that accommodates user differences. A push detection method (e.g., method 700 of FIG. 7) can utilize the adaptive, per-user thresholds to improve the accuracy of push detection.

FIG. 8 is a graph 800 illustrating, for several wheelchair users, a range of pose angles determined when the user is known to be pushing ("true" pushes), and a range of pose angles determined when the user is known to be not pushing ("false" pushes). For example, for a given user 801, box 802 and whiskers 803, 804 indicate a range of pose angles determined when the user was known to be pushing, whereas box 805 and whiskers 806, 807 indicate a range of pose determined when the user was known to not be pushing.

As can be seen in FIG. 8, the range of true and false push pose angles may substantially overlap for some users. When establishing a per-user pose angle threshold, it may be useful to exclude pose angles that are statistically insignificant using percentiles or another statistical technique. For example, the bottom of box 802 may correspond to the 1st percentile of true-push pose angles for user 801, and the top of box 805 may correspond to the 99th percent of false-push pose angles for user 801. As can be seen in FIG. 8, for some users, excluding true-push pose angles below the 1st percentile and excluding false-push pose angles above the 99th percentile may reduce (or even eliminate) the overlap between those ranges. Accordingly, in some embodiments, the 1st percentile of true-push pose angles determined for a wheelchair user may be used to establish the pose angle threshold for that user. For example, as indicated by line 808, a pose angle threshold of about −57 degrees may be established for user 801.

A similar technique may be used to establish a per-user energy threshold. However, whereas the 1st percentile of true-push pose angles may be used to establish a user's pose angle threshold, according to some embodiments the 99th percentile may be used to establish the user's energy threshold. In some embodiments, other percentiles may be used to establish a user's pose angle threshold and/or energy threshold.

FIG. 9 illustrates a method 900 for adaptively determining pose angle and energy thresholds for a wheelchair user, according to some embodiments of the present disclosure. Step 901 determines if a push is likely occurring based on a determined pose angle, a pose angle threshold, a calculated energy, and an energy threshold, as in method 700 of FIG. 7. The pose angle and energy thresholds used in step 901 (referred to as the "current" thresholds) may be initialized to pre-determined values and updated over time using the adaptive process described herein. In one embodiment, the current pose angle may be initialized to zero, as illustrated by line 809 in FIG. 8. In step 902, the number of push detections since a last epoch of time may be counted and used to calculate a push rate.

In step 903, a determination is made as to whether the user is actually pushing. This determination can be made using one or more criteria. In some embodiments, the user is determined to be pushing if the push rate (from step 902) is consistent over a pre-determined time interval (e.g., the last X seconds). For example, the current push rate may be compared against one or more previously calculated push rates to determine if the push rate has remained constant within some margin of error. In some embodiments, the user is determined to be pushing if the user's speed is greater than a minimum speed threshold (e.g., >0 m/s). In some embodiments, the user's speed is determined using a GPS sensor within the wearable device.

[Inventors: Are there Other Techniques You could Use to Determine if the User is Actually Pushing?]

If it is determined that the user is actually pushing (i.e., a "true" push is occurring), then, in step 904, the determined pose angle and calculated energy may be stored (e.g., within a memory of the wearable device). In some embodiments, these values may be written to a buffer. In some embodiments, the buffer may be a managed as a fixed-size, first-in first-out (FIFO) queue, wherein older values may be removed from the buffer when new values are added.

In step 905, a candidate pose angle threshold and a candidate energy threshold may be calculated based on stored pose angles and calculated energies. In some embodiments, the candidate pose angle threshold may calculated as the 1st percentile of stored pose angles, and the candidate energy threshold may be calculated as the 99th percentile of stored calculated energies. In some embodiments, the percentiles may be calculated over all values stored for the user (e.g., all values within a buffer). In other embodiments, the percentiles may be calculated over a subset of the user's stored values (e.g., the most recent N values).

In step 906, a new pose angle threshold and a new energy threshold may be calculated based on the respective candidate thresholds. The push detector 901 may update its current pose angle and energy thresholds based on these new calculated values. In some embodiments, the method 900 may be repeated periodically (e.g., about every 2.5 seconds).

In some embodiments, the new pose angle threshold ($new_{pa}$) is calculated as:

$$new_{pa} = p_{pa} \cdot candidate_{pa} + (1-p_{pa}) \cdot current_{pa} \quad (1)$$

where $current_{pa}$ is the current pose angle threshold, $candidate_{pa}$ is the candidate pose angle threshold, and $p_{pa}$ is a pre-determined constant between zero and one.

In some embodiments, the new energy threshold ($new_e$) is calculated as:

$$new_e = p_e \cdot candidate_e + (1-p_e) \cdot current_e \quad (2)$$

where $current_e$ is the current energy threshold, $candidate_e$ is the candidate energy threshold, and $p_e$ is a pre-determined constant between zero and one.

It will be appreciated that equations (1) and (2) shown above are types of low-pass filters that may be useful for preventing the pose angle and energy thresholds from changing too rapidly. The rate of change of the thresholds may be controlled by adjusting the respective filter coefficients $p_{pa}$ and $p_e$.

It is appreciated herein that a wheelchair user's pose angle and calculated energy may vary depending on their push rate. To further improve the accuracy of push detection, some embodiments of the present disclosure group historical pose angle and energy data based on the push rate at the time the data was collected or stored. In some embodiments, multiple buffers of historic data may be maintained, each buffer storing data for corresponding to a discrete range or push rates. Accordingly, in steps 905 and 906, the candidate and new threshold values may be calculated over data collected/stored when the wheelchair user was pushing at a rate similar to the current push rate (from step 902).

Figure 10:
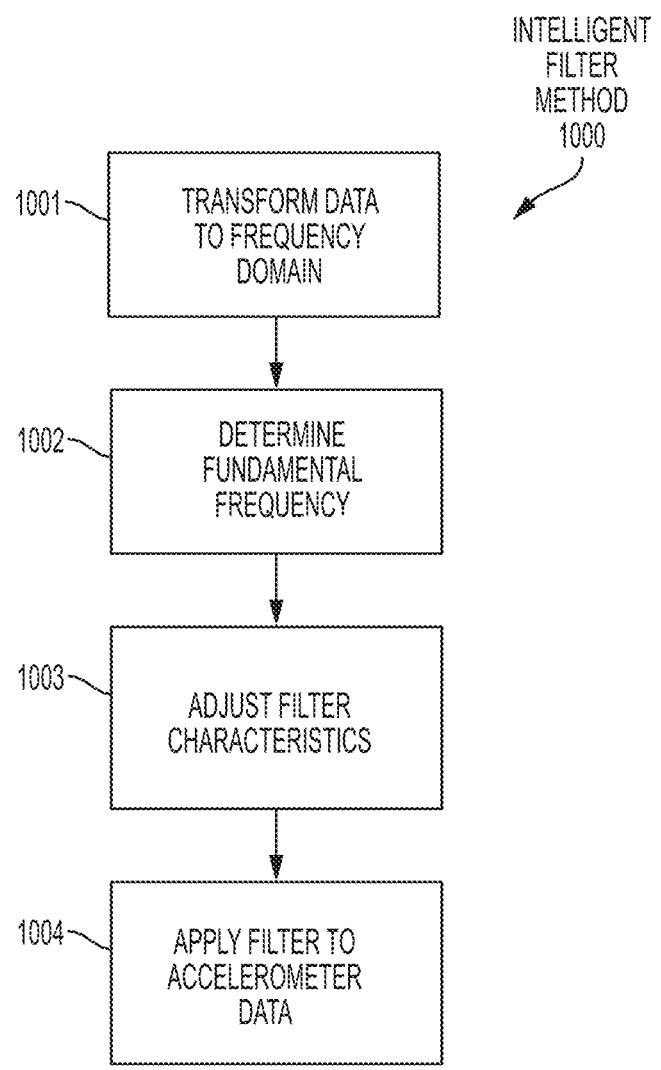
FIG. 10 illustrates a method of intelligently filtering the motion data to eliminate noise while maintaining the signal representing individual pushes, according to aspects of the present disclosure.

FIG. 10 illustrates a method 1000 of intelligently filtering the motion data to eliminate noise while maintaining the signal representing individual pushes, as in step 603 of FIG. 6. Because pushing a wheelchair is typically a rhythmic movement occurring at relatively consistent intervals, frequency domain data can be useful in detecting pushes. In one embodiment, the intelligent filter of the disclosure is a low-pass filter with adjustable passband width. In another embodiment, the intelligent filter is a bank of low-pass filters with increasing passband widths, where one of the filters in the bank of filters is selected to filter the accelerometer signal. In another embodiment, the intelligent filter is an adjustable bandpass filter with adjustable passband cutoff frequencies and width. In step 1001, the push signal is transformed to the frequency domain (e.g., by using a FFT operation). In one embodiment, the FFT includes 256 frequency bins and operates at 50 Hz. In step 1002, the fundamental frequency of pushing is determined. In one embodiment, this is done by determining the FFT peak of the lowest frequency that rises above a predetermined threshold level of energy. In step 1003, the intelligent filter passband is adjusted so as to pass the fundamental frequency determined in step 1002, but not to pass harmonics of the fundamental frequency. In step 1004, the intelligent filter filters the motion data and outputs a filtered accelerometer signal.

In some circumstances, a user's pushing may not be rhythmic. For example, a user may change their push frequency (e.g., going from 1 push every 2 seconds to 1 push every 5 seconds). In these circumstances, as the push energy is smeared across multiple frequencies, the FFT results may again not contain a strong fundamental frequency and there may be no single FFT peak that rises above the predetermined threshold level. If a different fundamental frequency detector is used, it may similarly fail to detect a fundamental frequency. In such an instance, the adjustable intelligent filter may be adjusted to a default state, or alternately a separate default filter may be used. This filter is then applied to the motion data and the method continues as described above.

Figure 11:
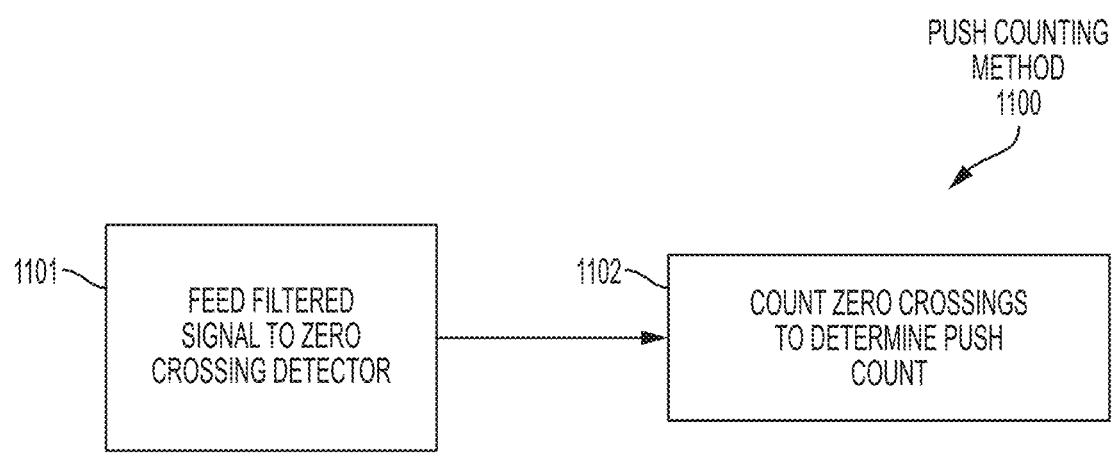
FIG. 11 illustrates a method of counting pushes using filtered motion data, according to aspects of the present disclosure.

FIG. 11 illustrates a method 1100 of counting pushes using filtered motion data as in step 604 of FIG. 6. After filtering with the intelligent filter bank of method 1000, the output signal is roughly a sine wave representing the push signal. In step 1101, the sine signal is fed to a zero crossing detector. In step 1102, the push count is incremented based on detection of zero crossings. In one embodiment, all zero crossings are detected and the push count is equal to the number of zero crossings detected by the zero crossing detector divided by two. In another embodiment, the zero crossing detector only detects crossings in one direction (e.g., from negative to positive) and the push count is equal to the number of zero crossings detected by the zero crossing detector.

Figure 12:
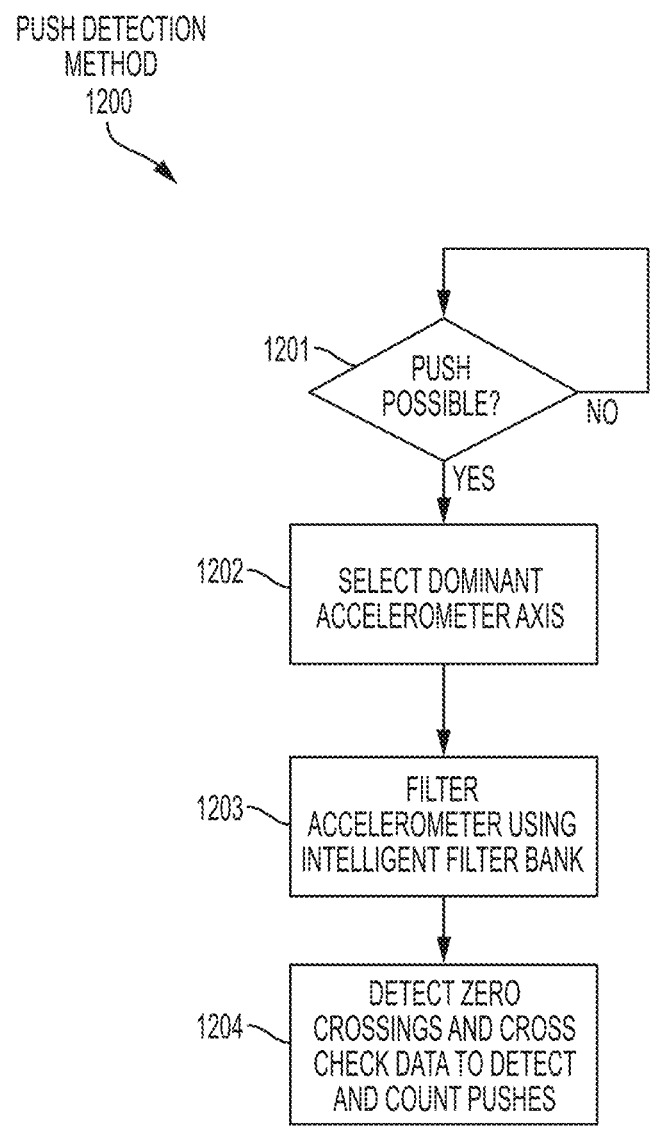
FIG. 12 illustrates a method in which an additional cross-checking step is performed, according to aspects of the present disclosure.

FIG. 12 illustrates a method 1200 in which an additional optional cross-checking step is performed. Steps 1201, 1202, and 1203 are the same as steps 601, 602, and 603. Step 1204 incorporates an additional cross-checking function, in which the detection of a zero-crossing is cross-checked using additional data. Cross-checking may be performed by, for example, applying the same algorithm or an alternative algorithm to detecting pushes on a different axis. In one embodiment, the strongest axis is used as in the embodiment of FIG. 6, but the second strongest axis is used to generate a cross-checking signal. In one embodiment, data from a companion device 300 is used to cross-check push data to ensure that the motion is derived from the wheelchair user's arms, rather than overall motion of the user. In step 1204, detections of a zero-crossing are cross-checked using the cross-checking signal to verify push detection.

Figure 13:
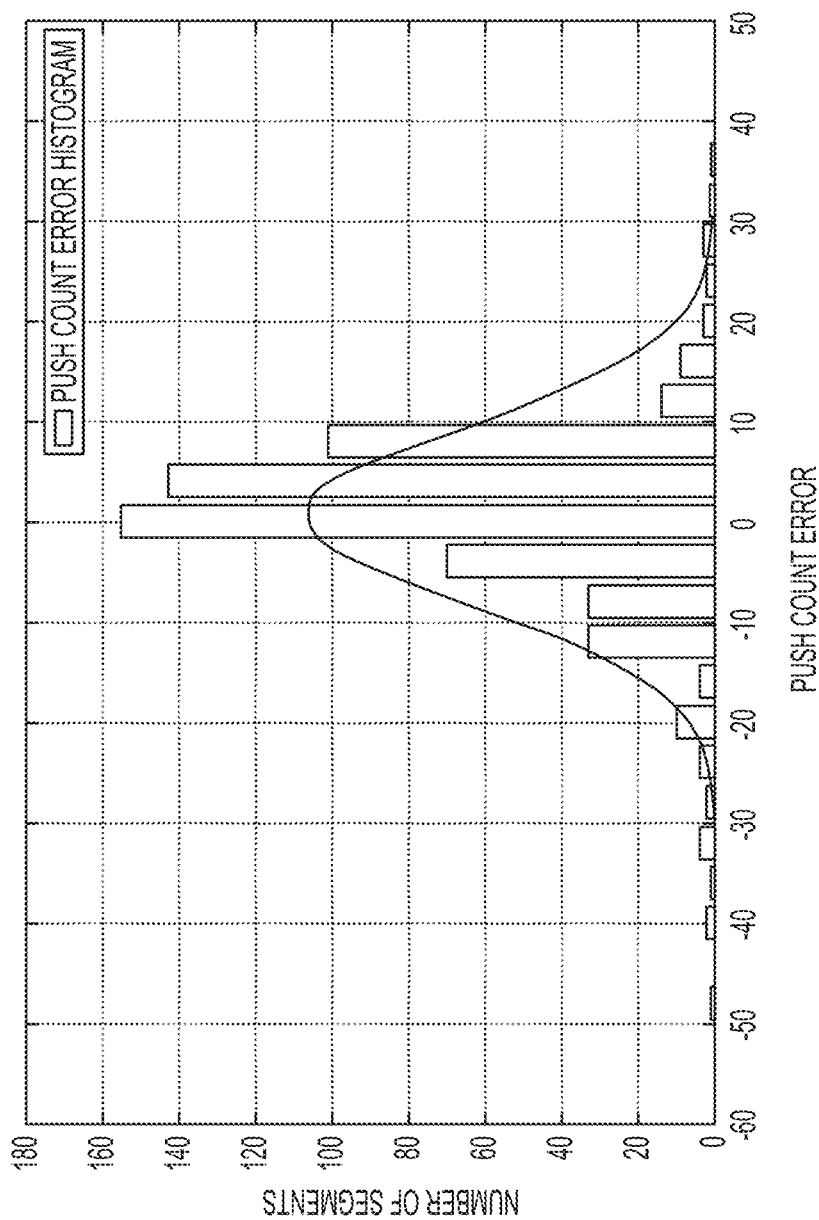
FIG. 13 illustrates performance of aspects of the present disclosure as applied to measured wheelchair user data.

FIG. 13 illustrates performance of aspects of the present disclosure as applied to measured wheelchair user data. Wheelchair users wore a wearable device for 257 workout sessions during which they repeatedly pushed the wheelchair as part of the workout, for a total of about 30 pushes per session. An embodiment of the present disclosure was applied to the data recorded during these workout sessions and used to generate a push count estimate. The estimated push count was compared to the actual push count, and the error per session was used to generate the histogram of FIG. 13. The mean push count error is 1% and the standard deviation of the push count error is 9%.

Push detection as described in the present disclosure can be utilized in numerous ways. For example, a push counter can be used to improve estimates of calories expended by the wearer of a wearable device. By estimating the calories expended in a given push, the number of pushes can be used to generate an estimate of caloric expenditure by the user. Alternately, the number of pushes in a minute can be determined, and if the number of pushes exceeds a certain threshold, the minute can be determined to be an "exercise minute" as tracked by some wearable devices. Similarly, if tracking is of rowing strokes, push-ups, or other similar repetitive arm motions, similar estimates of caloric expenditure or exercise minutes can be determined.

Referring to FIGS. 14-22, the present disclosure also describes a wearable device that may be configured to detect when a user who is pushing a wheelchair is on a ramp. Wheelchair users may navigate up and down ramps and other surfaces with gradual inclines as part of their daily routine. For example, ramps may replace stairs or other ways to gain or lose elevation. Moving up in elevation requires significant additional work to overcome the force of gravity, which is reflected by an increase in caloric expenditure. Detecting changes in elevation is needed to accurately and consistently characterize caloric expenditure over the course of a day. While a barometric sensor, as present in many smartphones, can detect gross changes in elevation, the typical changes in elevation for ramps are within the sensor error range for a barometric sensor, and measurements tend to drift over time. For example, barometric measurements change due to temperature changes or due to where the sensor is placed (e.g., in a pocket or bag).

Figure 14:
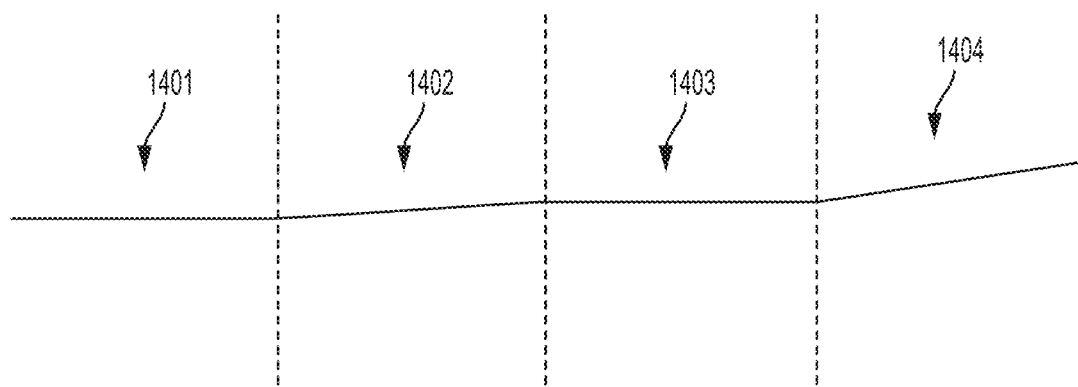
FIG. 14 illustrates a wheelchair climbing a ramp in accordance with an embodiment of the present disclosure.

FIG. 14 illustrates a ramp for use with wheelchairs as an example of various ramp grades to be detected in accordance with an embodiment of the present disclosure. The ramp starts as a zero grade flat surface 1401, becomes a low ramp of approximately two degrees angle 1402, an additional zero grade flat surface 1403, and then a high ramp of approximately 4.8 degrees angle 1404. The dashed lines mark the points at which the grade transitions. A high ramp is approximately as steep as the maximum ramp allowed in new construction by the Americans with Disabilities Act (i.e., a 1" rise for every 12" of length, yielding a 4.8 degree ramp angle or an 8.3% ramp grade.) Different ramp angles require different amounts of effort. Additionally, different ramp angles can present different challenges in detection of a ramp, as the change in elevation and resulting change in effort varies.

Figure 15:
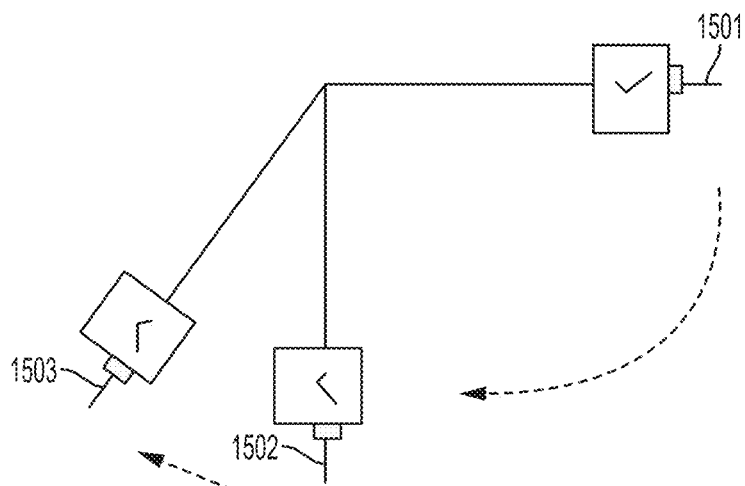
FIG. 15 illustrates an example of motion through a wheelchair push stroke, showing pose angle against the horizon.

FIG. 15 illustrates an example of motion through a wheelchair push stroke, showing pose angle against the horizon. Pose angle is defined as the angle between the wearer's arm and the horizon. Pose angle may be estimated, for example, by determining an arm angle using motion data and determining the direction of gravity using motion data, and thereby estimating the pose angle, as described in U.S. patent application Ser. No. 14/501,930, entitled "Method and System to estimate day-long calorie expenditure based on posture," which is hereby incorporated by reference in its entirety. As the accelerometer axes are based on the positioning of the wearable device, which may rotate with the user's wrist during pushing a wheelchair, they do not align perfectly to the wheelchair axes throughout the pushing motion, and pose angle may be a more relevant measure of the arm's current position. For example, if a user is sitting upright and pushes the wheels at their top portion using a short arc pattern, then the Y axis aligns primarily to the direction of forward motion, with the X axis aligned in the direction of gravity and the Z axis aligned with the axle of the wheel. In another case, if a user leans forward and pushes the wheels on the front of the wheel using a single loop pattern, then the X axis is aligned with the direction of forward motion, with the Y axis perpendicular to that direction and the Z axis aligned with the axle of the wheel.

In position 1501, the user's arm is extended straight forward from the elbow, forming a 0 degree angle with the horizon. The X axis is pointed towards the horizon, the Y axis is pointed vertically up, and the Z axis is pointed out of the page. In position 1502, the user's arm has rotated so that it is pointed straight down from the elbow, forming a negative 90 degree angle with the horizon. The X axis is now pointed vertically down, the Y axis is pointed at the horizon, and the Z axis remains pointed out of the page. In position 1503, the arm has swung even further, extending down at an angle past straight down, forming an angle greater than negative 90 degrees with the horizon. The X axis is pointed along the user's arm (i.e., at a greater than negative 90 degree angle from the horizon), the Y axis is perpendicular to that along the plane of the page (i.e., at a negative angle with the horizon but of less than 90 degrees) and the Z axis remains pointed out of the page.

In one embodiment of the disclosure, a method is presented to estimate whether a wheelchair user is on a ramp based on motion data as well as optionally based on additional data such as barometric pressure, GPS signals, heart rate, and/or other signals.

Figure 16:
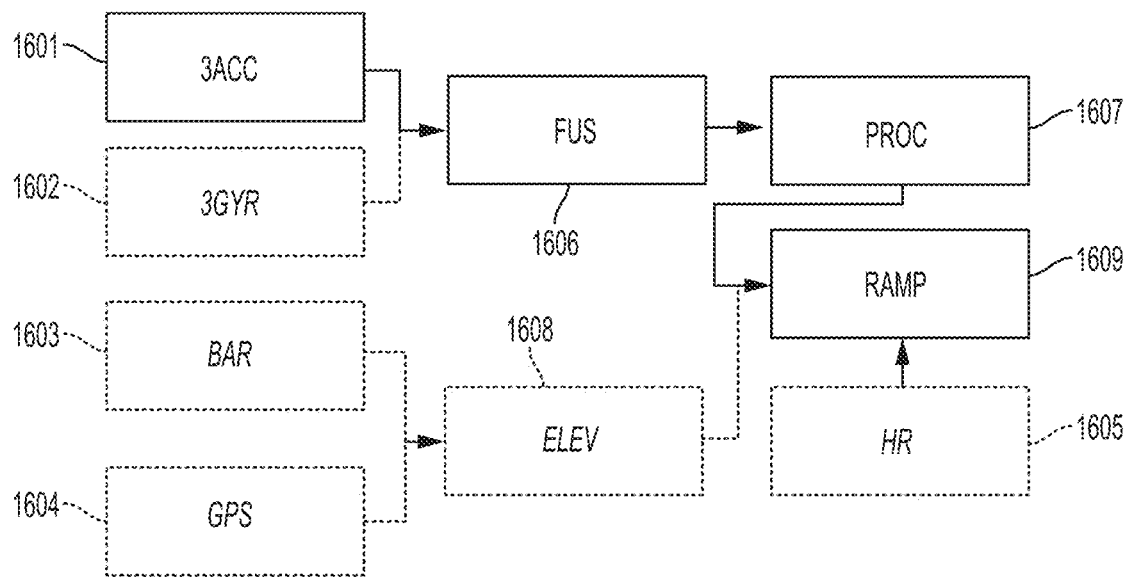
FIG. 16 illustrates sensor data sources that may be integrated to detect ramps in accordance with an embodiment of the present disclosure.

FIG. 16 illustrates a fusion of sensor data sources to detect ramps in accordance with an embodiment of the present disclosure. Sources and data streams may be optional or unreliably present, which is represented by the use of italics and dotted lines. Source 1601 produces 3-axis motion data, providing X, Y, and Z acceleration data. Source 1602 produces 3-axis gyroscope data, providing X, Y, and Z rotational information. Source 1603 measures barometric pressure. Source 1604 produces GPS data. Source 1605 measures heart rate data. Each of these sources may be determined by a sensor on a wearable device such as a watch, a sensor on a companion device such as a phone, or by sensors on both the wearable device and the companion device.

Sources 1601 and 1602, from the wearable device and/or the companion device, may be used in combination via device sensor fusion 1606 to produce a stream of sensor data. This data may be processed via a sensor processing method 1607 to provide information such as motion energy (e.g., energy in the 0.2 to 4.5 Hz band), push rate of the wheelchair user, and pose angle of the wearable device. These techniques are described herein in conjunction with FIGS. 1-13 and U.S. patent application Ser. No. 14/501,930, entitled "Method and System to estimate day-long calorie expenditure based on posture," which are hereby incorporated by reference in their entireties. Sources 1603 and 1604 may be integrated into an elevation detection method 1608 which produces elevation information.

The motion energy, push rate, and pose angle produced by sensor processing method 1607, combined with elevation information produced by elevation detection method 1608 and heart rate from a heart rate sensor 1605, may all be used in ramp detection method 1609, which results in a determination of whether the wheelchair user is on a ramp. As elevation and heart rate information may not always be available, or may be expensive in terms of power required compared to motion data, elevation and heart rate information may not be used, or may be used less frequently. The use of motion energy, push rate, and pose angle is described in more detail below. Elevation information may be used directly to detect change in elevation due to traversing a ramp, or to refine or cross-check the results of the ramp detection algorithm. Heart rate information may be used to refine or cross-check the results of the ramp detection algorithm, for example by detecting the increased heart rate due to the higher effort required to traverse a ramp. In some embodiments, the ramp detection method 1609 may also result in a determination of approximate ramp angle.

Figure 17:
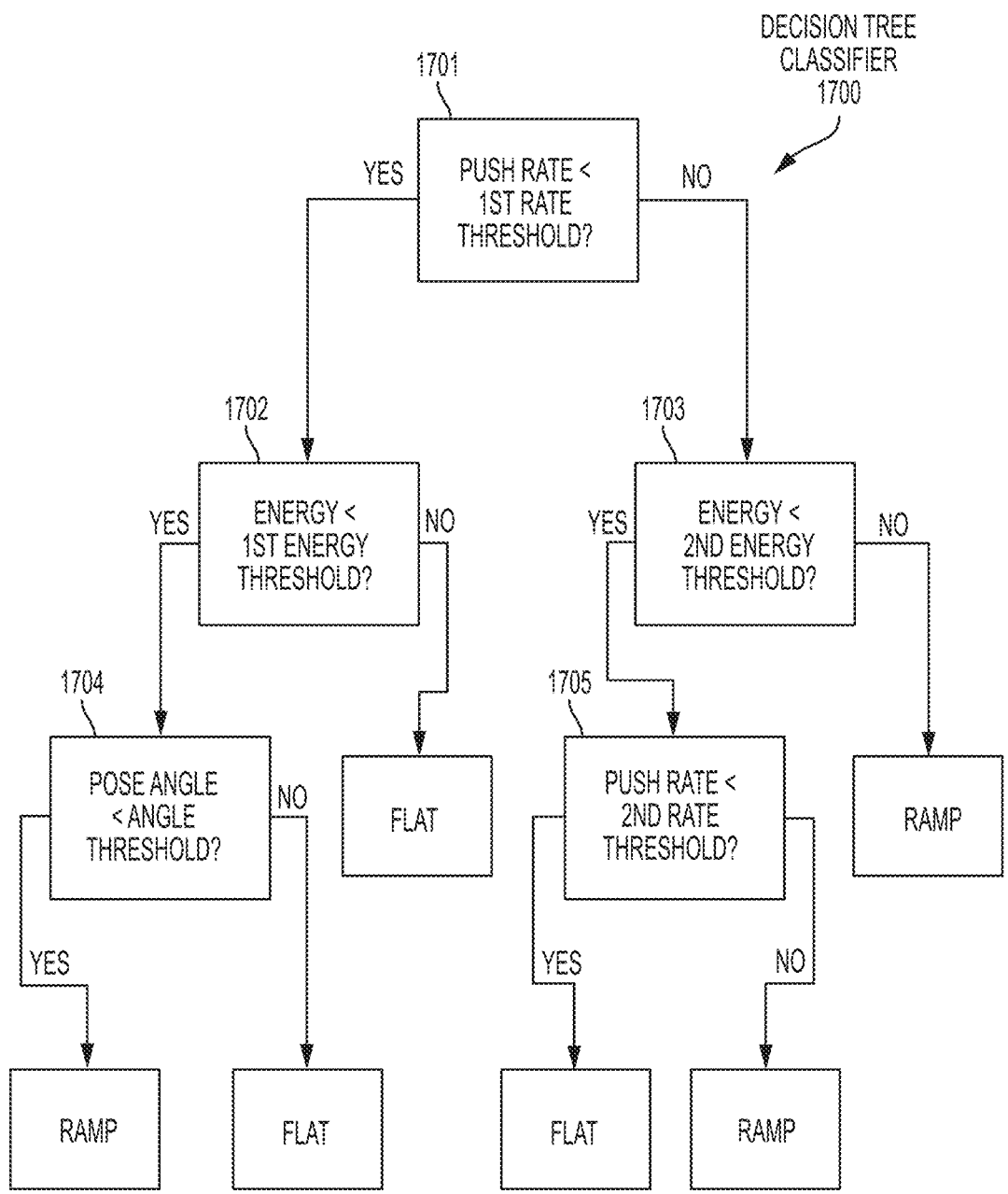
FIG. 17 illustrates a decision tree classifier that may be used to detect ramps in accordance with an embodiment of the present disclosure.

FIG. 17 illustrates a decision tree classifier 1700 that may be used to detect ramps in accordance with an embodiment of the present disclosure. In decision 1701, it is determined if a push rate (e.g., a push rate determined using techniques described herein in conjunction with FIGS. 1-13 or as determined by zero-crossing rate in the Y axis) is above or below a first push rate threshold. If it is below the threshold, decision 1702 may be selected, while if it is above or equal to the threshold, decision 1703 may be selected.

In decision 1702, it is determined if the X axis energy or a portion of the X axis energy (for example, the energy contained in the accelerometer signal in the frequency band from 0.2 to 4.5 Hz) is above or below a first energy threshold. If it is below the threshold, decision 1704 may be selected, while if it is above or equal to the threshold, the surface may be determined to be flat.

In decision 1703, it is determined if the X axis energy or a portion of the X axis energy is above or below a second energy threshold. In some embodiments of the present disclosure, the first and second energy thresholds are different from one another. If it is below the threshold, decision 1705 may be selected, while if it is above or equal to the threshold, the surface may be determined to be a ramp.

In decision 1704, it is determined if the mean pose angle on the Z axis is above or below a pose angle threshold. If it is below the threshold, the surface may be determined to be a ramp, while if it is above or equal to the threshold, the surface may be determined to be flat. In decision 1705, it is determined if a push rate is above or below a second push rate threshold. In some embodiments of the present disclosure, the first and second push rate thresholds are different from one another. If it is below the threshold, the surface may be determined to be flat, while if it is above or equal to the threshold, the surface may be determined to be a ramp.

Using this decision tree, a determination may be made as to whether the surface is flat or a ramp. In one embodiment of the present disclosure, the first push rate threshold is about 0.169922 pushes per second. In one embodiment of the present disclosure, the first energy threshold is about 11.9083 in magnitude. In one embodiment of the present disclosure, the second energy threshold is about 21.8434 in magnitude. In one embodiment of the present disclosure, the pose angle threshold is about −93.2824 degrees. In one embodiment of the present disclosure, the second push rate threshold is about 0.208984 pushes per second. While the thresholds described above may provide a reasonable approximation across many users, they may also be adjusted on a per-person basis, adaptively or using calibration data, in order to provide more accurate ramp detection, as further described below.

Figure 18:
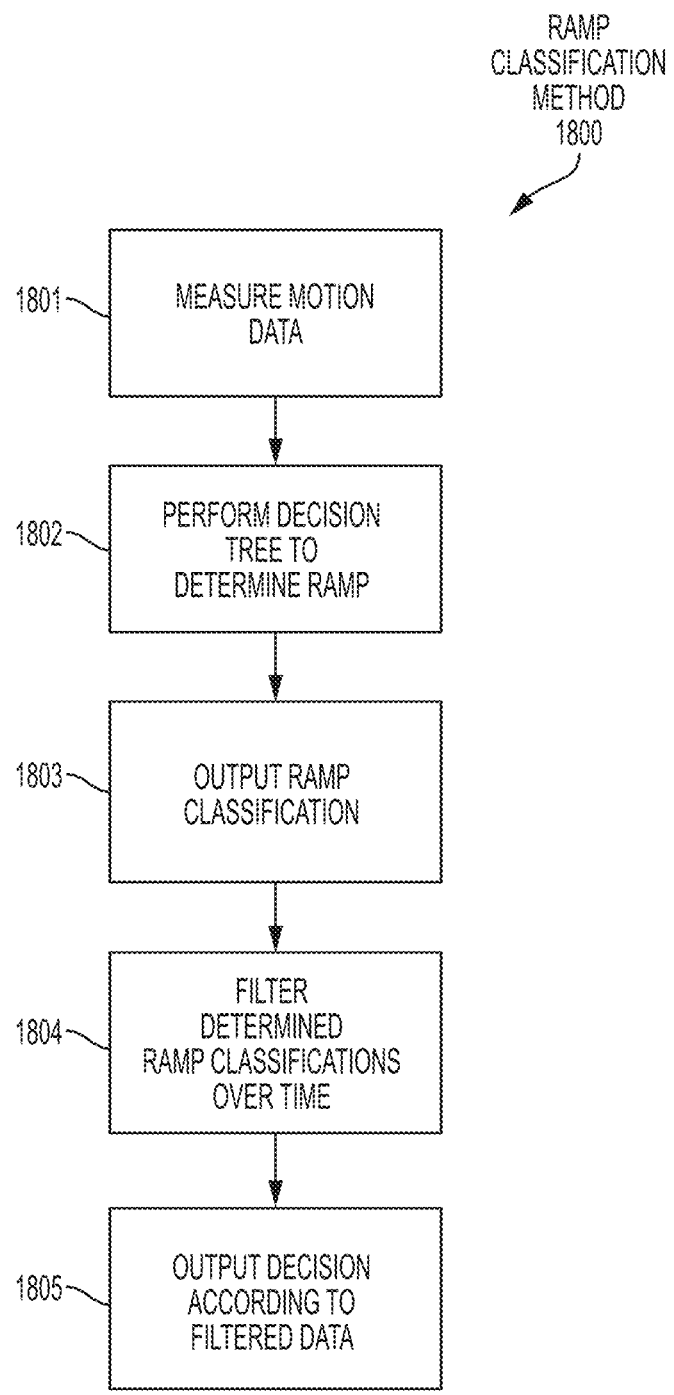
FIG. 18 illustrates a method of employing the decision tree classifier of FIG. 17 in accordance with an embodiment of the present disclosure.

FIG. 18 illustrates a method 1800 of employing the decision tree classifier of FIG. 17 in accordance with an embodiment of the present disclosure. In step 1801, motion data is measured or otherwise collected. In step 1802, the motion data is used to perform the decision tree of FIG. 17. In step 1803, ramp classification is output. In step 1804, the ramp classification is filtered over successive measurements to improve accuracy. In one embodiment, the filtering is performed using a windowing filter. In some embodiments, the windowing filter has an odd number of points in the window. In a particular embodiment, the windowing filter is a 3-point window. In a 3-point window, the ramp/flat determination in each of the three points within the window (the most recent decision, the prior decision, and the decision prior to that) are examined and the majority determination is output. In step 1805, the decision according to the output of the smoothing filter of step 1804 is output for use in a caloric expenditure estimation subsystem.

FIGS. 19A-19D illustrate the improvement in ramp detection seen using filtering or smoothing of the decision across multiple epochs of time in accordance with an embodiment of the present disclosure. FIG. 18 illustrates an embodiment in which this type of filtering is performed. In each of FIGS. 19A-19D, the real-world performance of an embodiment of the present disclosure is presented. Each bar represents the classification accuracy across for a particular individual, with a more accurate prediction being represented by a higher bar. The performance is sorted from individuals for whom the classifier performs best down to individuals for whom the classifier performs worst. A perfect classifier would produce full-height bars for all individuals.

Figure 19A:
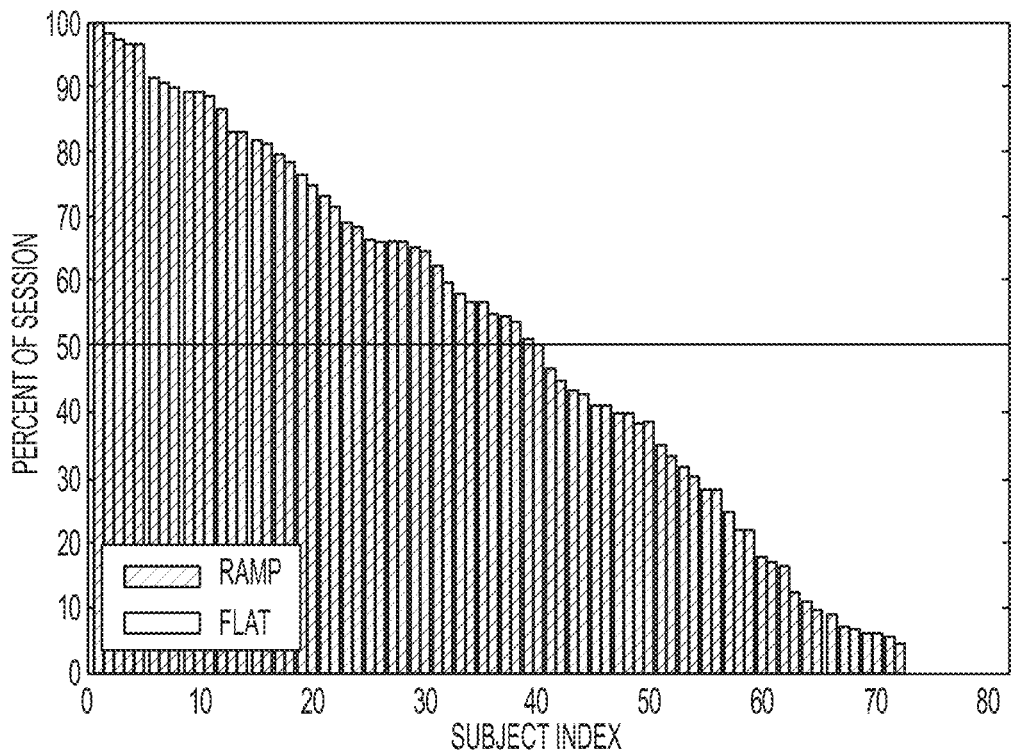
FIGS. 19A-19D illustrate the improvement in ramp detection seen using filtering or smoothing of the decision across multiple epochs of time in accordance with an embodiment of the present disclosure.
Figure 19B:
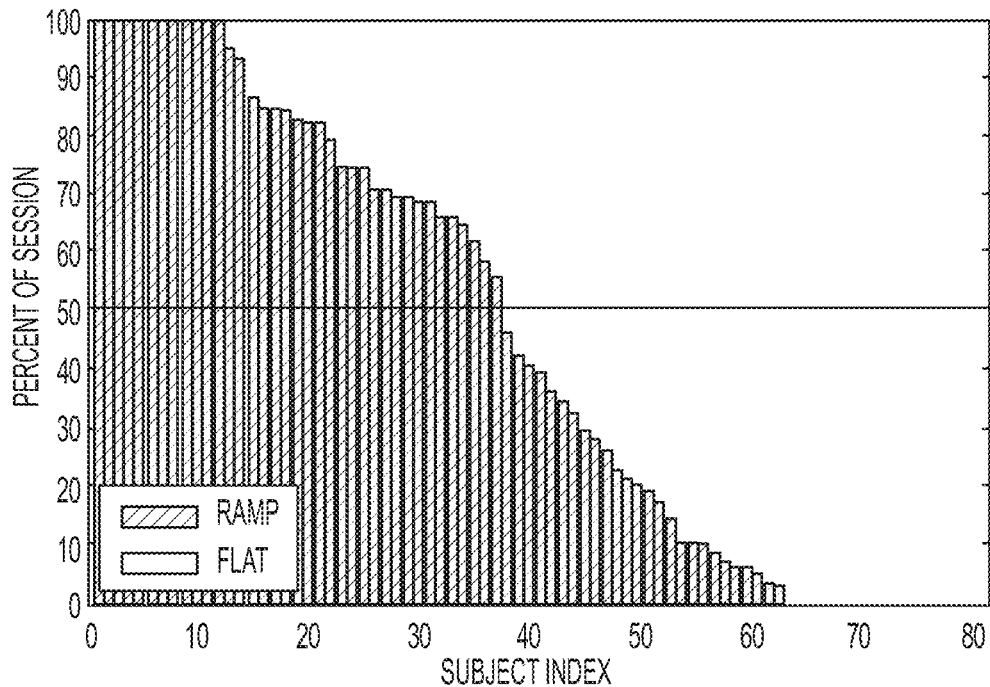

FIG. 19A illustrates the performance of the classifier when applied to users on a high ramp without any smoothing filter. FIG. 19B illustrates the performance of the classifier when applied to the same user data from users on a high ramp, but incorporating a 3-point window filter. Performance is significantly improved in FIG. 19B, with 12 users having been classified with 100% accuracy, instead of only 2 users with 100% accuracy in FIG. 19A.

Figure 19C:
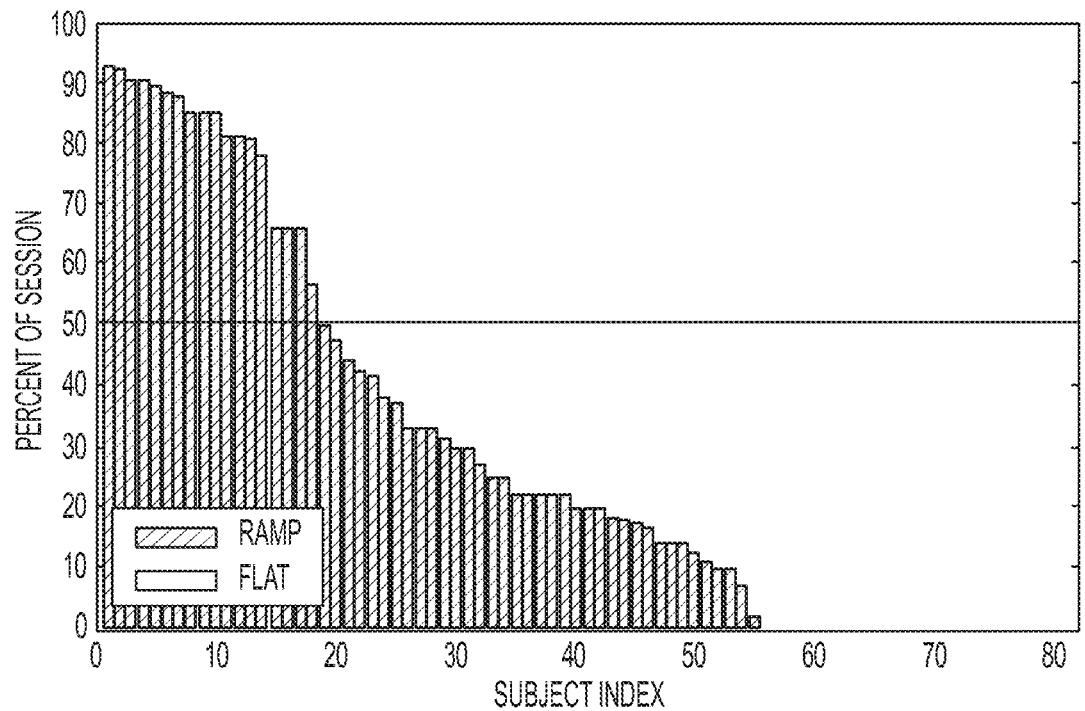
Figure 19D:
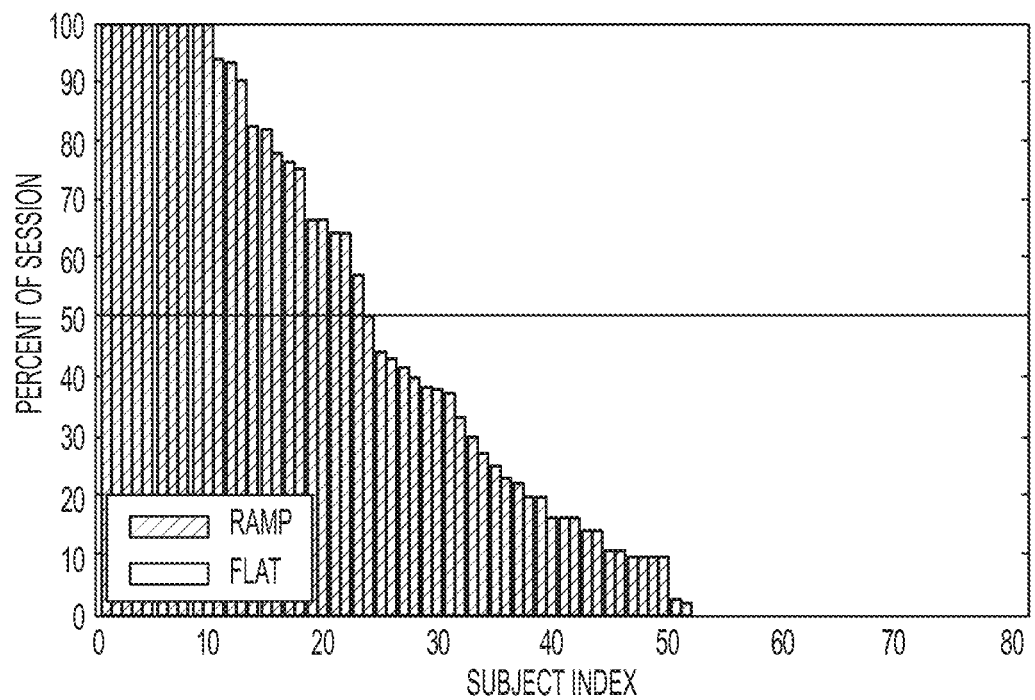

Similarly, FIGS. 19C and 19D illustrate the performance of the classifier when applied to users on a low ramp without any smoothing filter and then with a smoothing filter. Again, performance improves significantly with the application of the smoothing filter. In FIG. 19C, no users are perfectly classified. After smoothing is applied, FIG. 19D shows that 10 users are perfectly classified.

Figure 20:
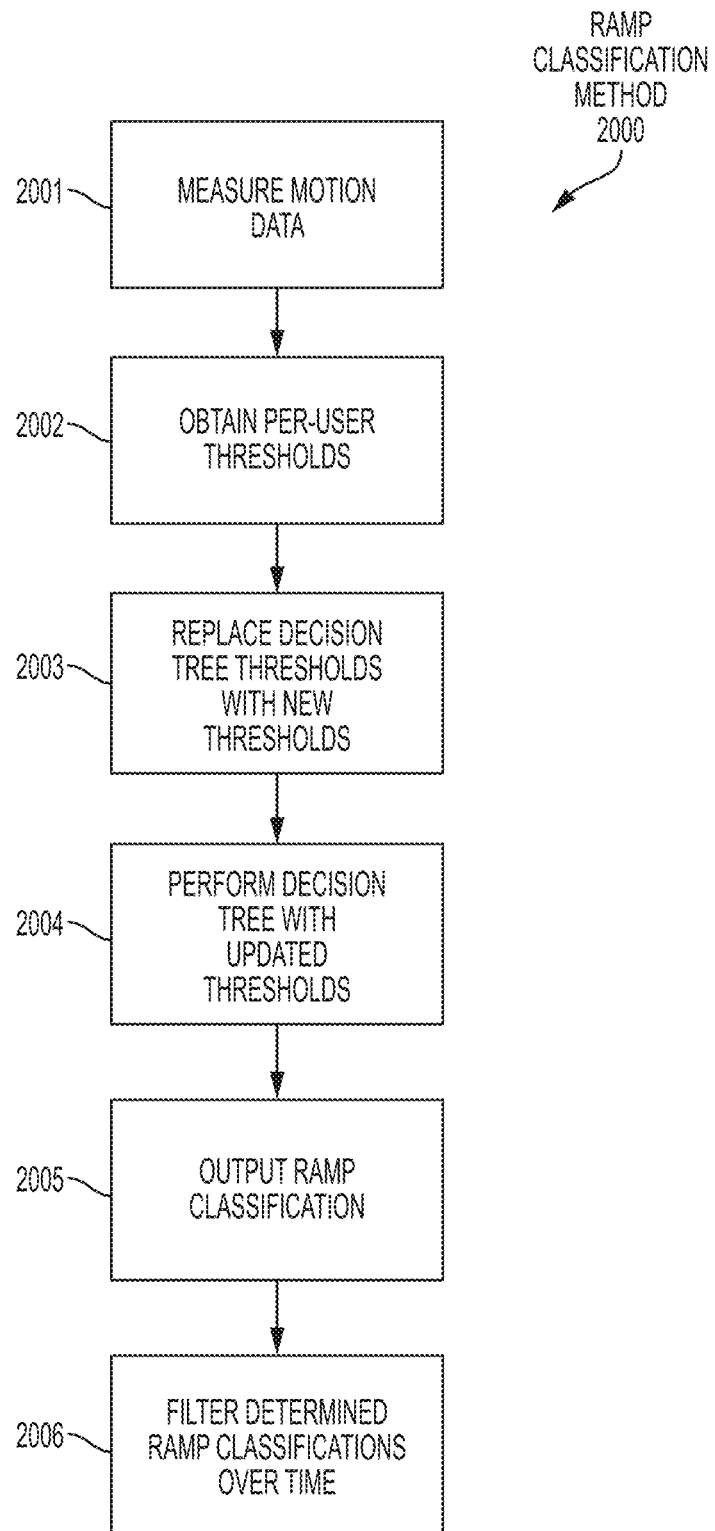
FIG. 20 illustrates a method in which thresholds are adjusted on a per-person basis to improve the accuracy of an embodiment of the present disclosure.

FIG. 20 illustrates a method 2000 in which thresholds are adjusted on a per-person basis to improve the accuracy of an embodiment of the present disclosure. In step 2001, motion data is measured or collected. In step 2002, thresholds calibrated to the user's particular characteristics are obtained. In some embodiments, the thresholds are obtained adaptively during operation. In other embodiments, the thresholds are loaded from storage where previously obtained calibrated thresholds have been stored, such as in flash memory or on a remote server. In step 2003, the calibrated thresholds replace the first and second push rate thresholds, the first and second energy thresholds, and the pose angle threshold described above with respect to FIG. 17. In step 2004, the decision tree of FIG. 17 is performed with the updated thresholds. In step 2005, the ramp classification is output, and in step 2006, the ramp classification is run through a smoothing filter to produce an improved ramp classification, as described above with respect to steps 1803 and 1804 of FIG. 18.

Figure 21A:
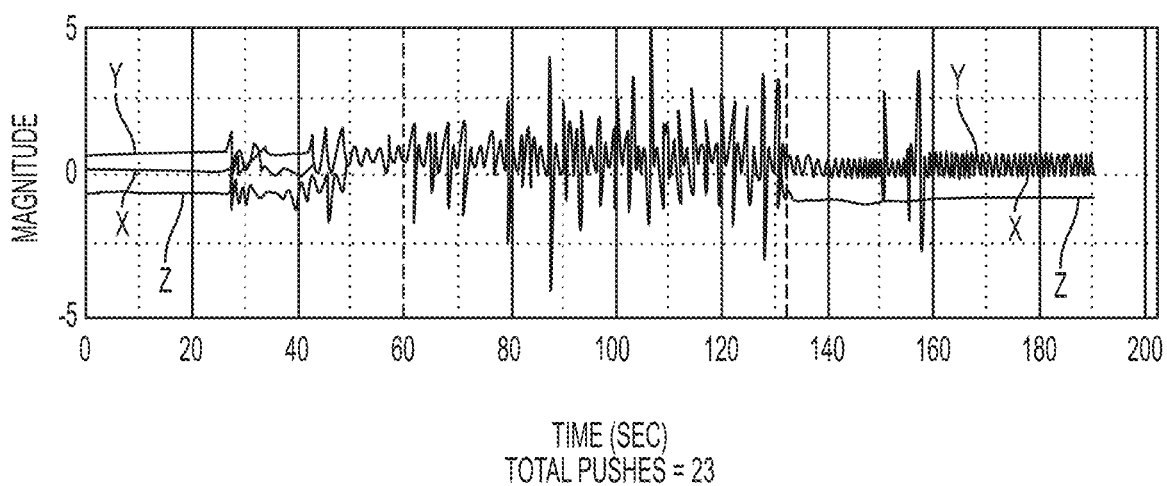
FIGS. 21A-21B illustrate performance of aspects of the present disclosure as applied to measured wheelchair user data.
Figure 21B:
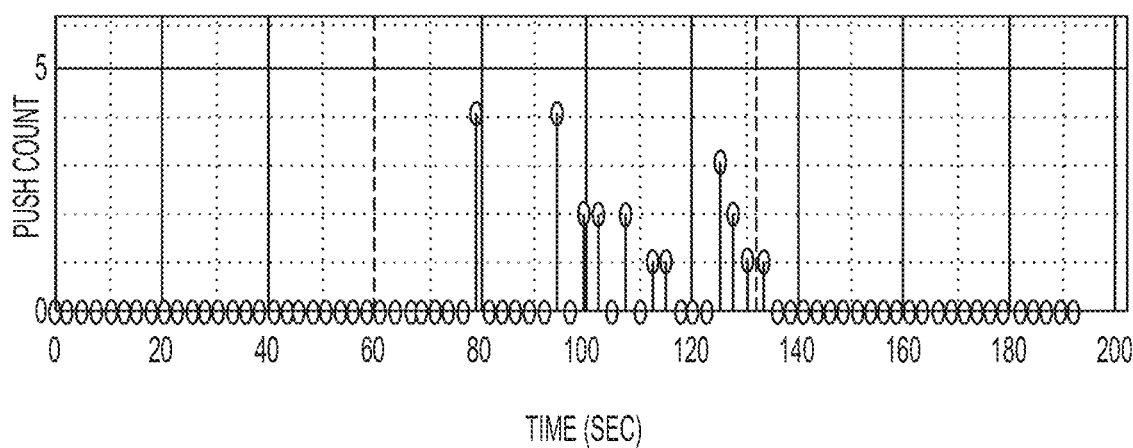
Figure 22:
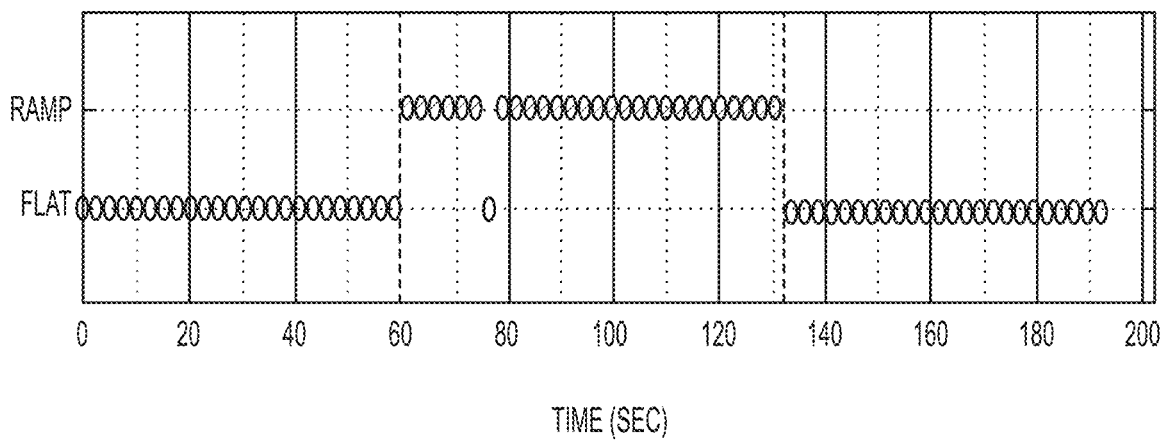
FIG. 22 illustrates an output result of the classifier in accordance with an embodiment of the present disclosure.

FIGS. 21A-22 illustrate performance of aspects of the present disclosure as applied to measured wheelchair user data over a 190 second period.

In FIG. 21A, raw motion magnitude data for a user on each of 3 axes is presented.

In FIG. 21B, the motion data is used to determine the number of pushes, as described herein in conjunction with FIGS. 1-13. The number of epochs of time per push is calculated and used as the measurement of zero crossings for the decision tree classifier.

In FIG. 22, the output of the classifier is presented. When the classifier detects a ramp, it outputs a high signal, or ramp signal. When the classifier detects a flat, it outputs a low signal, or flat signal. As shown in FIG. 22, for all but one epoch of time during the period in which the user is traveling up the ramp, the classifier outputs a ramp signal, and for all epochs of time during which the user is on a flat surface, the classifier outputs a flat signal.

Ramp detection as described in the present disclosure can be utilized in numerous ways. For example, ramp detection can be used to improve estimates of calories expended by the wearer of a wearable device. By estimating the calories expended, and adjusting the estimate based on going up or down a ramp, the estimate of caloric expenditure by the user can be improved. Alternately, if a user is pushing energetically up a ramp, the presence of the ramp can be used in determining whether to award an "exercise minute" as tracked by some wearable devices.

Other sensor signals can be used to refine the detection described above. For example, barometer or GPS elevation data can be used to double-check ramp detection by determining if the elevation data suggests a change in elevation matching the detection of a ramp. Heart rate data might be used as an additional verification by determining if user heart rate elevates to show the increased effort of traveling up a ramp. Pose angle limits compared to standard pose angle limits might be used to provide a secondary estimate of ramp angle. Each of these may be used in combination with the others, or may be omitted, according to the embodiment of the present disclosure.

Referring to FIGS. 23-27D, the present disclosure also describes a wearable device that may be configured to detect when a user is engaging in a transfer from or shift in the wheelchair. Wheelchair users may face a risk of developing pressure sores and/or other skin issues because they sit for prolonged periods of time and thus apply continual pressure to certain areas of their bodies. An incidence of a pressure sore or lesion can require a hospital stay or surgical intervention. In addition to the physical trauma of the sore, a pressure sore incident can trigger negative emotions in the wheelchair user by reminding them of having to learn how to use a wheelchair. It is typically medically recommended that a wheelchair user periodically relieve this pressure. A typical interval between pressure relief motions is 20 to 30 minutes and a typical amount of time during which the pressure should be relieved is 30 to 60 seconds. When a pressure relief motion is called for, various motions may be used, such as shifting back and forth in the chair, performing push-ups in the chair from the hand or from the elbow, or transferring out of the chair and back in. A typical wheelchair user may perform 4 to 10 transfers per day.

Existing solutions to the problem of ensuring pressure relief motions include simple timer reminders. However, while a simple timer can remind a wheelchair user that they should perform a pressure relief motion, if the user has already performed pressure relief motions they may be irritated by the unnecessary reminder. Additionally, if the user fails to properly reset the reminder, they may not receive reminders to relieve pressure, which may result in a pressure sore.

FIG. 15 illustrates a user's arm in various orientations. The X and Y axes, as measured by one or more accelerometers in the wearable device, are illustrated for each orientation. The Z-axis, as measured by one or more accelerometers in the wearable device, is pointed out of the page for all orientations shown. Motion data from a wearable device located on the user's arm may be collected periodically. In one embodiment, the motion data is collected at a 100 Hz sampling rate. The sampled motion data may be windowed into epochs using a fixed or sliding window approach. In one embodiment, a fixed window of about 2.56 seconds is used to divide the data into epochs, such that 256 samples are part of each epoch.

As described above, it is desirable to be able to detect when a user of a wearable device is performing or has completed a shift or transfer motion. Motion data can be used to derive two types of signal features of particular interest in detecting a shift or transfer. First, as described in U.S. patent application Ser. No. 14/501,930, entitled "Method and System to estimate day-long calorie expenditure based on posture" and incorporated herein by reference in its entirety, pose angles may be determined. In one embodiment, an X-pose angle and a Z-pose angle are determined. The X-pose angle is defined as the angle between the X-axis of the wearable device and the horizon, and may roughly correlate to the user's elbow angle. The Z-pose angle is defined as the angle between the Z-axis of the wearable device and the inertial Z-axis (i.e., the vertical upwards axis determined by the direction of gravity), and is roughly correlated to wrist rotation. Second, raw motion data may contain features of interest. In one embodiment, the amount of energy in the X-axis is a feature. In some embodiments, the energy is only measured within a certain frequency band of the X-axis motion data. In one embodiment, the frequency band of interest is from 0.2 to 4.5 Hz. In one embodiment, relative motion between the X, Y, and Z axes is a feature (i.e., the difference in motions between the axes is detected). In other embodiments, preparatory actions or the actual transfer may trigger features in raw motion data, such as high-frequency motions that correlate with clasping the chair tightly to prepare to lift, or tremor in the hand and wrist while supporting the wearer's weight during a shift or transfer.

Figure 23:
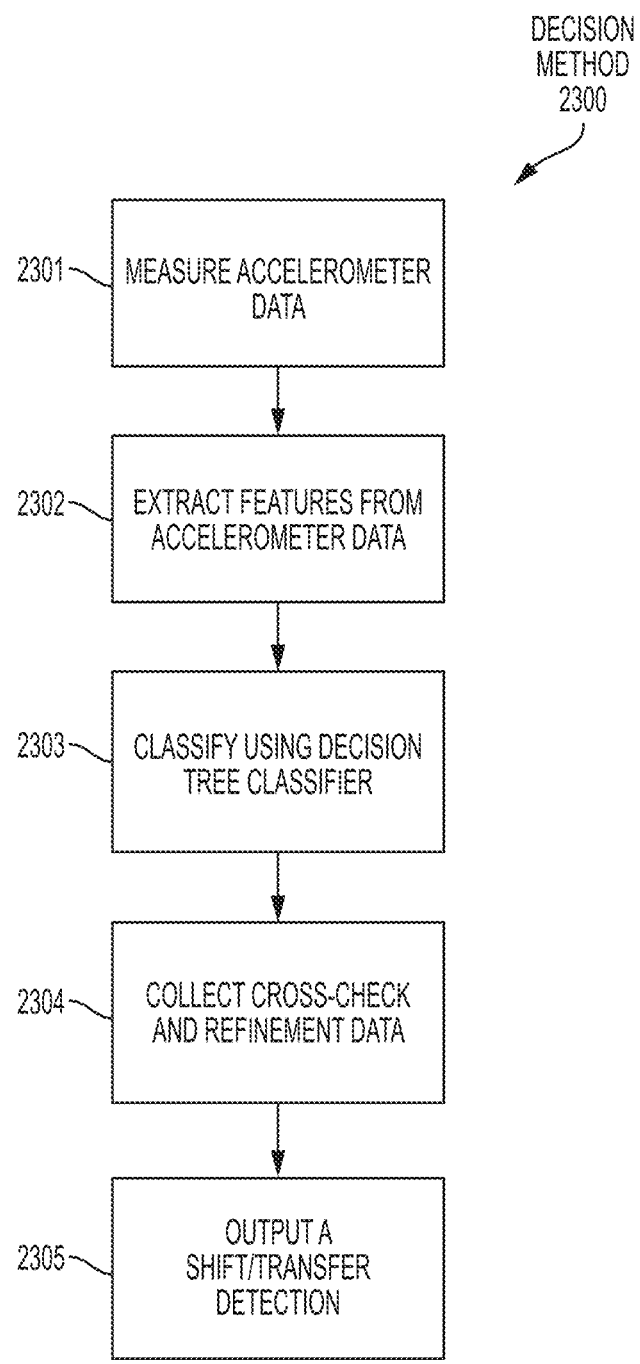
FIG. 23 illustrates a method for detecting shifts or transfers in accordance with an embodiment of the present disclosure.
Figure 25:
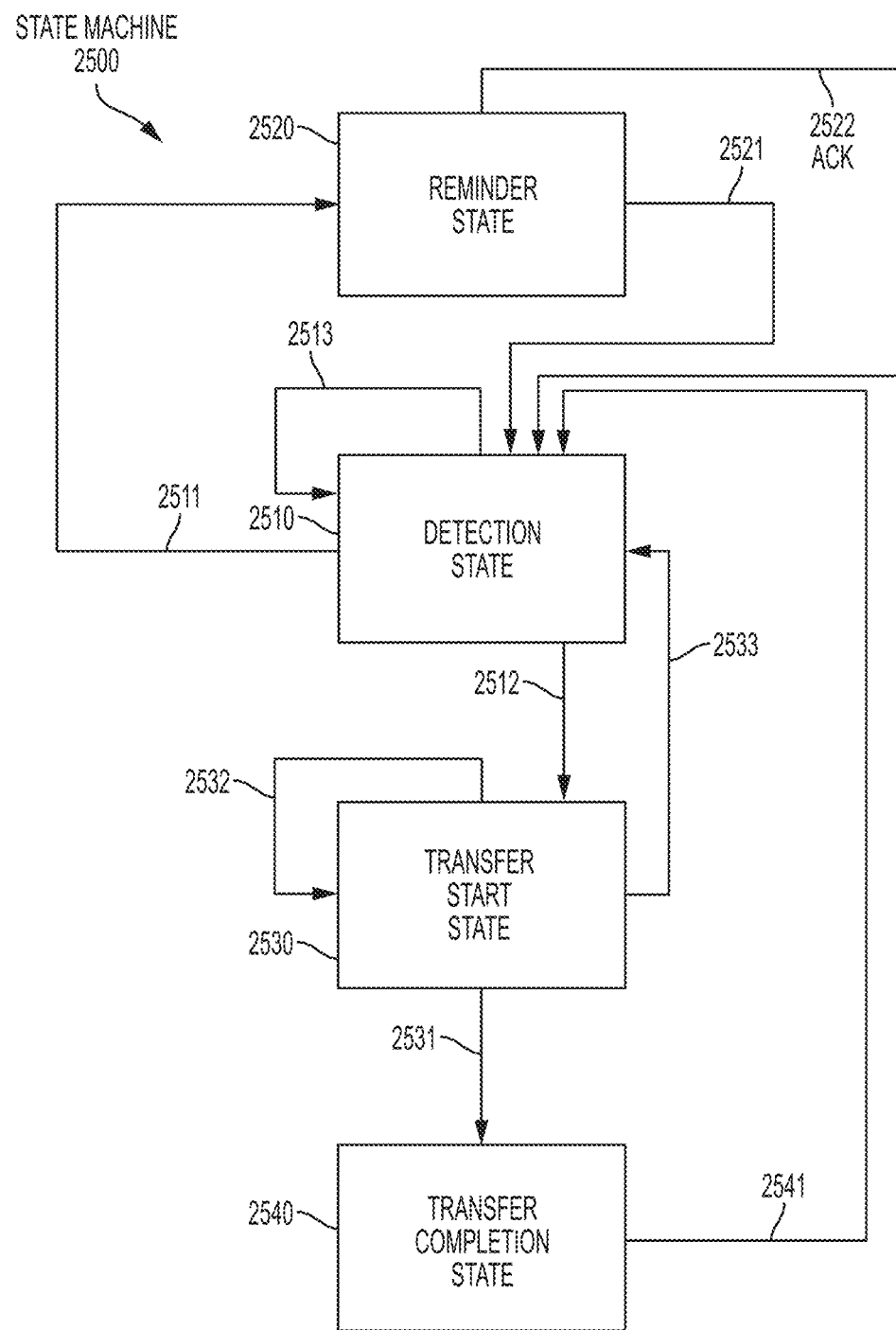
FIG. 25 illustrates a state machine used in one embodiment of the present disclosure for detection of shifts and transfers, as well as for reminding a user to engage in such motions.

FIG. 23 illustrates a method 2300 for detecting shifts or transfers. In step 2301, motion data is collected. In step 2302, the motion data is processed to extract signal features of interest. In step 2303, the features are used to classify the current state using a decision tree classifier. In such a decision tree classifier, one or more of the features may be used with one or more corresponding thresholds to produce a classification of current state. In step 2304, additional data is collected, which may be used to provide additional information regarding shifts and transfers or to cross-check the data derived from motion data. In step 2305, the detection method outputs a detection decision to a state machine, as shown in FIG. 25.

Figure 24:
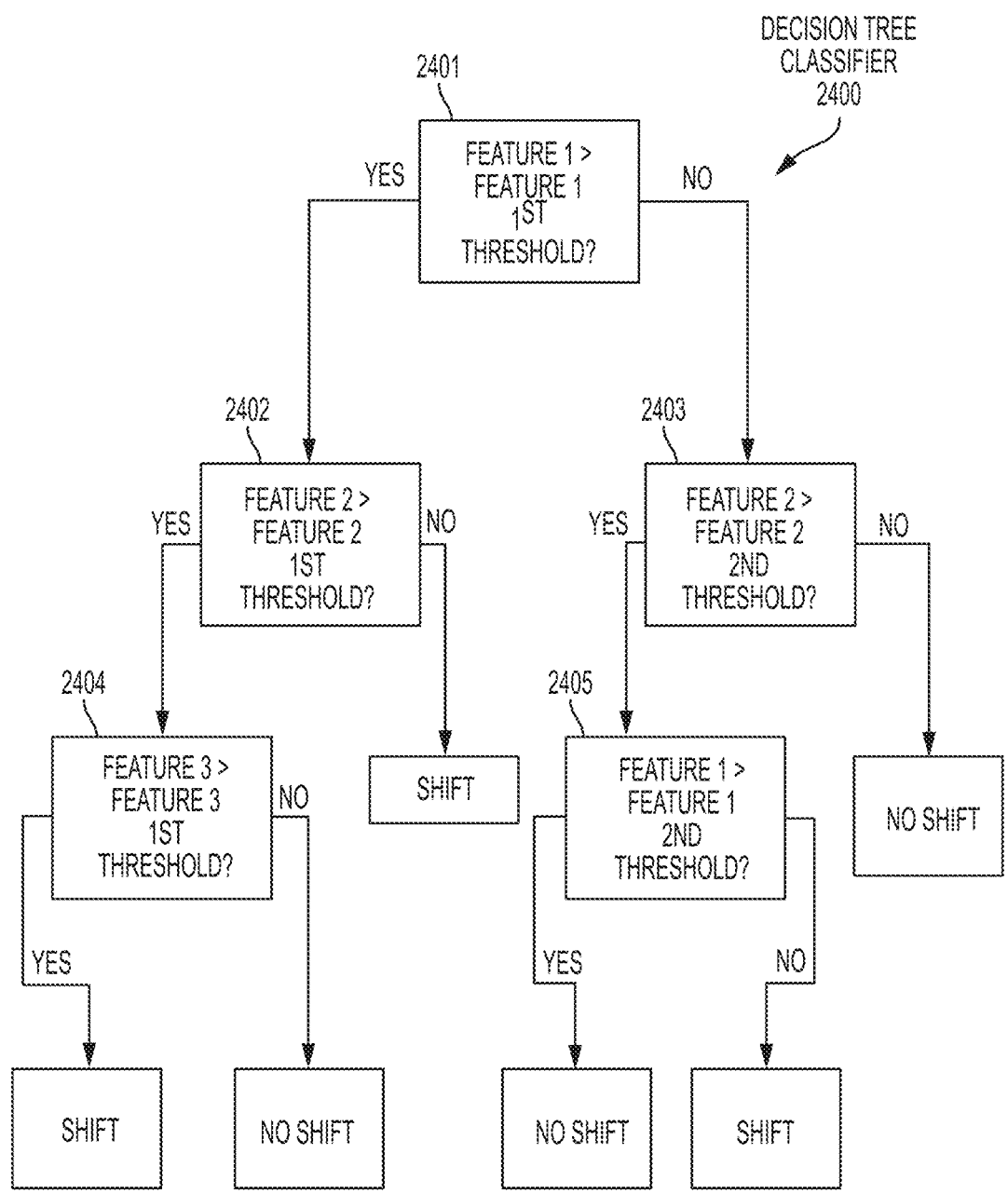
FIG. 24 illustrates a decision tree, which may be used to perform a step of the embodiment of the present disclosure described in FIG. 23.

FIG. 24 illustrates a decision tree 2400, which may be used to perform step 2303 of the embodiment of the present disclosure described in FIG. 23. In step 2401, a first feature is compared to a first threshold for a first feature and, based on the comparison, either step 2402 or step 2403 may be selected to be performed. In step 2402, a second feature is compared to a first threshold for a second feature, and based on the comparison either it may be detected that a shift or transfer has occurred, or else a step 2404 may be selected for performance. Similarly, in step 2403, a second feature is compared to a second threshold for a second feature, and based on the comparison either it may be determined that a shift or transfer has occurred, or else a step 2405 may be selected for performance. In step 2404, a third feature is compared to a first threshold for a third feature, and based on the comparison either it may be detected that a shift or transfer has occurred or not occurred, while in step 2405 a first feature is compared to a second threshold for the first feature and, based on the comparison, either it may be detected that a shift or transfer has occurred or not occurred.

While described in the context of a three-level tree, a person of ordinary skill in the art would understand that a tree of fewer or more levels may be used for detection, from as few as two levels to as many levels as are desirable for accuracy of classification and sufficient performance. In one embodiment of the present disclosure, a first feature is the X-pose angle per epoch, and a second feature is the change in Z-pose angle per epoch. A first threshold for a first feature of this embodiment is an angle of −40 degrees. A first threshold for a second feature of this embodiment is 20 degrees. In this embodiment, a two-level decision tree is used, first examining X-pose angle, then either determining non-shift or examining Z-pose angle to determine shift or non-shift.

Further, while the above-described embodiment detects when a shift has occurred and outputs a determination of either no shift or shift, in another embodiment, multiple decision trees may be utilized, with the specific decision tree being used changing depending on the current state. A first tree, used from an idle state, may output either that it has detected that a shift or transfer may be beginning, or that there has been no detection of the start of a shift or transfer. A second tree, used from a state where a start of transfer has been detected, may output either that a shift or transfer has completed, that a shift or transfer has not yet completed, and (optionally) that the start of shift/transfer previously detected was a false positive.

FIG. 25 illustrates a state machine 2500 used in one embodiment of the present invention for detection of shifts and transfers, as well as for reminding a user to engage in such motions. In state 2510, the user has performed a shift or transfer in the past and the reminder timer until the next shift or transfer is counting. A first decision tree, used to detect the start of a shift or transfer, is periodically used. In an embodiment of the present disclosure, the decision tree is used once per epoch. In an embodiment, each epoch lasts about 2.56 seconds. State transition 2511 is triggered when the reminder timer expires and the system transitions to the reminder state 2520. State transition 2512 is triggered when a first decision tree detects a start of shift or transfer, and the system transitions to state 2530. State transition 2513 occurs when a first decision tree does not detect a start of shift or transfer, and the system remains in state 2510.

In some embodiments, secondary data sources may also trigger a state transition (not shown) to state 2530. For example, information that correlates to an imminent shift or transfer, such as the connection or disconnection of a user's device from a Bluetooth receiver associated with shifts (e.g., a Bluetooth receiver in a vehicle), the user arriving at a geographic location where transfers typically occur such as an office, gym, or bathroom, or the detection of a user stopping driving may be used in detecting the start of shift state. Additionally, information such as sudden pressure changes in a companion device's barometric sensor may also be used to inform start of transfer, as a companion device is frequently placed in a rear pants pocket or under a user's leg, such that lifting the legs of the user changes the barometric pressure detected by the device.

In state 2520, a shift or transition reminder state is occurring. A reminder to the user is triggered. The reminder may be audible, visual, haptic, an electronic message, and/or any other reminder that the user may perceive. In one embodiment, the system transitions back to state 2510 via state transition 2521 after the reminder is triggered. In another embodiment, the system transitions back to state 2510 via state transition 2522 only after the user acknowledges the reminder.

In state 2530, a shift or transfer start state has been detected. When arriving in this state, a time-out timer may be initialized to prevent failures in which the device becomes stuck in state 2530. A second decision tree, used to detect the completion of a shift or transfer, is periodically used. In an embodiment of the present disclosure, the decision tree is used once per epoch. In an embodiment, each epoch lasts about 2.56 seconds. State transition 2531 is triggered when the second decision tree detects a completion of shift or transfer, and the device transitions to completion state 2540. State transition 2532 is triggered when the second decision tree detects the transfer or shift has not yet completed, and the device remains in state 2530. State transition 2533 is triggered if the time-out timer expires without detection of completion. The device transitions back to state 2510. In another embodiment, the second decision tree may also detect that a false positive detection occurred, in which case the device will also transition back to state 2510.

In state 2540, a shift or transfer completion has been detected. The reminder timer is reset automatically to the recommended time between transfers, such as a 20 minute timer, and the device transitions back to state 2510 via state transition 2541.

In a further embodiment, an additional preparing to shift state is used between the idle state 2510 and the start state 2530. In this state, information indicating a shift may be about to begin (e.g., features of interest as described above, motion data such as high frequency tremor from clasping the chair arms, state information such as Bluetooth connection or disconnection from a car, and geolocation information) is used to trigger a transition from idle state to a preparatory state. Once in the preparatory state, the first decision tree is used to generate a transition to the start state 2530.

It should be appreciated that the techniques described above allow can be used to provide "smart reminders" to a wheelchair user that properly reminds the user when the user has not performed a pressure relieving motion, but do not repeatedly remind the user when the user has already performed a pressure relief motion within the appropriate window of time.

Figure 26A:
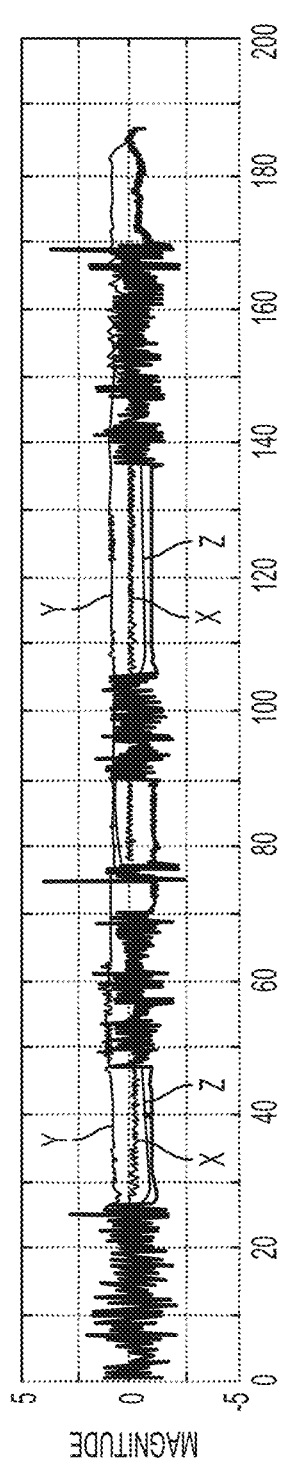
FIGS. 26A-26D illustrate data collected and processed in accordance with an embodiment of the present disclosure.
Figure 26B:
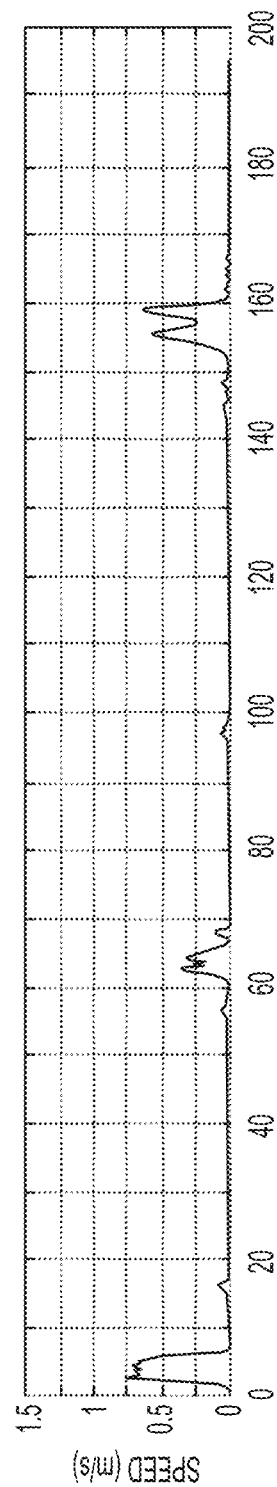
Figure 26C:
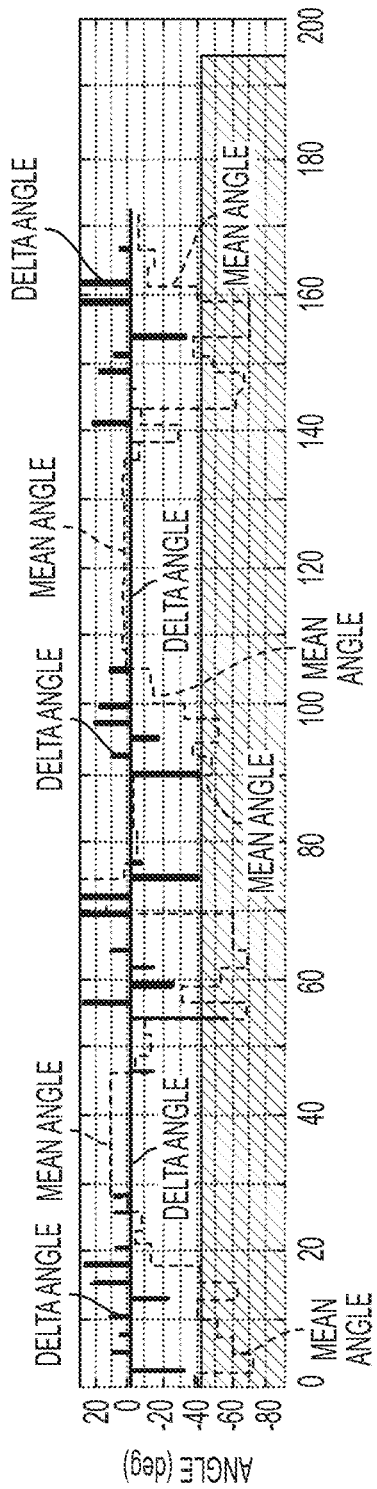
Figure 26D:
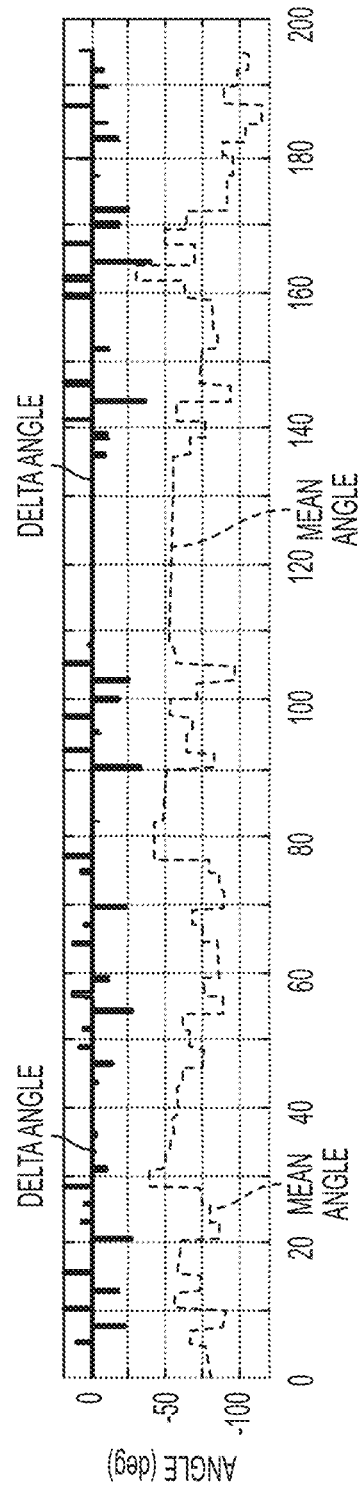

FIGS. 26A-26D illustrate data collected and processed in accordance with an embodiment of the present disclosure. FIG. 26A illustrates X, Y, and Z motion data collected from a user's wrist. FIG. 26B illustrates wheelchair wheel speed. This data is presented only for informational purposes, and is not generally collected in embodiments of the present disclosure, although it may be collected and used as a secondary data source if available (e.g., if a wheel speed sensor is present on the wheelchair). FIG. 26C illustrates the mean X-pose angle for a given epoch. The shaded area in FIG. 26C represents the typical angles associated with transfers. FIG. 26D illustrates the mean Z-pose angle for a given epoch. During the time shown in FIGS. 26A-26D, four transfers were performed—two from a chair to a bed, and two from the bed back to the chair.

Figure 27A:
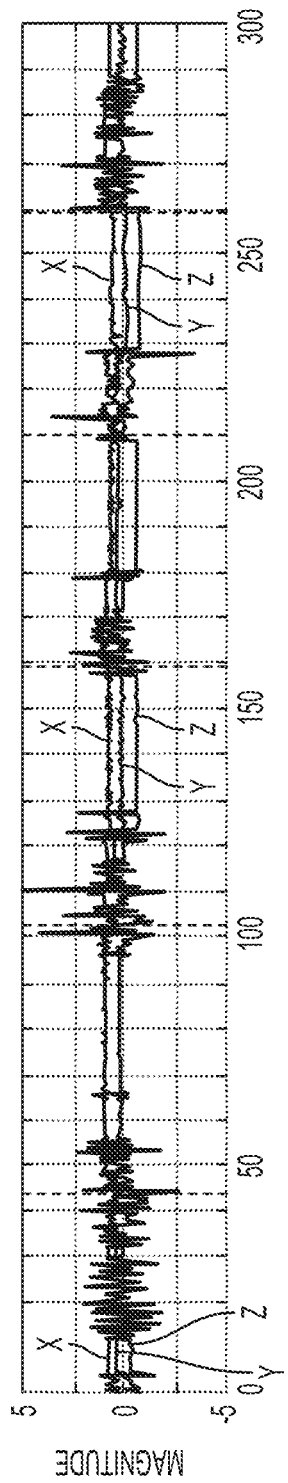
FIGS. 27A-27D similarly illustrate data collected and processed in accordance with an embodiment of the present disclosure.
Figure 27B:
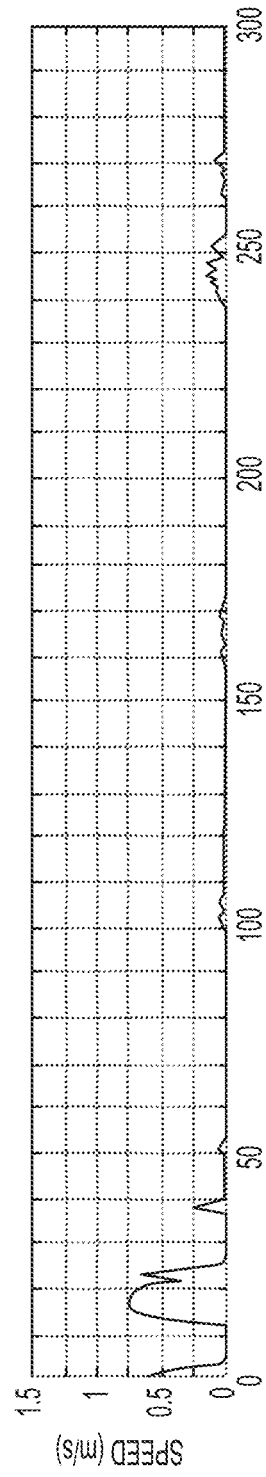
Figure 27C:
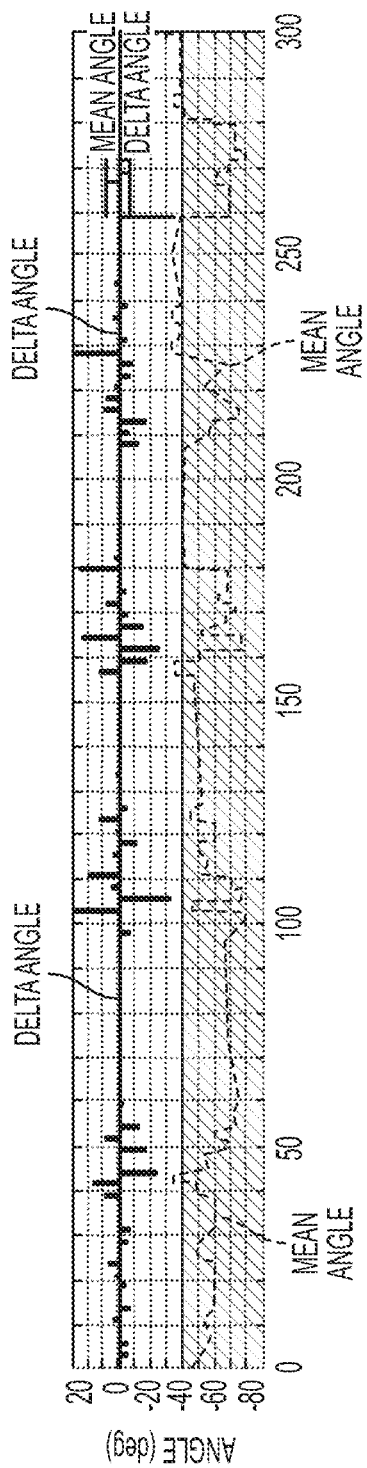
Figure 27D:
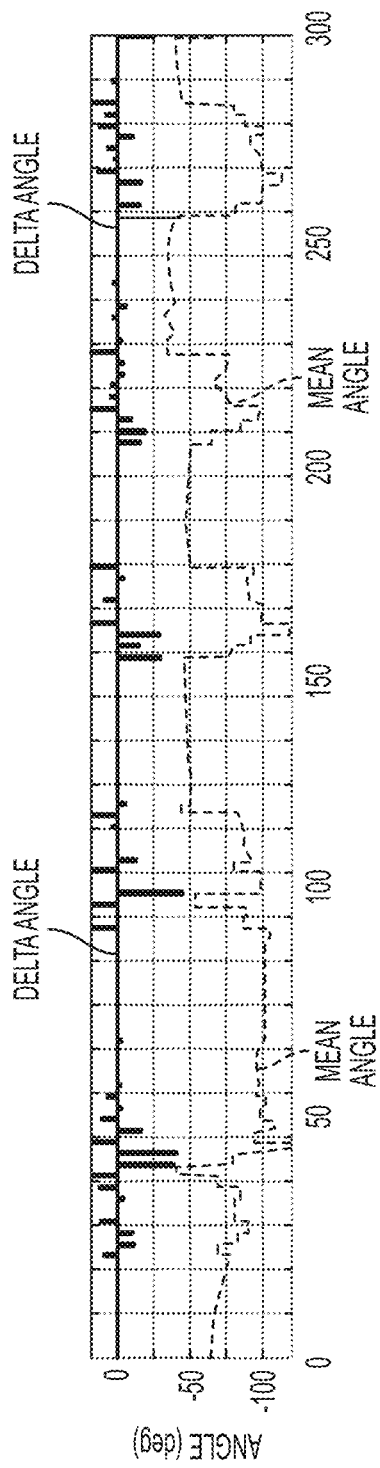

FIGS. 27A-27D similarly illustrate data collected and processed in accordance with an embodiment of the present disclosure. The data in FIGS. 27A-27D represent data from a different user than that displayed in FIGS. 26A-26D. FIG. 27A illustrates X, Y, and Z motion data collected from a user's wrist. FIG. 27B illustrates wheelchair wheel speed. This data is presented only for informational purposes, and is not generally collected in embodiments of the present disclosure, although it may be collected and used as a secondary data source if available (e.g., if a wheel speed sensor is present on the wheelchair.) FIG. 27C illustrates the mean X-pose angle for a given epoch. The shaded area in FIG. 27C represents the typical angles associated with transfers. FIG. 27D illustrates the mean Z-pose angle for a given epoch. During the time shown in FIGS. 27A-27D, four transfers were performed—two from a chair to a bed, and two from the bed back to the chair.

Transfer and shift detection as described in the present disclosure can be utilized in numerous ways, in addition to the improved reminder system described above. For example, transfer and shift detection can be used to improve estimates of calories expended by the wearer of a wearable device. A transfer or shift typically burns a significant amount of calories compared to remaining seated in the chair. As a result, by estimating the amount of calories expended during a transfer or shift and allocating a caloric expenditure of that magnitude each time the user performs a transfer or shift, the estimate of calories expended by the user can be improved. Alternately, if a user performs an extended transfer or shift of sufficient duration, the user may be awarded an "exercise minute" as tracked by some wearable devices.

Other sensor signals can be used to refine the detection described above. Heart rate data might be used as an additional verification by determining if user heart rate elevates to show the increased effort of performing a transfer or shift. Heart rate may be used in combination with the other features of interest, or may be omitted, according to the embodiment of the present disclosure.

Referring to FIGS. 28A-38, manual wheelchair users propel their wheelchairs using a variety of different arm movements. These movements can typically be classified into four overall patterns—the arc, semi-circular, single loop, and double loop patterns. Each pattern consists of a "push" phase, during which the user is expending significant energy to move the chair, and a "return" phase, in which the arm is reset so that another push phase can begin. These patterns, in turn, correlate to various aspects of wheelchair user fitness such as energy expenditure, fitness level, mobility, stroke technique (which may then correlate to rehabilitation level), and other fitness metrics. For example, the single loop pattern is typically associated with more athletic wheelchair users. The "push" phase correlates to overall energy expenditure, since most energy is expended in this phase, and the relative time spent in push versus return phases correlates to terrain features such as ramp slope. Thus, the stroke pattern and stroke phase may be used to aid in caloric expenditure estimation, and may also be used to help detect when a wheelchair push occurs to improve wheelchair stroke detection such as that described herein in conjunction with FIGS. 1-13 or ramp detection such as that described herein in conjunction with FIGS. 14-21. For example, shorter arc pattern strokes are characteristic of traveling up a ramp.

Figure 28A:
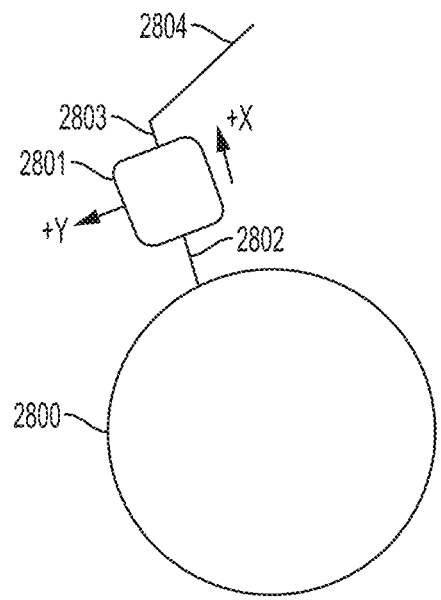
FIG. 28A illustrates the directions of accelerometer forces for a wrist-worn device on the right wrist.
Figure 28B:
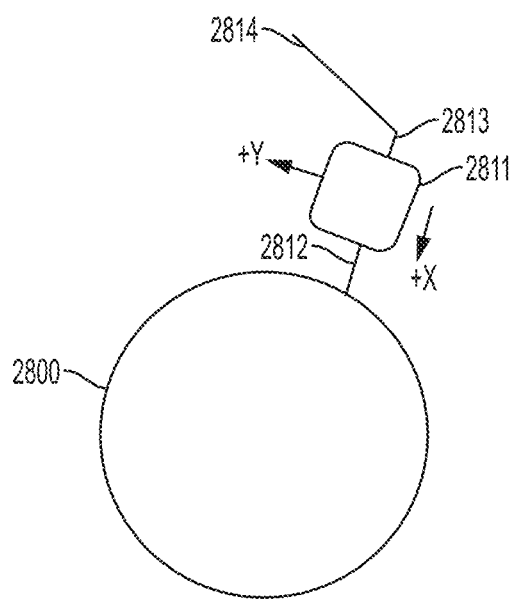
FIG. 28B illustrates the directions of accelerometer forces for a wrist-worn device on the left wrist.

FIG. 28A illustrates the directions of accelerometer forces for a wrist-worn device 2801 on the right wrist 2802 for user of wheelchair 2800. The X axis, as illustrated, is then the axis running horizontally across the display and roughly aligned with the direction of the forearm, with the positive X axis being towards the right elbow 2803 and right shoulder 2804. The Y axis, as illustrated, is the axis running vertically across the display, with the positive Y axis being generally away from the center of the body. FIG. 28B illustrates the directions of accelerometer forces for a wrist-worn device 2811 on the left wrist 2812. The X and Y axis are similarly oriented with respect to the device itself; however, because the device 2811 is located on the left wrist 2812 rather than the right wrist 2802, the sign of the X axis is inverted with respect to the body—the positive X axis is now oriented towards the left wrist 2812, rather than the left elbow 2813 and left shoulder 2814.

Figure 29A:
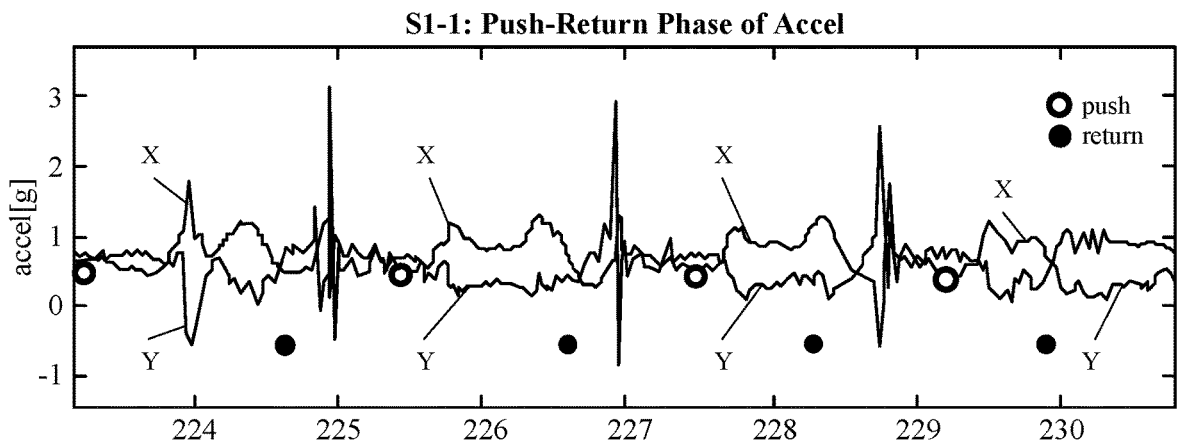
FIGS. 29A-29C illustrate X and Y accelerometer data taken during a sequence of pushes using the semicircular, arc, and single loop patterns illustrated in FIGS. 4A-4C, according to aspects of the present disclosure.
Figure 29B:
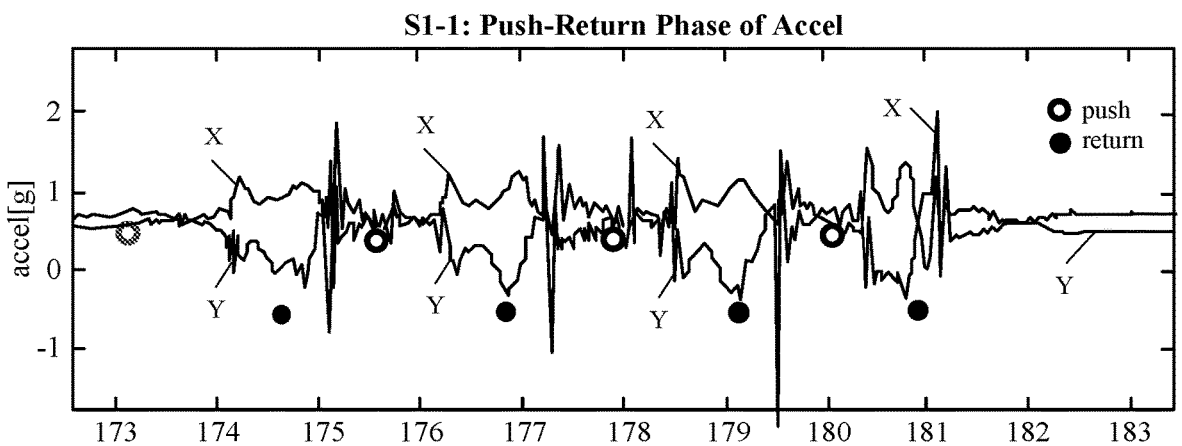
Figure 29C:
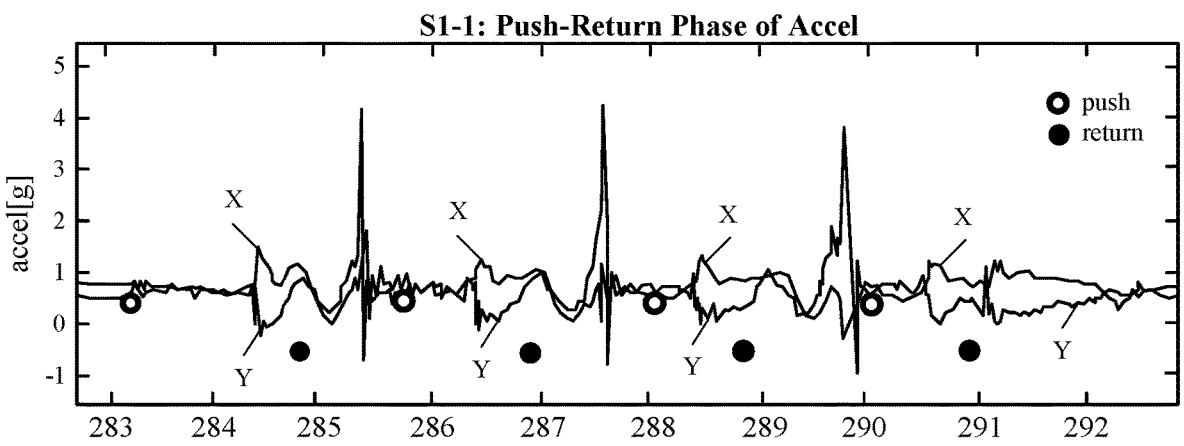

FIGS. 29A-29C illustrate X and Y accelerometer data taken during a sequence of pushes using the arc, semicircular, and single loop patterns illustrated in FIGS. 4A-4C, according to aspects of the present disclosure. The empty circles represent detected push phase, while the filled circles represent return phase. FIG. 29A is accelerometer data taken from an arc stroke type, FIG. 29B is data taken from a semi-circular stroke type, and FIG. 29C is data taken from a single loop stroke type.

Figure 30:
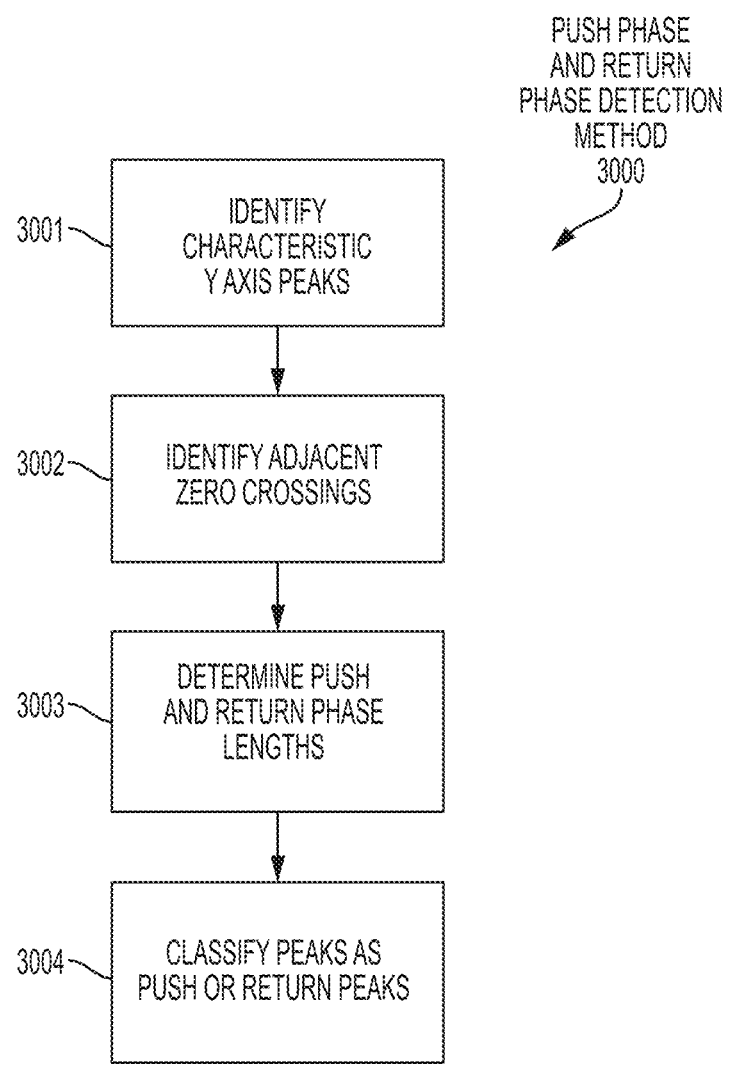
FIG. 30 illustrates a method for identifying push and return phases in accordance with aspects of the present disclosure.

The raw X, Y, and Z accelerometer is processed in two phases. FIG. 30 illustrates a method 3000 for processing accelerometer data to identify the push and return phases. In step 3001, characteristic Y axis peaks are identified. In step 3002, adjacent zero crossings are identified. In step 3003, a push phase length and a return phase length is determined. In step 3004, peaks are classified as either push or return peaks.

In step 3001, based on a detected push rate (such as a rate detected as described herein in conjunction with FIGS. 1-13), the negative peaks in the Y axis having a separation greater than that implied by the push rate are detected. For example, if the detected push rate is 1 Hz, negative Y peaks that are spaced within a window of around 1 second, or a spacing substantially similar to 1 second, are identified. For all stroke types, pushing motions are dominated by a strong negative Y axis component as the user pushes their hands forward and downward along the pushrim. The negative Y axis peaks with separation greater than that implied by the push rate thus generally correlate to the push phase motion of the hands.

In step 3002, based on the identified negative Y peaks, the Y axis zero crossings adjacent to the peak are identified. The push phase is characterized by negative Y motion, as described above. The points at which the negative Y motion begins and ends thus represent the points at which the push phase begins and ends. As a result, the zero crossing where the Y accelerometer goes from positive Y motion to negative Y motion approximately represents when the pushing motion was initiated and the zero crossing where the Y accelerometer goes from negative Y motion to positive Y motion approximately represents when the pushing motion ceased.

In step 3003, based on the identified zero-crossings, the boundaries of the push phase can be identified (as well as calculation of the time spent in push phase.) Any peaks that are not part of the push phase are part of the return phase, and the time between push phases also represents the time spent in the return phase. In step 3004, the peaks are identified and classified as push or return peaks. After identifying the push and return phases, the signs of the peaks in the return phase for the X and Y axis are identified.

FIG. 31 illustrates the characteristic return peak signs for accelerometer data in the X, Y, and Z axes for right-handed or left-handed push and return phases for the semicircular and single loop patterns. "RH" indicates that the column relates to devices worn on the right wrist, and "LH" indicates that the column relates to devices worn on the left wrist. The "SC" rows describe semi-circular strokes, while the "SLOP" rows describe single loop strokes. For each stroke type, the sequence of peak signs is indicated for both push and return phases. For example, in a semi-circular stroke type for a right wrist device, the push phase will show a positive peak followed by a pair of negative peaks on the X axis and a single negative peak in the Y axis. For the return phase, the same stroke type will show a negative peak, then a positive peak, then a weak negative peak in the X axis and a weak negative peak, then a positive peak, then a negative peak in the Y axis. For a left-wrist device, the X axis signs invert but the Y axis signs remain the same. The Z axis data is weaker and stroke classification may be performed successfully without reference to the Z axis. Optionally, Z axis data may be incorporated to refine stroke classification.

Figure 32A:
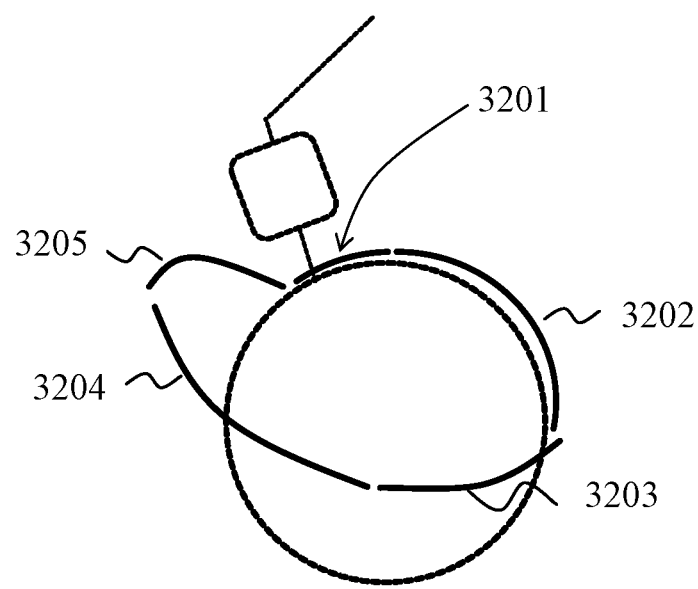
FIG. 32A illustrates the semi-circular pattern in additional detail, breaking it into five separate segments.
Figure 32B:
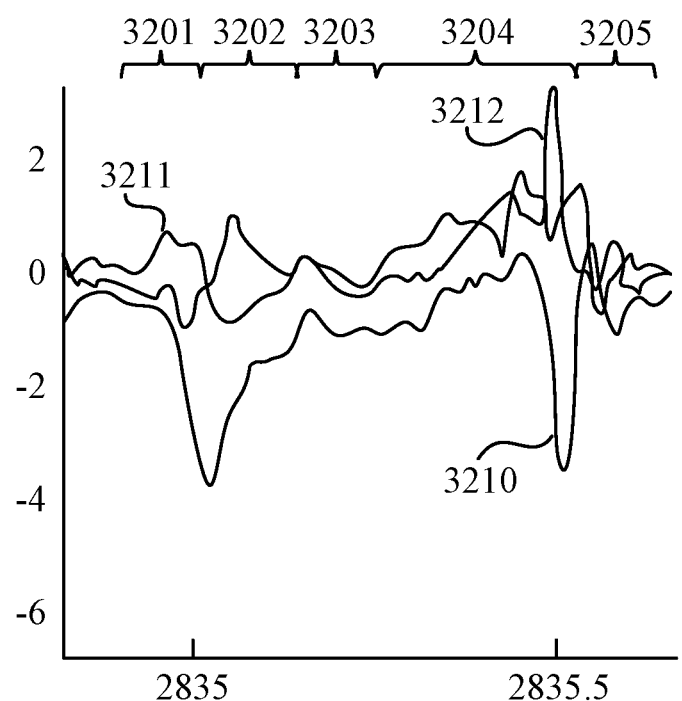
FIG. 32B shows illustrative accelerometer readings during the same semi-circular push.

FIGS. 32A and 32B provide further details of the sequence of accelerometer peak signs. FIG. 32A illustrates the semi-circular pattern in additional detail, breaking it into five separate segments. The wheelchair pushrim, wrist-worn device, and arm are illustrated using dotted lines for reference. FIG. 32B shows illustrative accelerometer readings during the same semi-circular push. In FIG. 32A, the push phase is segmented into two sub-phases. In segment 3201, the push is made along the pushrim towards the highest point of the pushrim, generating a negative Y axis acceleration and a positive X axis acceleration. Because gravity is aligned with the X axis during this sub-phase, a positive X axis acceleration is defined as an acceleration in the X axis greater than the force of gravity (i.e., greater than −1 g or +1 g, depending on the wrist on which the device is worn.) In segment 3202, the push is made forward and down along the pushrim, delivering the primary motive force, along with negative accelerations in both the X and Y axis. The return phase is also segmented, but is segmented into three sub-phases. In segment 3203, the return phase begins—the user releases the pushrim and the arm begins to return towards the back of the wheel, but continues to move downward slightly, generating a negative X axis acceleration combined with a positive Y axis acceleration. In segment 3204, the user reaches the lowest hand position, and their hand and arm begin to rise, generating a positive X axis acceleration along with a continued positive Y axis acceleration. Finally, in segment 3205, the user's hand and arm begin to swing forward and down towards gripping the pushrim, generating negative acceleration in both X and Y axis. In FIG. 32B, each segment is labeled with its corresponding identifier 3201, 3202, 3203, 3204, and 3205. X data is 3210, Y data is 3211, and Z data is 3212.

Figure 33:
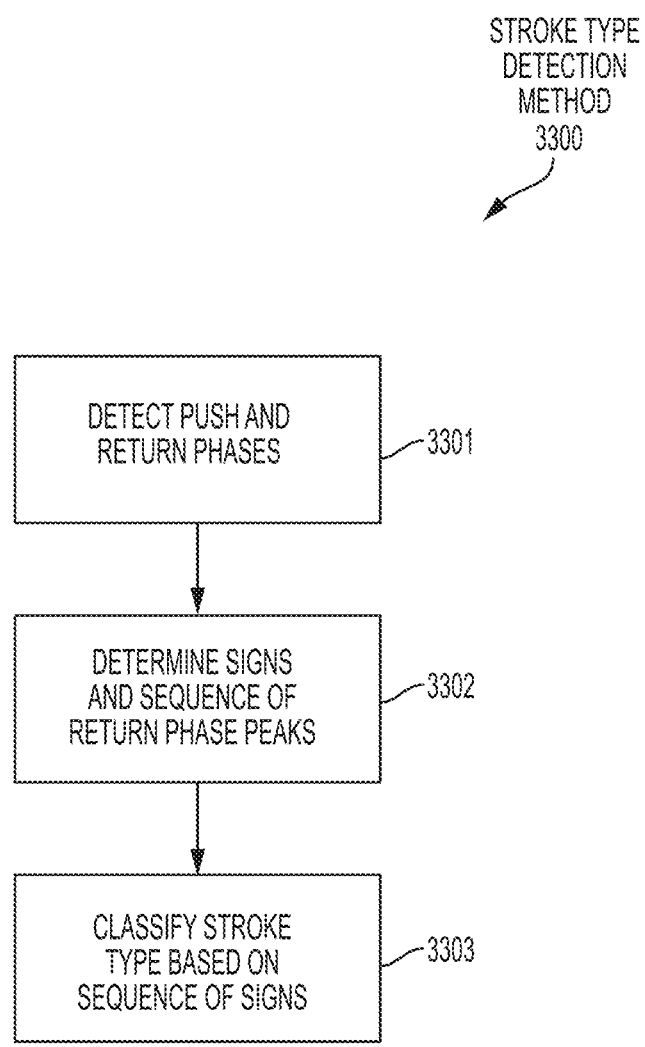
FIG. 33 illustrates a method for identifying stroke type in accordance with aspects of the present disclosure.
Figure 34:
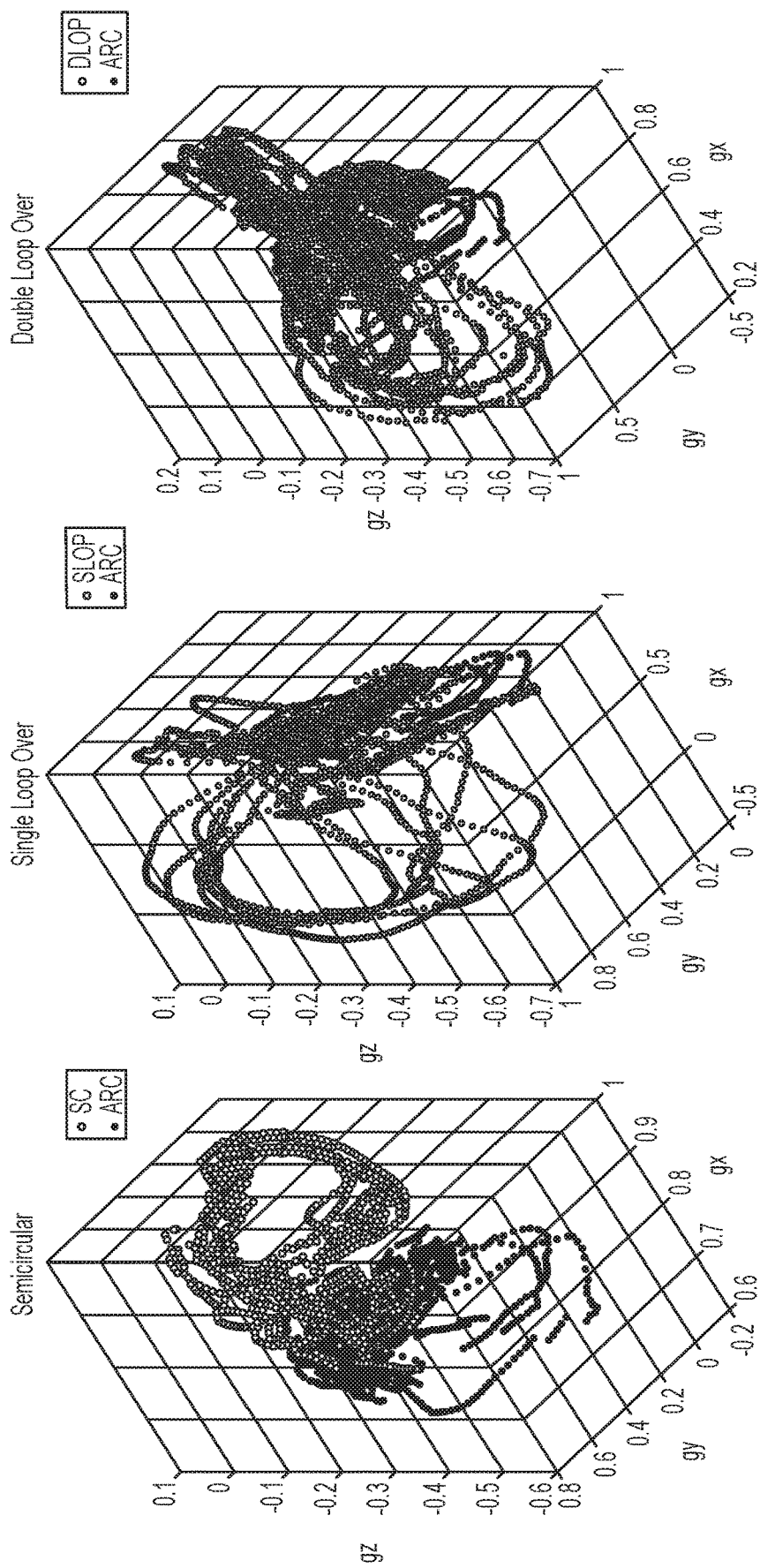
FIGS. 34A-34C illustrate the results of using accelerometer-gyro sensor fusion to detect three dimensional paths

FIG. 33 illustrates a method 3300 for identifying stroke types in accordance with aspects of the present disclosure. In step 3301, push phase classification (as described above with respect to FIG. 30) is performed, generating a classification of peaks. In step 3302, the signs of the peaks are determined and the sequence of signs in the return phase is determined. In step 3303, the sequence of signs is classified to match it to a stroke type (e.g., by identifying the appropriate sequence shown in FIG. 31.) While FIG. 31 only illustrates sequences for semi-circular and single loop stroke types, similar sequences can be determined for arc and double loop stroke types. For example, arc strokes tend to exhibit positive X and negative Y peaks during push, and then a strong positive Y peak with a strong negative X peak followed by a weak positive X peak during return.

As described above, step 3301 involves classifying the stroke into push phase and return phase, and associating accelerometer data peaks with the relevant phases. This may be done using the method described in FIG. 30.

In step 3302, the signs of the peaks are determined and the sequence of signs in the return phase is determined. This may be done simply by looking for local maximum values, using a simple threshold-based classifier in which any peak above a certain magnitude is treated as a peak, or more complex classifiers such as classifiers that look for peaks of a certain amount above the surrounding values. In a threshold classifier the threshold may be absolute, or relative based on the peak magnitude detected in the given phase or the filtered value of peak magnitudes detected in some number of recent phases. Peak detection methods such as automatic multi-scale peak detection (AMPD) can be used to locate peaks of varying amplitudes. After identifying peaks, each peak's sign (positive or negative) is determined and placed in sequence to generate a sign sequence such as ++−, −+, or similar.

Optionally, the peak classifiers described above for use in step 3302 can be replaced with classifiers that look not only at the sign but also the magnitude and distribution of peaks, or with a classifier that examines the integral of one or more axes of acceleration during various phases. For example, this may be done in order to further enhance stroke type detection. Semicircular and single loop stroke types can, depending on the exact stroke mechanics of the user, be difficult to distinguish solely based on accelerometer peak signs. Detection can be enhanced by examining features, such as by determining if the X magnitude was a sharp peak, associated with single loop, or a more evenly divided energy (potentially including two positive X peaks), associated with semicircular strokes. In another example, the integral of X energy during push phase can be taken and used for classification; the sign of the integrated data can be correlated to a stroke type. For example, single loop strokes generally spend more time in the return phase vs. the push phase as compared to semicircular strokes. Correspondingly, the X energy integral for single loop strokes will be less positive (or may even be largely negative) compared to semicircular strokes.

In step 3303, the sequence of signs is classified to match it to a stroke type (e.g., by identifying the appropriate sequence shown in FIG. 31.) The sequence of peak signs is matched to the sequence which it most closely resembles. This sequence determines the stroke type classification for that particular stroke.

FIGS. 34A-34C illustrate the results of using accelerometer-gyro sensor fusion to detect three dimensional paths. By measuring both acceleration and rotation using an accelerometer and gyroscopic sensors, a 6-degree of freedom measurement can be made providing an accurate path through 3-dimensional space. FIGS. 34A-34C illustrate the three-dimensional paths through space, with the axes of the graphic representing X, Y, and Z positions. In FIG. 34A, the lighter points represent a semicircular stroke path, while dark points illustrate an arc stroke path. In FIG. 34B, the lighter points represent a single loop stroke path, while dark points illustrate an arc stroke path. In FIG. 34C, the lighter points represent a double loop stroke path, while dark points illustrate an arc stroke path.

This path can then be classified to a stroke type by examining the actual path taken and determining which stroke type it most closely resembles (for example, by selecting the stroke type which has a minimum error between the measured path and the ideal for that stroke type, or by selecting the stroke type which has a minimum error between a distance-normalized measured path and a normalized ideal for each stroke type.) This provides an alternative method for identifying stroke type. To separate and classify these strokes, features of the 3D orbits are determined (e.g., angle of the stroke, pose angle or orientation of the device through the orbit, or circularity of motion). As gyro measurements tend to require significant battery consumption compared to accelerometer-only measurements, this method may also be used periodically to refine or correct accelerometer-only estimates or in other ways that are not constant, rather than being used on a stroke-by-stroke basis. Optionally, a magnetometer may be further incorporated to improve the 3D path accuracy.

Figure 35:
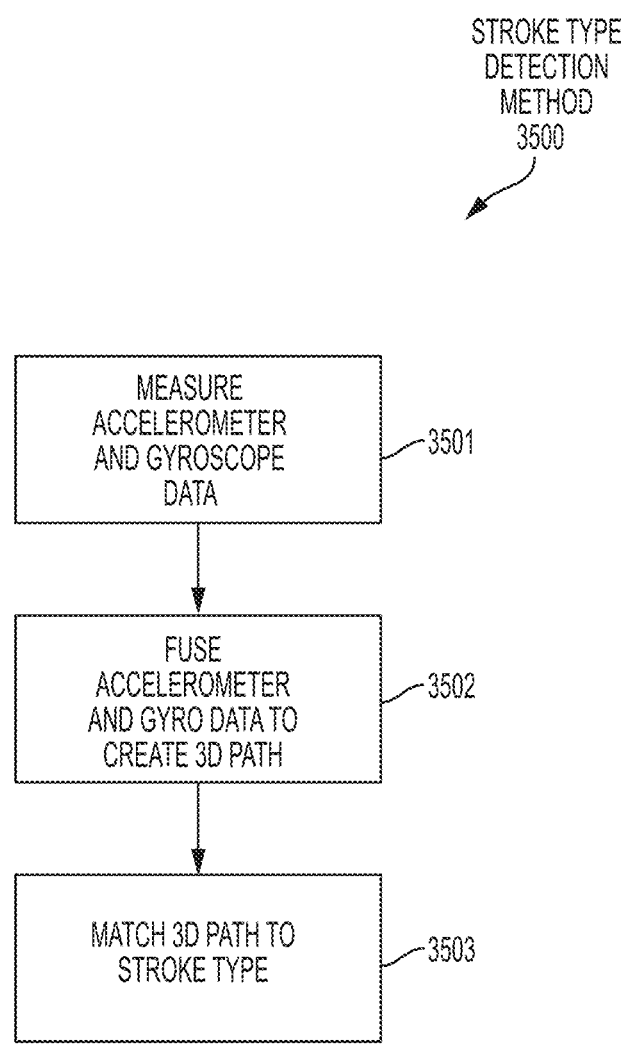
FIG. 35 illustrates another method for identifying stroke type using three dimensional path data in accordance with aspects of the present disclosure.

FIG. 35 illustrates another method 3500 for identifying stroke type using three dimensional path data in accordance with aspects of the present disclosure. In step 3501, accelerometer and gyroscopic data are measured. In step 3502, the accelerometer and gyro data are fused to create a three-dimensional path in space. In step 3503, the path is matched to a stroke type (e.g., using a minimum error or normalized minimum error technique as described above.)

Figure 36:
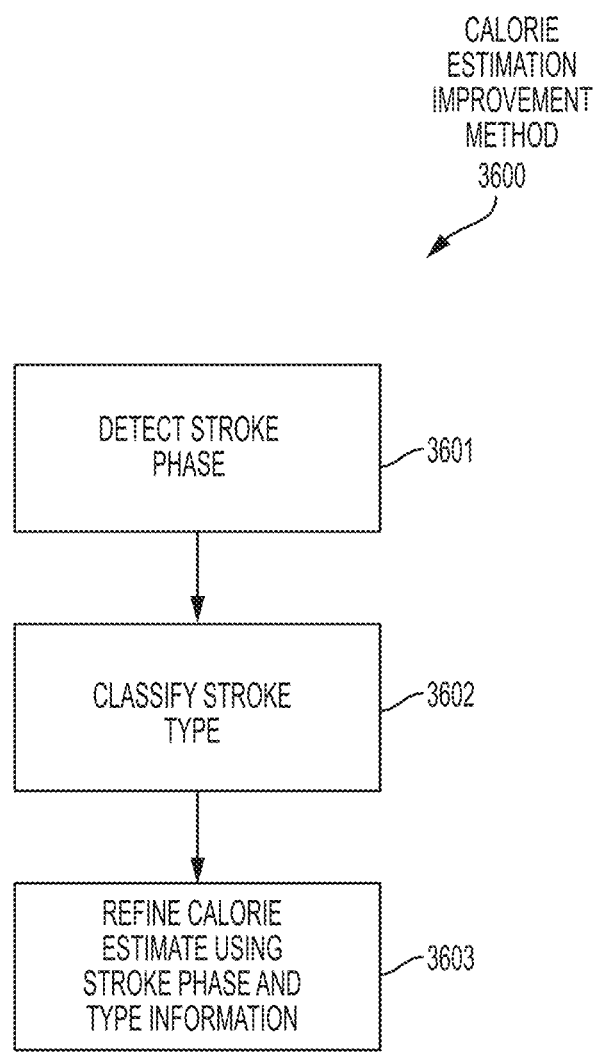
FIG. 36 illustrates a method for using the stroke phase and type estimation to improve caloric expenditure estimation.

FIG. 36 illustrates a method 3600 for using the stroke type estimation to improve caloric expenditure estimation. Each stroke type has a different mechanical efficiency. In other words, each associated set of motions for each stroke type may be more or less efficient at converting energy expenditure by the wheelchair user into wheelchair motion. As an example, the arc stroke is less efficient than the semicircular and single loop patterns. They may also have associations with injury risk or athletic ability. For example, the semicircular pattern is generally believed to be less likely to result in injuries, while the single loop pattern requires greater torso flexion and thus requires greater mobility and energy expenditure to perform the stroke. In step 3601, the stroke phase is detected as described above with respect to FIG. 33. (An analogous procedure may be employed with respect to the path data described in FIG. 34 and the technique described in FIG. 35, in which the portion of the path along a pushrim is determined and detected as the push phase and the remainder of the path is detected as the return phase, allowing determination of time spent in push and time spent in return phase.) In step 3602, the stroke type is classified (e.g., using the stroke type classifier described with respect to FIG. 33 or FIG. 35.) In step 3603, the stroke phase detected in step 3601 and/or the stroke type determined in step 3602 is used to refine an estimate of caloric expenditure for the stroke. For example, a shorter push phase with a longer return phase is associated with more energy expenditure during the push phase, as the higher expenditure produces a longer coasting motion before the user has to provide additional energy to maintain forward motion. Based on the proportion of push vs. return time and/or the stroke type (which is associated with higher or lower mechanical efficiency, as described above), a calorie estimation may be refined.

Figure 37A:
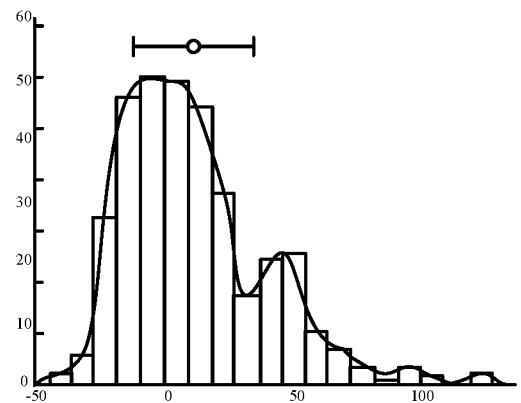
FIGS. 37A and 37B illustrate the results of refining calorie estimation error using push-return phase detection.
Figure 37B:
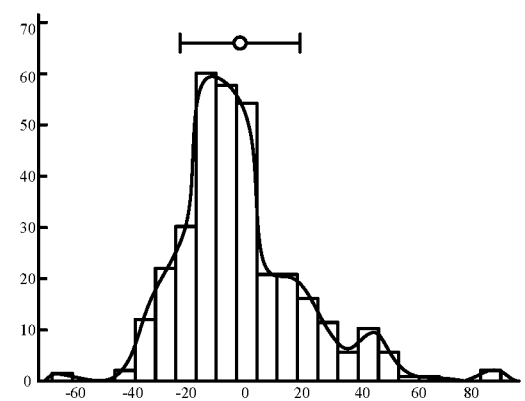

FIGS. 37A and 37B illustrate the results of this refinement. FIG. 37A is a calorie estimation error histogram for wheelchair users on flat ground when a calorie estimate is employed without a refinement such as that described with respect to FIG. 36. FIG. 37B is a calorie estimation error histogram for the same situation when a calorie estimate is refined using the techniques described herein. In some embodiments, average error may be reduced from a 5% overestimate to a 0.2% underestimate, and the 3-sigma deviation interval is reduced from +/−26.4% to +/−19.3%.

Figure 38:
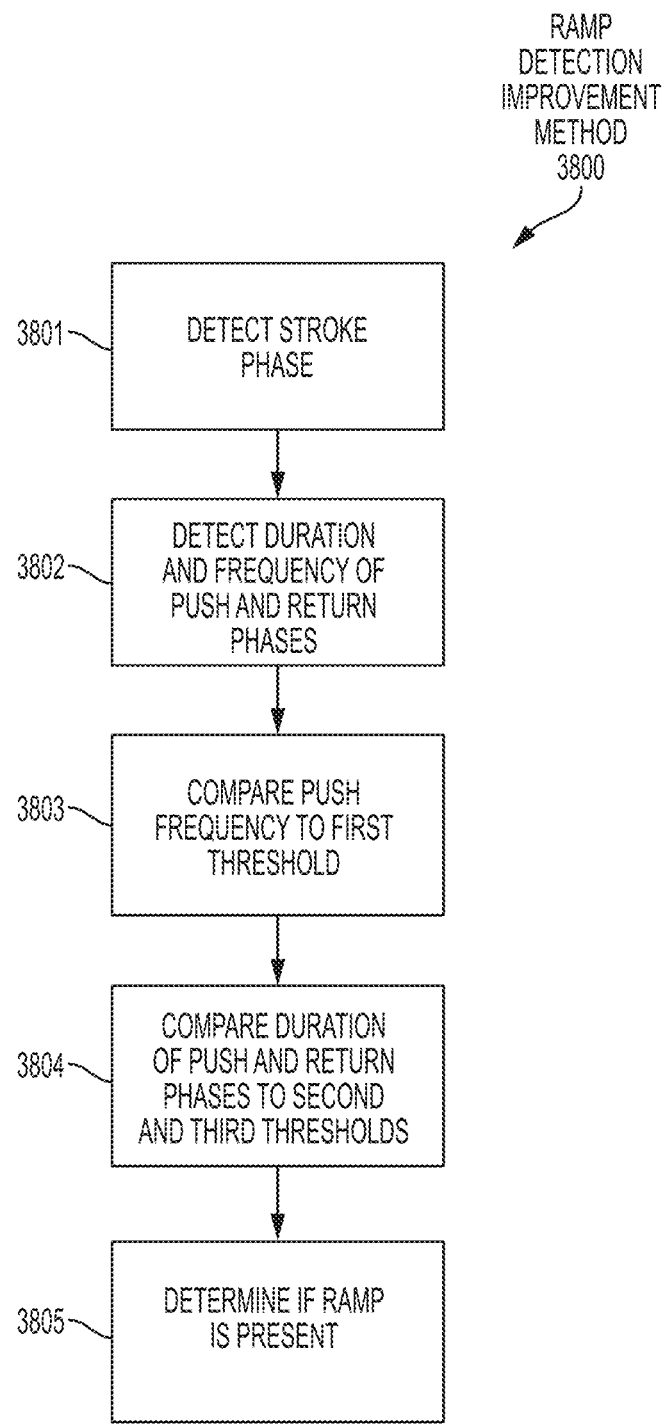
FIG. 38 illustrates a method for using the stroke phase classification to improve ramp detection.

FIG. 38 illustrates a method 3800 for using the stroke phase classification to improve ramp detection. As described above, the stroke can be separated into push and return phases. While a short push phase and long return phase can indicate larger energy expenditures, a short push phase and short return phase may indicate that instead of expending more energy per push, the wheelchair user is going up a grade such as a ramp and needs to provide more frequent inputs of energy to avoid rolling backwards. In step 3801, the stroke phase is detected as described above with respect to FIG. 33. (An analogous procedure may be employed with respect to the path data described in FIG. 34 and the technique described in FIG. 35, in which the portion of the path along a pushrim is determined and detected as the push phase and the remainder of the path is detected as the return phase, allowing determination of time spent in push and time spent in return phase.) In step 3802, the duration and frequency of push phases in combination with the duration of return phases is detected. In step 3803, the frequency of push phases is compared to a first threshold. In step 3804, the duration of push and return phases are compared to a second and a third threshold, respectively. In step 3805, a ramp determination is made. If the frequency is sufficiently high as to exceed a first threshold, and the duration of push and return phases is sufficiently low so as to be below a predetermined threshold, the method may determine that the wheelchair is on a ramp. Otherwise, the method may determine that the wheelchair is on flat ground. These thresholds can be optimized per individual by calibrating opportunistically while a user is on a ramp (as detected by, e.g., an altimeter). The changes in push frequency, push phase, and return phase can be analyzed by binning into speed and gradient increment bins, which may be used to optimize the thresholds.

Manual wheelchair users propel their wheelchairs throughout the day, and expend significant energy in doing so. Energy expenditure estimation for manual wheelchair users is complex, as there is significantly more variability in energy expenditure for a wheelchair user compared to a pedestrian. For example, there are a variety of different wheelchair stroke styles, each with its own variability in energy expenditure and a range of stroke rates with variation in time spent in push phase and return phase. The stroke style and rate used can vary based on personal preference, terrain (e.g. asphalt vs. carpet vs. grass), and environment (e.g., uphill or downhill ramps.) In addition to variations generated by the wheelchair user's technique, the wheelchair itself can generate variations in energy expenditure. Wheel size, tire pressure, chair weight, and positioning of the user within the chair all generate variation in energy expenditure.

Referring to FIGS. 39-53E, wheelchair users also may, due to injury, have varied physiology. For example, due to injury or condition type, a wheelchair user may have variations in elbow or wrist flexion that impact the motion of the arm and wrist, and more generally may have differences in range of mobility (e.g., due to a high spinal cord injury vs. a low spinal cord injury.) Heart rates, which may provide an estimate of energy expenditure, vary in response to actual energy expenditure due to conditions that typically arise in manual wheelchair user populations (such as reduced heart rate for users with spinal cord injuries above T4.) Basal metabolic rate also varies more in the wheelchair population due to other such conditions. Similarly, anaerobic caloric expenditure is increased in the wheelchair population, which can cause difficulties in establishing a calibrated reference for energy expenditure using traditional methodologies such as oxygen exchange measurement.

Figure 39:
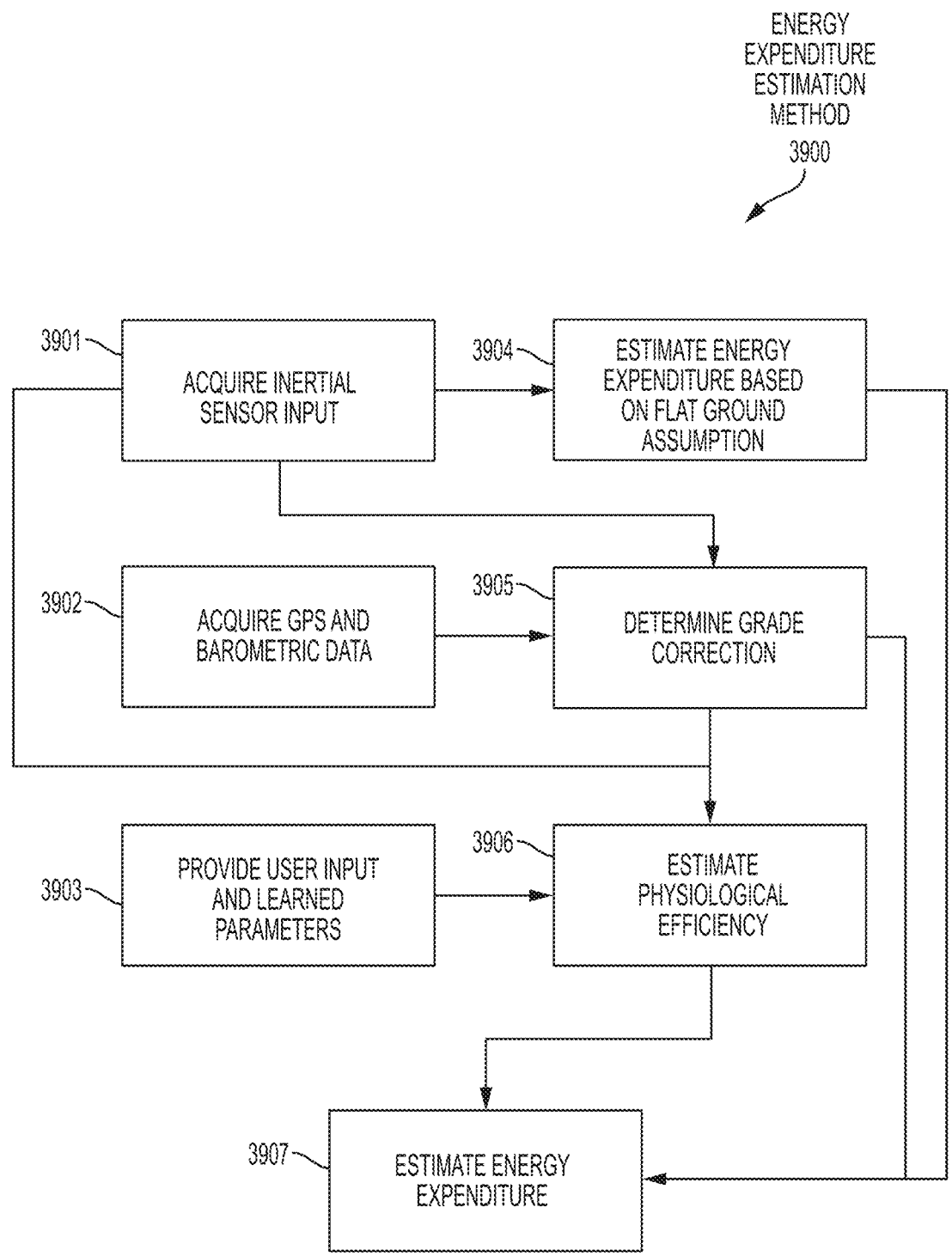
FIG. 39 provides a high level description of the techniques to be employed in improved energy expenditure estimation according to embodiments of the present disclosure.

FIG. 39 provides a high level description of the techniques to be employed in improved energy expenditure estimation according to embodiments of the present disclosure. Method 3900 for energy estimation incorporates several blocks. Block 3901 provides input from inertial sensors. Some of these sensors require low amounts of power (e.g., accelerometers) while others require more power (e.g., gyroscopes.) Block 3902 provides input from a GPS sensor to provide improved location data, including information on common locations, and a barometer to provide altitude data. Block 3903 provides user inputs and learned parameters, such as chair parameters, body metrics, known locations, known stroke type, user's physical activity level, and other such parameters. Block 3904 represents an energy-based estimation which assumes flat ground, while block 3905 represents a grade-correction block that provides an estimate of grade traveled. Block 3906 provides an estimator for physiological efficiency (i.e., the efficiency at which a user converts energy into motion.) Finally, block 3907 utilizes inputs from the other blocks in order to provide an overall estimation of energy expenditure.

Block 3901 may operate in a high power mode, in which accelerometer and gyro data is provided, or a low power mode in which only accelerometer data is provided. Similarly, block 3902 may operate in a high power mode where all data (GPS, barometer, and common location detection) is provided, or in a low power mode where only a subset of this data (or even no data) is provided. Additionally, heart rate data may be provided in high power modes to further refine data. Depending on the data being provided from blocks 3901, 3902, and 3903, blocks 3904 and 3905 may employ different techniques. For example, block 3904 may employ one stroke type and rate estimation technique if gyro data is available and another technique if gyro data is not available. Similarly, block 3905 may employ one ramp detection technique if GPS and barometer data is available, and another technique if GPS and barometer data is not available. Information on specific techniques that may be employed for stroke rate detection, ramp detection, and stroke type detection is described herein in conjunction with FIGS. 1-21 and FIGS. 28-38.

Figure 40:
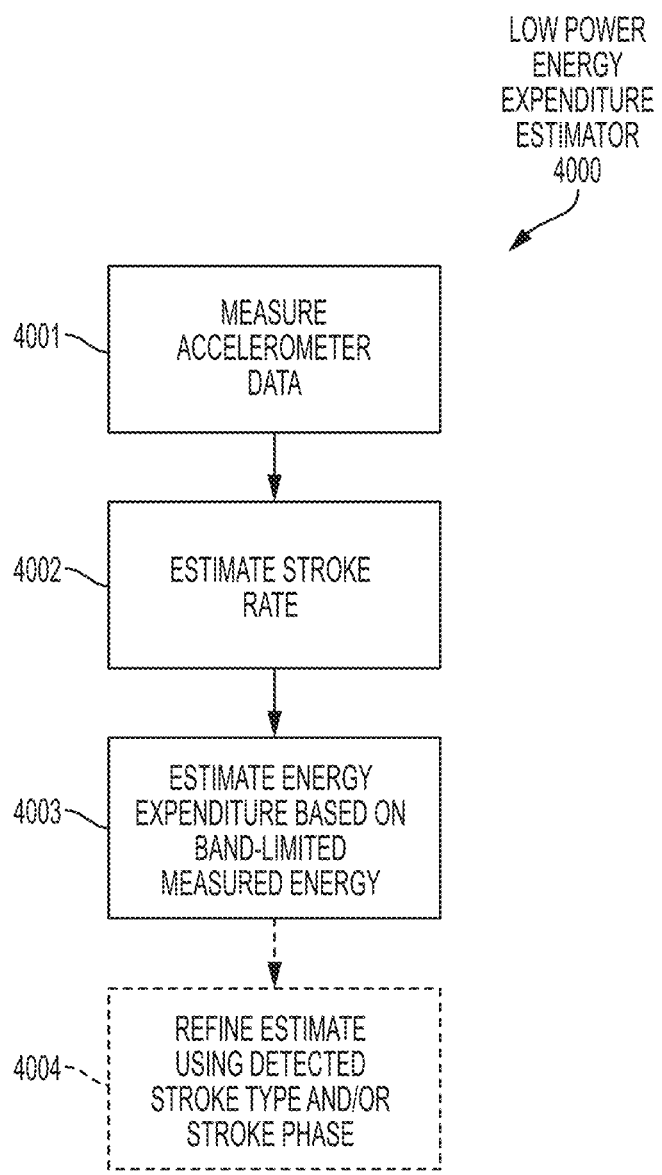
FIG. 40 illustrates a low-power energy expenditure estimator which may be used to implement one technique for block 3904.

FIG. 40 illustrates a low-power energy expenditure estimator 4000 which may be used to implement one technique for block 3904. This estimator estimates energy based on the assumption of flat ground. Block 4001 provides accelerometer data, which may be used to determine an estimate of stroke rate in block 4002. Based on the accelerometer data and stroke rate, block 4003 sums measured accelerometer energy over a dynamically selected frequency band (typically within the band of frequencies ranging from 0.25 to 4 Hz) and creates an estimation of energy expenditure based on that measured energy within the band. For example, the amount of energy in the frequency band may be linearly interpolated to an energy estimate. In some embodiments, this is done by multiplying the energy within the frequency band on the X axis by a coefficient ranging from 0.4 to 0.6, and adding a constant value that ranges from 0.25 to 0.5 to produce an estimated speed in m/s. The coefficients may vary to produce estimated speeds in other units. In one embodiment, this is done by multiplying the energy within the frequency band on the X axis by 0.467 and adding a constant value of 0.3694 to produce an estimated speed in m/s. In some embodiments, the estimated speed is then taken as an input, scaled by a coefficient that may range from 0.85 to 1.0, and added to a constant ranging from 1.5 to 2.0 to produce an estimated number of METs. In a specific embodiment, the estimated speed is taken as an input and scaled by 0.9308, and then a constant value of 1.8885 is added, resulting in an estimated number of Metabolic Equivalent of Tasks (METs). A MET is defined as the amount of energy expended by the individual while seated at rest. These coefficients may also be adapted to fit users or equipment. This estimate may also be refined in block 4004 by using a detected stroke type and/or push/return phase (e.g., as described herein in conjunction with FIGS. 28-38) to refine the energy expenditure based on varying physiological efficiencies of different stroke types. The estimator described in FIG. 40 requires only low-power inputs and can be run continuously with limited impact on battery life.

Figure 41:
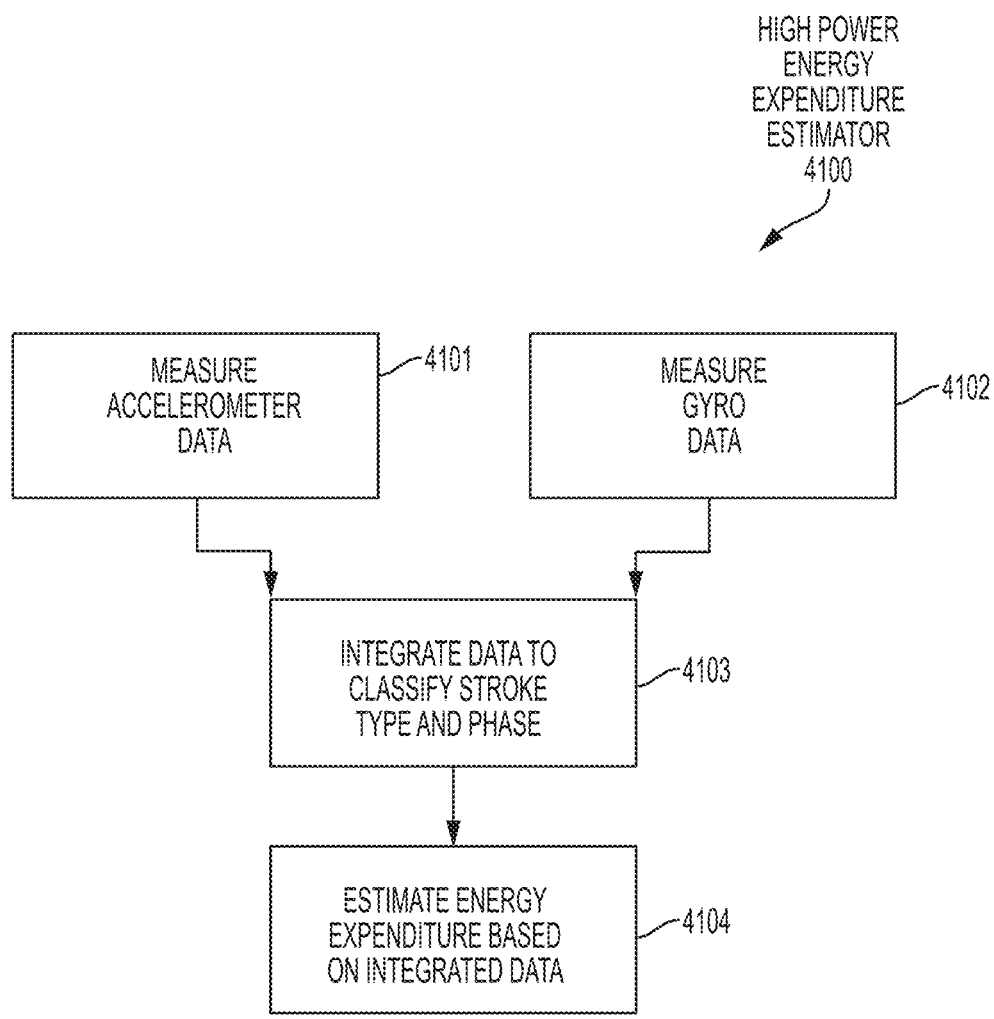
FIG. 41 illustrates a high-power energy expenditure estimator which may be used to implement another technique for block 3904.

FIG. 41 illustrates a high-power energy expenditure estimator which may be used to implement another technique for block 3904. This estimator also estimates energy based on the assumption of flat ground. Block 4101 provides accelerometer data and block 4102 provides gyro data. Block 4103 integrates this data to determine the quaternion of the movement of the user's arm, thereby providing classification of stroke pattern and push/return phase. Block 4104 then uses the movement data (i.e., stroke rate, pattern, and push/return phase) to generate an estimate of energy expended by the user. The estimator described in FIG. 41 relies on gyro data, which is relatively high-power, and may be gated on and off based on user-selected workouts, on detection of the start of a period of high energy expenditure, or based on an allowance from the device control system allowing the use of increased power. For example, if the low-power estimator described in FIG. 40 detects a period of high energy expenditure, the high-power estimator described in FIG. 41 may be initiated and used until energy expenditure drops below a threshold.

As an alternative or additional refinement to the estimators described above, a GPS-based estimator may be employed to implement block 3904. In a GPS-based estimator, the GPS speed is used as the baseline input, and the MET estimate is a quadratic equation using GPS speed as the input. In some embodiments, the square of the GPS speed is multiplied by a coefficient in the range of 0.5 to 0.9, and then the GPS speed is multiplied by a coefficient in the range of 0.9 to 1.1 and subtracted. Afterwards, a constant coefficient ranging from 1.75 to 2.75 is added to provide an estimated number of METs expended. In one specific embodiment, the GPS speed is multiplied by 0.94 and subtracted from the square of the GPS speed multiplied by 0.7. A constant value of 2.3 is added, to provide an estimated number of METs expended from GPS speed. This estimate may be used directly, or may be fused with an accelerometer or accelerometer+gyro estimate (e.g., by averaging.)

Figure 42:
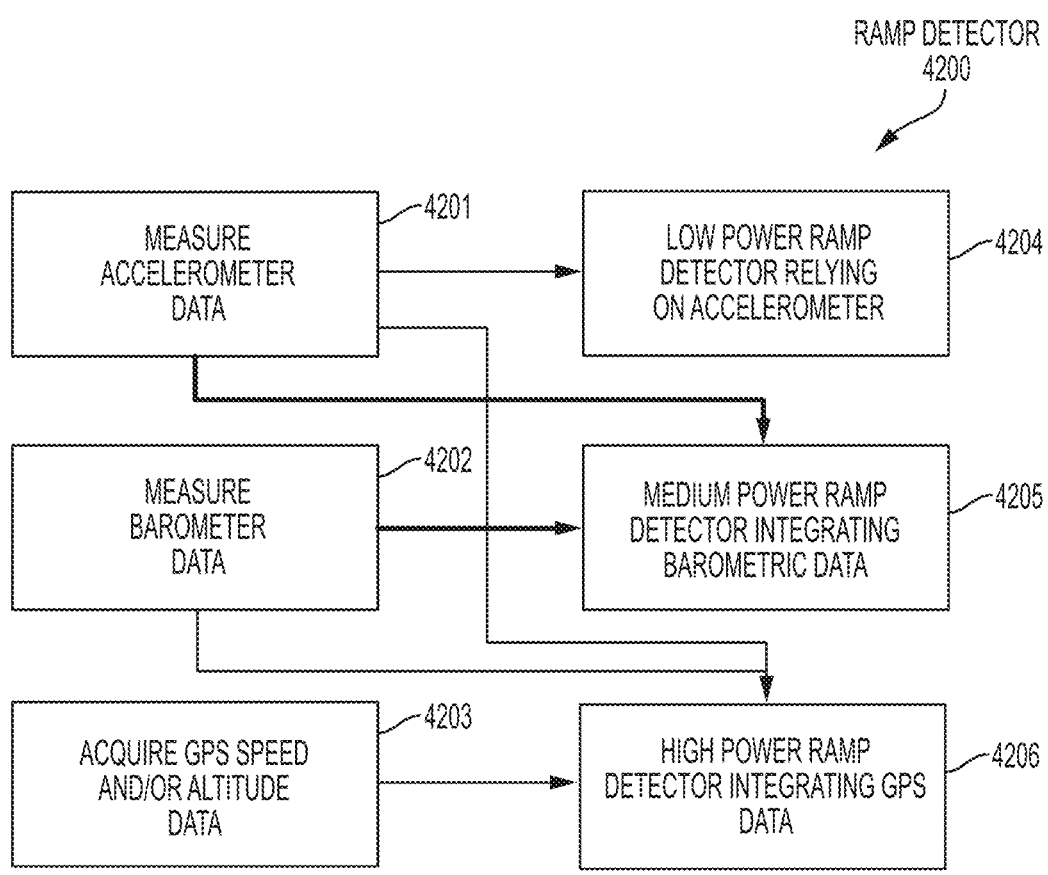
FIG. 42 illustrates a switchable high and low power ramp detector according to embodiments of the present disclosure which may be used to implement block 3905.

FIG. 42 illustrates a switchable high, medium, and low power ramp detector 4200 according to embodiments of the present disclosure which may be used to implement block 3905. In block 4201, accelerometer input is received. In block 4202, barometer input is received, and in block 4203, GPS speed and/or altitude information is received. Based on desired energy expenditure, either block 4204, block 4205, or block 4206 may be used to integrate some or all of this data to detect when the user traverses a ramp. For example, in a low power mode 4204, only the accelerometer data of block 4201 may be employed (for example, as described herein in conjunction with FIGS. 14-21.) In a medium power mode 4205, barometer data may also be measured and integrated, refining the accelerometer-based ramp detection technique. Finally, in a high power mode 4206, GPS data may be integrated as well, allowing additional refinement. For example, if the accelerometer data reflects a low stroke energy and/or a low push count, but GPS speed is increasing, the user is likely traversing a downhill ramp (or alternately, a companion may be pushing the wheelchair.) In either instance, caloric expenditure is reduced. In contrast, if a high stroke energy is detected and/or a high stroke rate is detected, but GPS speed decreases or remains constant, the user is likely either on a ramp or else is traversing terrain requiring higher energy expenditure (e.g., grass) and should be rewarded for the increased caloric expenditure. This may be further refined using the stroke phase detectors described above, as a higher ratio of push to return phase is indicative of increased energy expenditure to overcome resistance from grade or terrain.

Regardless of power mode, the technique of FIG. 42 may output either an indication that a ramp has been detected, or an estimation of increased (or decreased) energy expenditure from the ramp. For example, an estimator may produce a MET estimate based on the estimated METs assuming flat ground produced by block 3904 and vertical speed. In one embodiment of the present disclosure, this is done by multiplying the vertical speed by 4.4 and the MET estimate from flat ground by 2.4.

An individual wheelchair user may also have varying physiological efficiency depending on their physical activity level (i.e., physical fitness), mobility level (e.g., physical flexibility and range of motion), and injury type (e.g., spinal cord injury vs. amputation), as well as the specific activity they are engaging in. One mechanism for obtaining this information is to ask the user to describe their fitness level, mobility level, and injury type. However, this is subject to the accuracy of the user's description of their levels of fitness and mobility. Alternately, this may be estimated based on measured data (e.g., correlation of accelerometer and GPS data over time with metrics such as measured heart rate.) These parameters can significantly affect the user's physiological efficiency and overall energy expenditure. Basal metabolic rate may vary significantly in a wheelchair user, as they have lower basal caloric burn from legs due to atrophy (or even, as in the case of an amputation, non-existence.) This can also affect user mass which itself can affect energy expenditure because pushing a lower mass requires less energy expenditure. Heart rate itself can also illustrate user fitness level. Depending on factors such as age, condition, and injury type, a user may have a reduced (due to condition and fitness level) or increased (due to condition or injury type) resting heart rate or maximum heart rate while exercising or expending energy. The ratio between observed heart rate and predicted maximum heart rate (e.g. based on user age and weight, or age, weight, and fitness level) for a given activity with a known observable work rate (speed and grade) can provide an estimate of physiological efficiency. A higher ratio implies lower efficiency, which implies that the user is working harder for a given set of observable parameters and their energy expenditure estimate should be increased to reflect this. Similarly, a lower ratio implies that the user is not working as hard and their energy expenditure may be decreased.

In addition to user-specific characteristics, activity characteristics can also impact physiological efficiency. For example, when users propel wheelchairs at very high speeds, biomechanical efficiency (and thus physiological efficiency) is reduced, such that intensity of energy expenditure may increase non-linearly with speed. Similarly, when a user propels a wheelchair up a steep grade (particularly at 4+ degrees of grade), reduced efficiency is observed due to the change in mechanics required to avoid rolling backwards.

Figure 43:
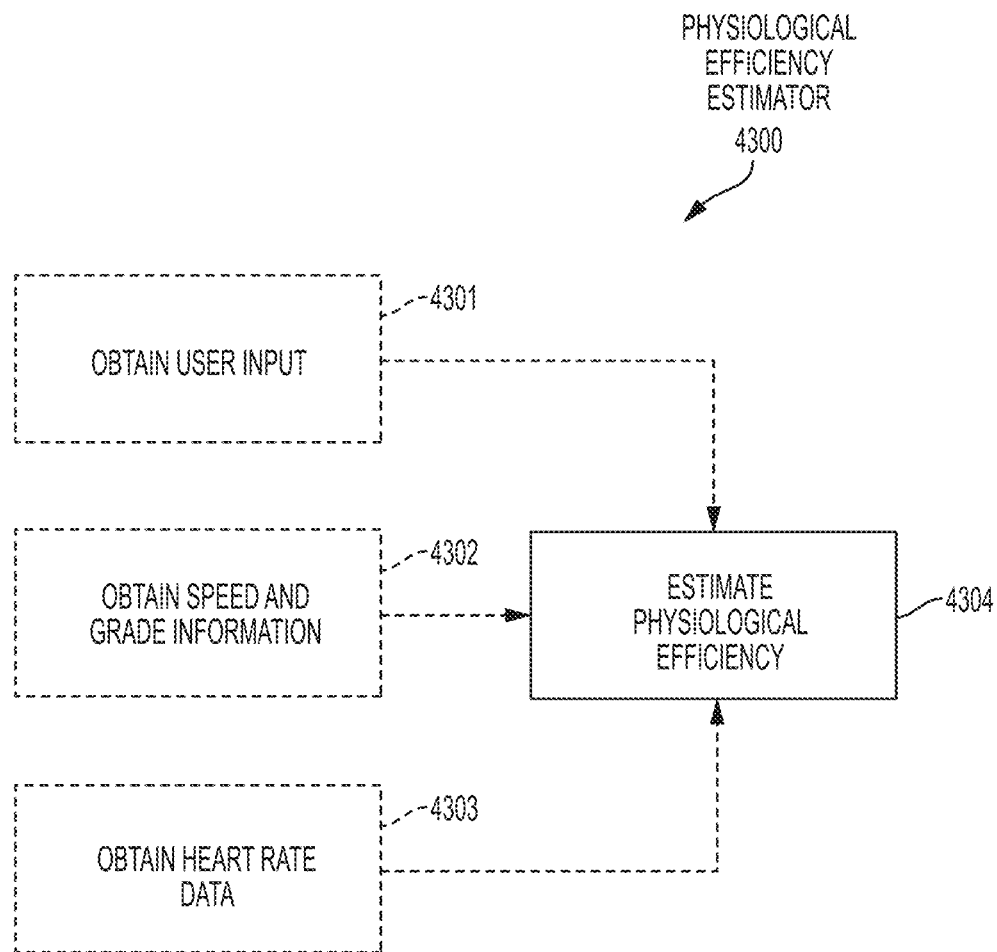
FIG. 43 illustrates a physiological efficiency estimator which may be used to implement block 3906 in some embodiments of the present disclosure.

FIG. 43 illustrates a physiological efficiency estimator which may be used to implement block 3906 in some embodiments of the present disclosure. In block 4301, user input as to characteristics such as age, weight, fitness level, mobility level, and injury type is obtained. In block 4302, speed and grade information is obtained (e.g. based on stroke rate and type, GPS data, barometer data, or ramp detection data.) In block 4303, heart rate data is obtained. In block 4304, the information obtained in blocks 4301-4303 is correlated to determine an overall estimate of physiological efficiency to provide a correction to any energy expenditure estimates. For example, a high spinal cord injury user will tend to have lower caloric burn (as they are less able to recruit muscles for activity). Basal metabolic rate estimates may be influenced as well, as described above. The correction may correct a baseline value, correct a scaling coefficient, and/or select between multiple energy expenditure models, depending on the specific inputs. Depending on power constraints or user inputs, some of the data sources may be unavailable. (Data sources that are not always available are indicated in FIG. 43 with dashes, while data sources that can be assumed to be available are shown with solid lines.) For example, in a low energy mode, GPS and heart rate data may be unavailable. Even in a high power mode, a user may not have input their injury type, and that data might be unavailable. The efficiency estimator may use whichever data is available to it to provide a refined estimate of energy expenditure efficiency.

Figure 44:
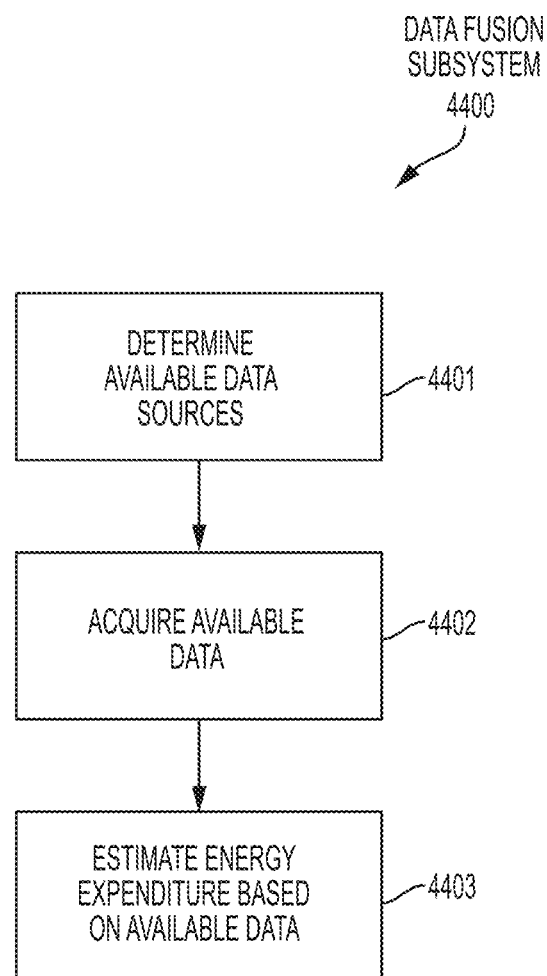
FIG. 44 illustrates a data fusion subsystem which may be used to implement block 3907 in some embodiments of the present disclosure.

FIG. 44 illustrates a data fusion subsystem which may be used to implement block 3907 in some embodiments of the present disclosure. In block 4401, the available sources of data are determined. In block 4402, available data is acquired from available data sources. In block 4403, the available data are used to create an estimated energy expenditure. This fusion may be done using a number of techniques, such as a decision tree, a Bayesian model, logistic regression, state machines, or vector machines.

FIG. 45 illustrates one such technique, a decision matrix. Depending on whether GPS/altimeter data is available, and if it is available, the measured GPS speed, as well as based on determined ramp, different estimation models are employed. For example, if GPS and altimeter data are both available, and the model indicates a flat or unknown grade, then the GPS speed model will be employed. If an uphill ramp is indicated, then the GPS speed model may be used to produce a flat MET estimate, corrected using the GPS vertical speed (or alternately the altimeter/barometer vertical speed), as described above with respect to FIG. 40. If a downhill ramp is indicated, then the GPS-based model may be ignored (as it will incorrectly credit the user for speed obtained from the ramp) and instead only METs determined via accelerometer data for push energy will be credited, as described above with respect to FIG. 38. If GPS and/or altimeter/barometer data are unavailable, then the model may only employ the push energy estimator described above with respect to FIG. 40, or the push estimator described above with respect to FIG. 40 in combination with an accelerometer-only ramp detector for the uphill case.

In addition, if GPS speed is low, then instead of using an energy based estimator or speed based estimator, the user may simply be credited with minimal motion METs or with their basal metabolic rate METs. In one embodiment, if the user is below 0.3 m/s in GPS speed, they are credited with their resting MET value, while in another embodiment, if the user is above 0.3 m/s but below 0.5 m/s, they are credited with a minimal moving MET amount. In one embodiment, the minimal moving MET is 1.5 METs.

In addition, range checking may be employed to prevent spurious data. For example, MET estimates may be bounded to be no less than 1.5 METs and no more than 16 METs. Similarly, speed estimates may be bounded—vertical speed may be limited to no more than 2.0 m/s, and GPS speeds over 8 m/s (the sprinting record) may be bounded to 8 m/s.

FIG. 46 illustrates a similar decision matrix which may be employed in grade determination. If GPS data is available, an estimator that uses GPS speed and a push count/energy threshold approach may be employed. If GPS data is not available but barometer or altimeter data is available, either an altimeter threshold approach (where the barometer or altimeter data regarding change in height (deltaH) changing by more than a threshold amount) may be employed, or the ramp detection approach described herein in conjunction with FIGS. 14-21 may be employed. If neither GPS nor barometer/altimeter data is available, the ramp detection approach described herein in conjunction with FIGS. 14-21 may be employed. Based on the determination from this, either an uphill or downhill estimate will be produced, potentially including a vertical speed estimate.

FIGS. 47-53 illustrate data regarding embodiments of the present disclosure.

Figure 47:
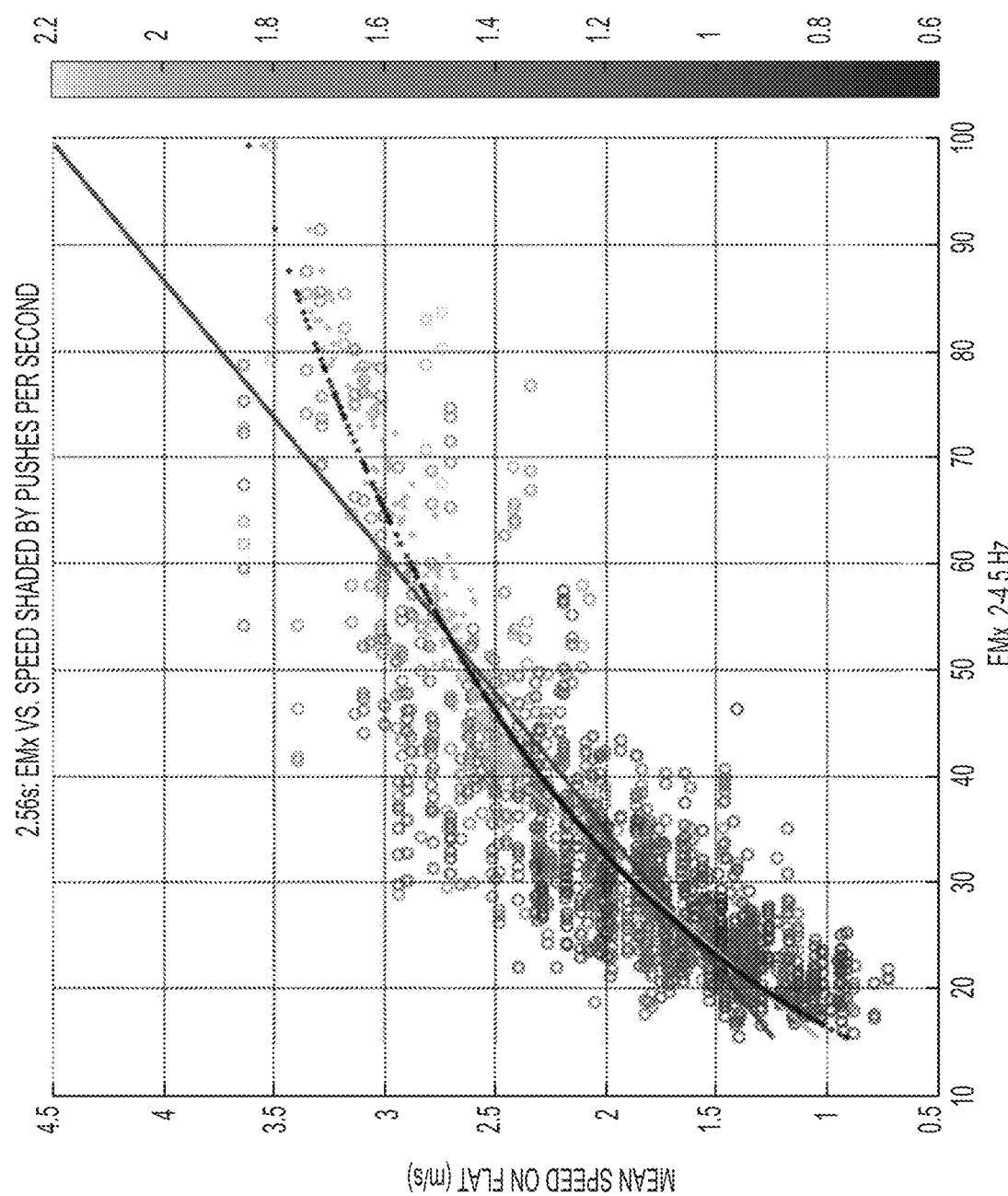
FIG. 47 illustrates measured data showing the correlation between measured energy and speed.

FIG. 47 illustrates measured data showing the correlation between measured energy within the 0.2 to 4.5 Hz frequency band in the X axis and mean speed of the wheelchair user on a flat surface, along with linear and quadratic fits. This data illustrates the data underlying the speed estimator described above with respect to FIG. 40.

Figure 48:
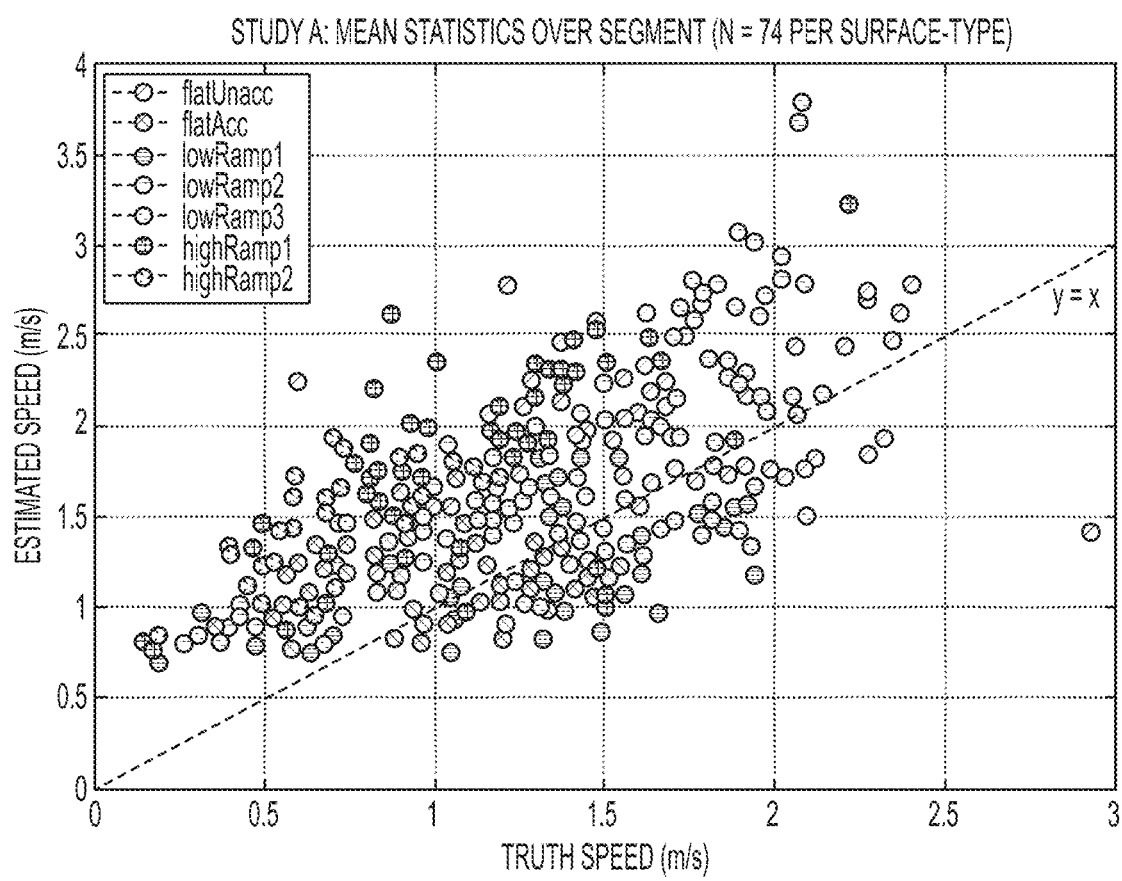
FIG. 48 illustrates actual speed vs. estimated speed (uncorrected for ramp presence) on a variety of segments.

FIG. 48 illustrates actual speed vs. estimated speed (uncorrected for ramp presence) estimated using an estimator similar to the one described above with respect to FIG. 40, with the samples shaded based on the presence of a ramp. The estimator overestimates actual speed for ramps, due to the higher energy expenditure required (which is not reflected in a higher speed due to the energy used to overcome the incline). Because of this difference in energy expenditure for the same actual speed, purely speed based estimators (such as GPS trackers) will provide different results to estimators that examine work rate (such as the accelerometer-based estimator of FIG. 40.)

Figure 49:
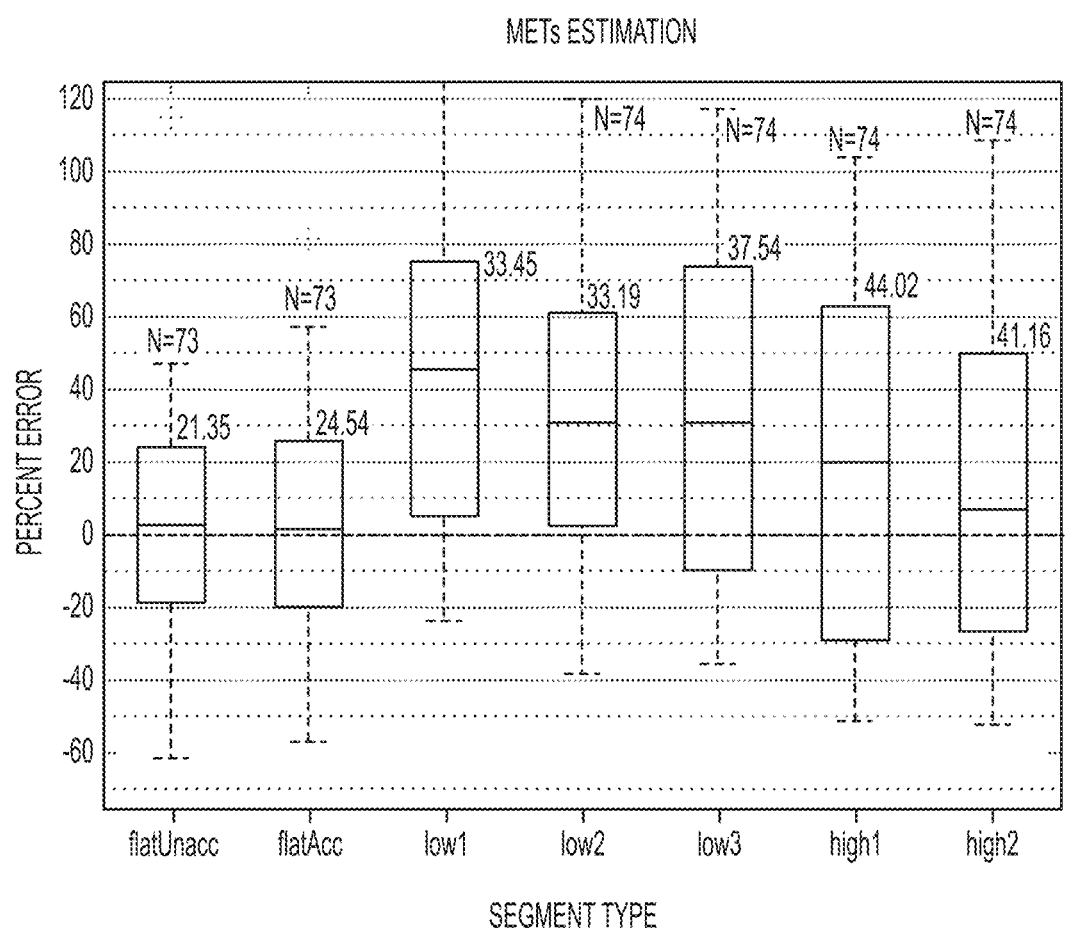
FIG. 49 illustrates error bars for various segment types for the uncorrected energy estimator.

FIG. 49 illustrates error bars for various segment types for the uncorrected energy estimator. Low ramps are overestimated. Flat segments have a roughly zero mean. High ramps also have a roughly zero mean, but tend to err towards over-estimation. For example, for data estimated based on 73 wheelchair users traversing a flat unaccompanied segment (flatUnacc), the mean error is approximately −2.5 and the standard deviation is 21.36. For data estimated based on 73 users traversing a flat accompanied (flatAcc) segment (i.e., a segment in which a wheelchair user has a friend walking near them, which can bias a wheelchair user into specific stroke types or patterns), the mean error is approximately +1 and the standard deviation is 24.54. In contrast, 74 users on various low ramp segments (lowRamp1, lowRamp2, and lowRamp3) produced mean errors of approximately +45, +30, and +27 percent, respectively, with standard deviations of 33.45, 33.19, and 37.64. Low ramps thus produce consistently over-estimated energy expenditures. The three segments represent users going up a low ramp at slow, medium, or fast speeds. 74 users on two different high ramp segments (highRamp1 and highRamp2) produced mean errors of approximately 0; however, it also produced standard deviations of 44.02 and 41.16. The high ramp segments represent users going up a high ramp two different times, but do not differ in speed. In other words, a ramp-agnostic estimator produced results that were accurate on average for both no ramp and high ramp scenarios, but with significantly higher standard deviations for high ramp scenarios, while low ramp scenarios produced significant errors in average estimate and an intermediate amount of standard deviation. These bars do not illustrate the distribution of errors, which is also meaningful; the shape is shown in FIGS. 50A-50G.

FIGS. 50A-50G illustrate the probability density function (PDF) of errors in the speed estimate for various types of surfaces. These PDFs provide an alternative visualization of the error bars of FIG. 49. FIG. 50A illustrates the PDF for a flat unaccompanied segment. FIG. 50B illustrates the PDF for a flat accompanied segment. FIG. 50C illustrates the PDF for a first low ramp segment. FIG. 50D illustrates the PDF for a second low ramp segment. FIG. 50E illustrates the PDF for a third low ramp segment. FIG. 50F illustrates the PDF for a first high ramp segment. FIG. 50G illustrates the PDF for a second high ramp segment.

Figure 51:
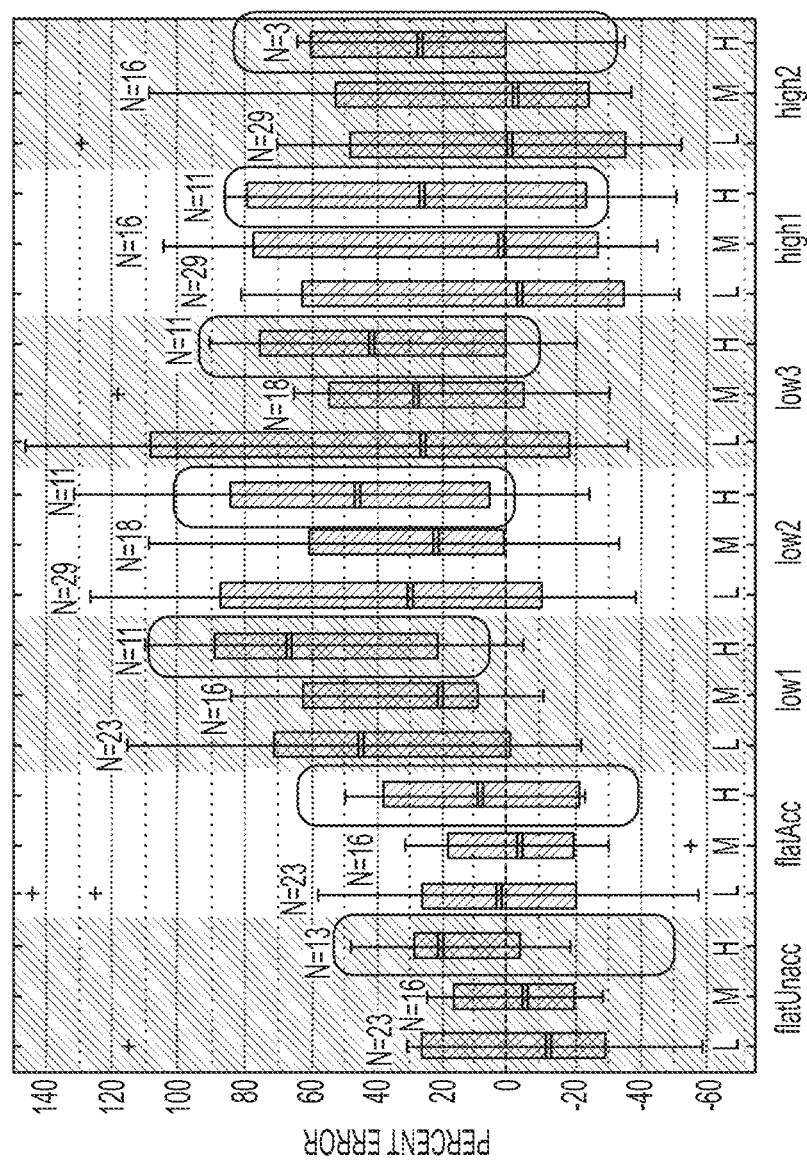
FIG. 51 illustrates data showing the error in the uncorrected estimate separated by injury type.

FIG. 51 illustrates data showing error in uncorrected estimate separated by injury type—low spinal cord injuries, mid-spinal cord injuries, and high spinal cord injuries. While low and mid SCIs have relatively similar estimation characteristics, high SCI wheelchair users consistently overestimated energy expenditure compared to low or medium SCI users. This consistent overestimate allows for the correction of caloric expenditure for high SCI users.

Figure 52:
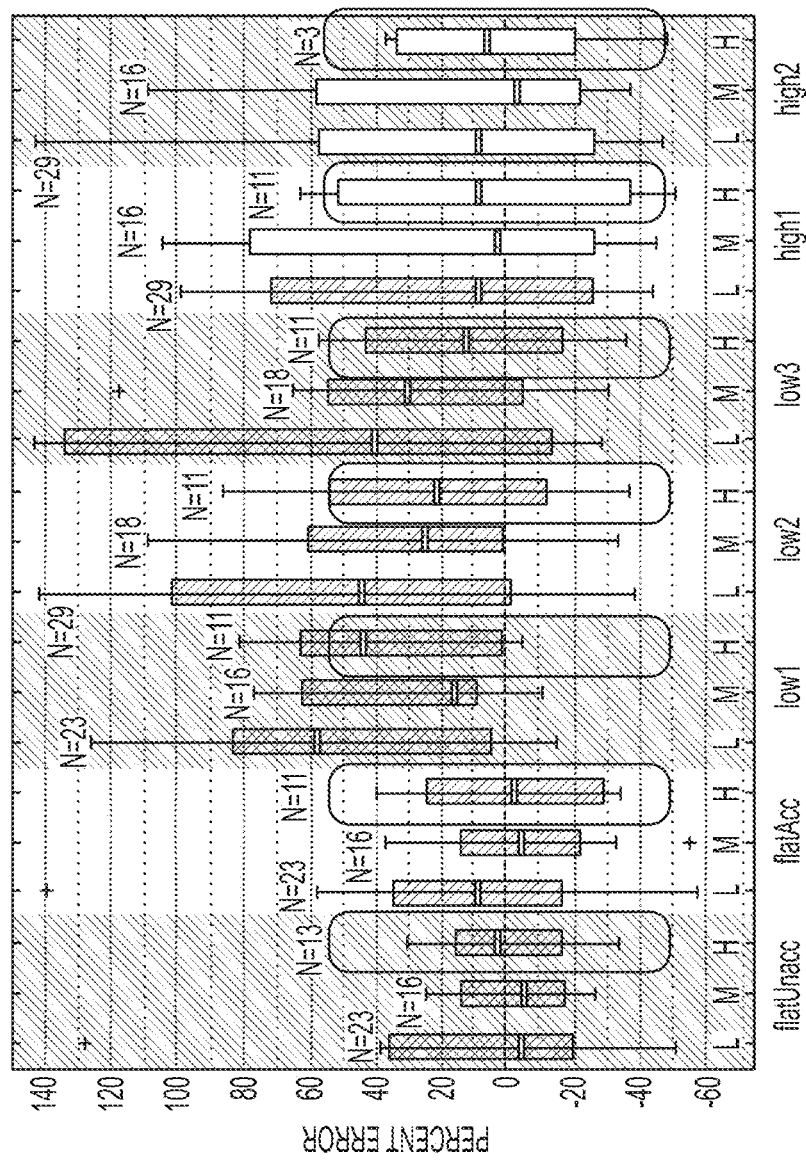
FIG. 52 illustrates the results of retrained estimators based on injury type.

FIG. 52 illustrates the results of retrained estimators based on injury type. Instead of a baseline estimator (e.g., the METs=0.9308*estimated speed+1.8885 estimator described above with respect to FIG. 38), injury-specific estimators are employed. The conversion from energy to estimated speed described above with respect to FIG. 38 is used, but instead of the 0.9308 and 1.8885 slope and intercept, a low SCI may use a slope of 1.1951 and an intercept of 1.7827 (or a slope in the range of 1 to 1.4 and an intercept in the range of 1.6 to 2.0), a mid SCI may use a slope of 1.1152 and an intercept of 1.6023 (or another slope in the range of 1 to 1.2 and an intercept in the range of 1.5 to 1.7), and a high SCI may use a slope of 0.2953 and an intercept of 2.2553 (or another slope in the range of 0.2 to 0.4 and an intercept in the range of 2 to 2.5.) Using these retrained estimators, the mean error for high SCI injuries is brought in line with the mean error for other SCI injuries, and the overall mean error is reduced for all injury types.

Figures 53A, 53B:
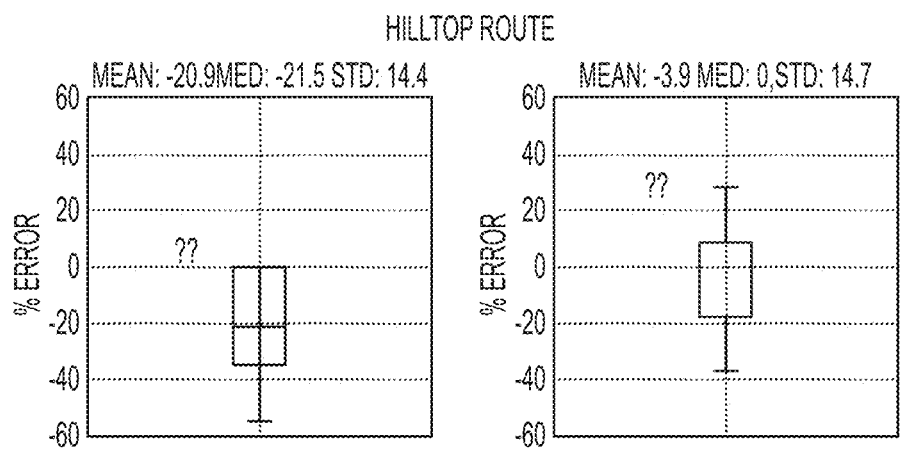
FIGS. 53A-53E illustrate the impact of grade correction on the estimator.
Figures 53C, 53D:
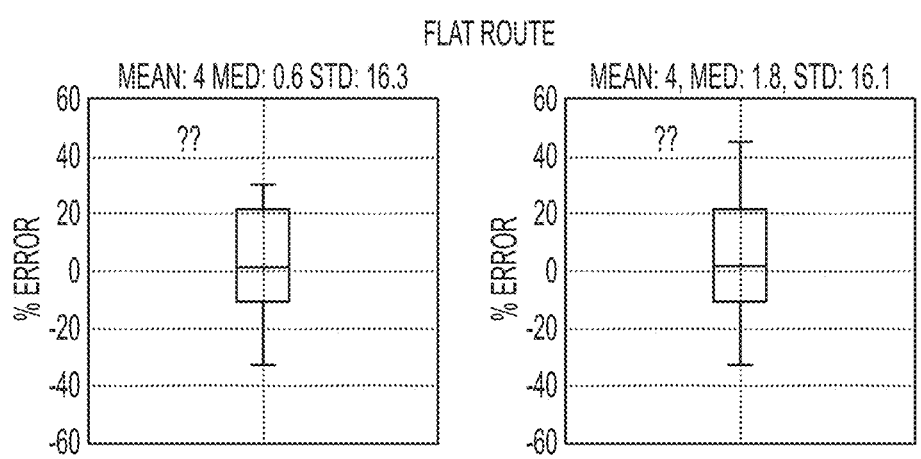
Figure 53E:
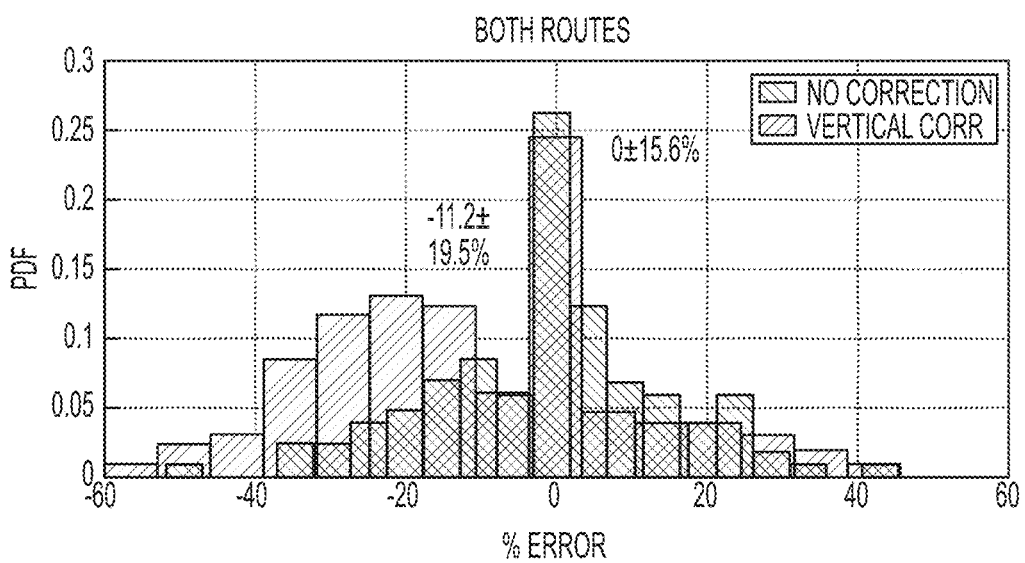

FIGS. 53A-53E illustrate the impact of grade correction on the estimator. FIG. 53A shows the error bars for an uncorrected estimator used on a route going over hills. FIG. 53B shows the error bars for a corrected estimator used on the same route. Similarly, FIGS. 53C and 53D show the error bars for an uncorrected and corrected estimator, but used on a flat route. This illustrates that the error in FIG. 53A is due to the use of an uncorrected estimator on a hilly route. Finally, FIG. 53E illustrates the probability distribution function for both an uncorrected and corrected estimator, showing that the error distribution has a zero mean and reduces the standard deviation of error to +/−15.6% when a corrected estimator is employed, as opposed to a mean of −11.2 and a standard deviation of error of +/−19.5% when an uncorrected estimator is employed.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

Methods described herein may represent processing that occurs within a wearable device (e.g., device 100 of FIG. 1) and/or within a companion device (e.g., device 300 of FIG. 3). In many embodiments, processing may be performed by a processor circuit within the wearable/companion device. In some embodiments, processing may be performed using computer software instructions executed upon a computer processor. In particular embodiments, the computer software instructions may be provided on a non-transitory computer-readable medium. In certain embodiments, processing may be performed using a digital signal processor (DSP) circuit or an application specific integrated circuit (ASIC).

What is claimed is:

1. A method for tracking activity by a wheelchair user, the method comprising:
   collecting motion data of a user device located on an appendage of the user;
   detecting, by a processor circuit, that one or more activities by the wheelchair user occurred based on the motion data, the detecting comprising tracking pushes by the wheelchair user by a method comprising:
      determining a pose angle and a calculated energy based on the motion data; and
      detecting, by the processor circuit, that a push occurred based on the determined pose angle and the calculated energy;
   estimating, by the processor circuit, an energy expenditure by the user based on the one or more activities; and
   outputting, by the processor circuit, the estimated energy expenditure.

2. The method of claim 1, wherein the motion sensor comprises an accelerometer, a gyroscope, a magnetometer, or a combination thereof.

3. The method of claim 1, wherein tracking pushes by the wheelchair user comprises:
   comparing, by the processor circuit, the determined pose angle with a pose angle threshold;
   comparing, by the processor circuit, the calculated energy with an energy threshold; and
   determining, by the processor circuit, that a push occurred when the determined pose angle is below the pose angle threshold and the calculated energy is above the energy threshold.

4. The method of claim 3, wherein tracking pushes by the wheelchair user comprises:
   storing pose angles and calculated energies for the wheelchair user;
   updating, by the processor circuit, the pose angle threshold using the stored pose angles; and
   updating, by the processor circuit, the energy threshold using the stored calculated energies.

5. The method of claim 4, wherein storing pose angles and calculated energies for the wheelchair user comprises:
   calculating, by the processor circuit, a current push rate for the user;
   determining, by the processor circuit, when the current push rate is consistent with previous push rates; and
   storing the determined pose angle and calculated energy when the current push rate is consistent with previous push rates.

6. The method of claim 4, wherein storing pose angles and calculated energies for the wheelchair user comprises:
   determining, by the processor circuit, a current speed for the user using a Global Positioning System (GPS) sensor; and
   storing the determined pose angle and calculated energy when the user's current speed is greater than or equal to a minimum speed threshold.

7. The method of claim 4, wherein:
updating the pose angle threshold comprises calculating a candidate pose angle threshold as a percentile of stored pose angles; and
updating the energy threshold comprises calculating a candidate energy threshold as a percentile of stored calculated energies.

8. The method of claim 7, wherein:
updating the pose angle threshold comprises calculating a new pose angle threshold using the candidate pose angle threshold and a first low-pass filter; and
updating the energy threshold comprises calculating a new energy threshold using the candidate energy threshold and a second low-pass filter.

9. A method for tracking activity by a wheelchair user, the method comprising:
collecting motion data of a user device located on an appendage of the user;
detecting, by a processor circuit, that one or more activities by the wheelchair user occurred based on the motion data, the detecting comprising tracking pushes by the wheelchair user by a method comprising:
selecting, by the processor circuit a dominant motion sensor axis based on a calculated motion energy per motion sensor axis;
performing, by the processor circuit, a frequency domain transformation of the collected motion data for the dominant motion sensor axis; and
determining, by the processor circuit, a fundamental push frequency based on the frequency domain transformed data;
estimating, by the processor circuit, an energy expenditure by the user based on the one or more activities; and
outputting, by the processor circuit, the estimated energy expenditure,
wherein the frequency domain transformation comprises a fast Fourier transform (FFT) operation, wherein detecting that a push occurred comprises:
determining, by the processor circuit, a FFT peak of a lowest frequency that rises above a pre-determined threshold level of energy; and
selecting, by the processor circuit, the lowest frequency as a fundamental frequency of pushing.

10. The method of claim 9, wherein tracking pushes by the wheelchair user comprises:
calculating, by the processor circuit, a motion energy for each motion sensor axis; and
selecting, by the processor circuit, a motion sensor axis with a most energy as a dominant motion sensor axis.

11. The method of claim 9, wherein the motion sensor comprises an accelerometer, a gyroscope, a magnetometer, or a combination thereof.

12. A method for tracking activity by a wheelchair user, the method comprising:
collecting motion data of a user device located on an appendage of the user;
detecting, by a processor circuit, that one or more activities by the wheelchair user occurred based on the motion data, the detecting comprising tracking pushes by the wheelchair user by a method comprising:
selecting, by the processor circuit, a dominant motion sensor axis based on a calculated motion energy per motion sensor axis;
performing, by the processor circuit, a frequency domain transformation of the collected motion data for the dominant motion sensor axis;
determining, by the processor circuit, a fundamental push frequency based on the frequency domain transformed data; and
filtering the collected data including adjusting an intelligent filter to pass motion sensor signals within a frequency band corresponding to the fundamental push frequency and to reduce motion sensor signals within a frequency band corresponding to harmonics of the fundamental push frequency;
estimating, by the processor circuit, an energy expenditure by the user based on the one or more activities; and
outputting, by the processor circuit, the estimated energy expenditure.

13. The method of claim 12, wherein the intelligent filter comprises a low-pass filter with adjustable passband width.

14. The method of claim 13, wherein the intelligent filter comprises a bank of low-pass filters with increasing passband widths.

15. The method of claim 13, wherein the intelligent filter comprises an adjustable bandpass filter with adjustable passband cutoff frequencies and widths.

16. The method of claim 12, wherein the motion sensor comprises an accelerometer, a gyroscope, a magnetometer, or a combination thereof.

17. A method for tracking activity by a wheelchair user, the method comprising:
collecting motion data of a user device located on an appendage of the user;
detecting, by a processor circuit, that one or more activities by the wheelchair user occurred based on the motion data, the detecting comprising tracking pushes by the wheelchair user by a method comprising:
determining a pose angle and a calculated energy based on the motion data;
detecting, by the processor circuit, that a push occurred based on the determined pose angle and the calculated energy;
filtering, by the processor circuit, the collected motion data to produced filtered motion data; and
determining, by the processor circuit, a push count based on zero-crossings of the filtered motion data;
estimating, by the processor circuit, an energy expenditure by the user based on the one or more activities; and
outputting, by the processor circuit, the estimated energy expenditure.

18. The method of claim 17, wherein determining a push count comprises:
detecting, by the processor circuit, one or more zero-crossings of the filtered motion data in one direction; and
determining, by the processor circuit, a push count equal to the number of zero-crossings.

19. The method of claim 17, further comprising:
cross-checking, by the processor circuit, the determined push count with motion data from a different motion sensor axis.

20. The method of claim 17, wherein the motion sensor comprises an accelerometer, a gyroscope, a magnetometer, or a combination thereof.

21. A method for tracking activity by a wheelchair user, the method comprising:
collecting motion data of a user device located on an appendage of the user;
detecting, by a processor circuit, that one or more activities by the wheelchair user occurred based on the motion data, the detecting comprising detecting when a wheelchair user is traveling on a ramp by a method comprising:
  determining, by the processor circuit, a ramp classification based on the collected motion data; and
  filtering, by the processor circuit, the determined ramp classification using a filter;
estimating, by the processor circuit, an energy expenditure by the user based on the one or more activities; and
outputting, by the processor circuit, the estimated energy expenditure.

22. The method of claim 21, wherein determining a ramp classification comprises determining a ramp classification based on a push rate, a first push rate threshold, an energy component of the collected motion data, and at least one of a first energy threshold, a second energy threshold, a pose angle, a pose angle threshold, and a second push rate threshold.

23. The method of claim 22, wherein detecting when the wheelchair user is traveling on a ramp comprises comparing, by the processor circuit, the push rate with the first push rate threshold, and at least one of:
  comparing, by the processor circuit, the energy component of the collected motion data with the first energy threshold;
  comparing, by the processor circuit, the pose angle with the pose angle threshold;
  comparing, by the processor circuit, the energy component of the collected motion data with the second energy threshold; and
  comparing, by the processor circuit, the push rate with the second push rate threshold.

24. The method of claim 22, wherein detecting when the wheelchair user is traveling on a ramp comprises:
  obtaining per-user thresholds; and
  adjusting, by the processor circuit, at least one of the first and second push rate thresholds, the first and second energy thresholds, and the pose angle threshold using the per-user thresholds.

25. The method of claim 21, wherein the filter comprises a windowing filter.

26. The method of claim 25, wherein the windowing filter comprises an odd number of points in the window.

27. The method of claim 26, wherein the windowing filter comprises a three-point window.

28. The method of claim 21, wherein the motion sensor comprises an accelerometer, a gyroscope, a magnetometer, or a combination thereof.

29. A method for tracking activity by a wheelchair user, the method comprising:
  collecting motion data of a user device located on an appendage of the user;
  detecting, by a processor circuit, that one or more activities by the wheelchair user occurred based on the motion data, the detecting comprising detecting wheelchair user stroke type by a method comprising:
    measuring X axis and Y axis accelerometer data from an accelerometer located on an arm of the user;
    detecting a Y axis accelerometer peak corresponding to a push phase;
    determining adjacent zero crossings to the Y axis accelerometer peak to determine the start and end of the push phase and a return phase;
    determining a length of the push phase;
    detecting X peaks in X axis accelerometer data during the return phase;
    detecting Y peaks in Y axis accelerometer data during the return phase;
    determining signs for the X peaks and the Y peaks;
    determining an ordered sequence of the determined X signs;
    determining an ordered sequence of the determined Y signs;
    determining stroke type based on the sequence of X signs and the sequence of Y signs; and
    applying one of the determined stroke type and the determined push phase length in a calorie expenditure tracking system;
  estimating, by the processor circuit, an energy expenditure by the user based on the one or more activities; and
  outputting, by the processor circuit, the estimated energy expenditure.

30. A method for tracking activity by a wheelchair user, the method comprising:
  collecting motion data of a user device located on an appendage of the user;
  detecting, by a processor circuit, that one or more activities by the wheelchair user occurred based on the motion data;
  estimating, by a processor circuit, an energy expenditure by the user based on the one or more activities, wherein estimating the energy expenditure by the user comprises:
    measuring at least one of X accelerometer data, Y accelerometer data, Z accelerometer data, X rotational data, Y rotational data, Z rotational data, barometer data, altimeter data, GPS position data, GPS speed data, GPS altitude data, and heart rate data;
    receiving user input regarding at least one of fitness level, age, weight, injury type, and mobility level;
    determining an estimated speed based on the measured data;
    determining an estimated MET value based on the estimated speed;
    determining a ramp state based on the measured data;
    refining the estimated MET value based on the determined ramp state;
    determining an energy expenditure estimate based on the estimated MET value;
    determining a physiological efficiency estimate based on the user input;
    refining the physiological efficiency estimate based on the measured data;
    refining the energy expenditure estimate using the physiological efficiency estimate; and
    applying the refined energy expenditure estimate in a calorie expenditure tracking system; and
  outputting, by the processor circuit, the estimated energy expenditure.

31. A method for tracking activity by a wheelchair user, the method comprising:
  collecting motion data of a user device located on an appendage of the user;
  detecting, by a processor circuit, that one or more activities by the wheelchair user occurred based on the motion data, the detecting comprising detecting when the wheelchair user is engaging in a transfer from or shift in the wheelchair by a method comprising:
    collecting motion data of a user device located on an appendage of the user;
    extracting, by the processor circuit, one or more features of interest from the collected motion data;

detecting, by the processor circuit, that the user engaged in a wheelchair shift or transfer based on the one or more features and one or more corresponding thresholds for the one or more features;
in response to detecting the wheelchair shift or transfer, updating a current state of a state machine; and
triggering a reminder to the user based on the current state of the state machine;
estimating, by the processor circuit, an energy expenditure by the user based on the one or more activities; and
outputting, by the processor circuit, the estimated energy expenditure.

* * * * *